(12) United States Patent
Huse et al.

(10) Patent No.: US 7,667,007 B2
(45) Date of Patent: *Feb. 23, 2010

(54) αVβ3-SPECIFIC ANTIBODIES

(75) Inventors: William D. Huse, Del Mar, CA (US); Herren Wu, San Diego, CA (US)

(73) Assignee: Applied Molecular Evolution, Inc., San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 12/102,818

(22) Filed: Apr. 14, 2008

(65) Prior Publication Data

US 2009/0023900 A1 Jan. 22, 2009

Related U.S. Application Data

(60) Continuation of application No. 10/305,231, filed on Nov. 25, 2002, now Pat. No. 7,371,382, which is a division of application No. 09/339,922, filed on Jun. 24, 1999, now Pat. No. 6,531,580.

(51) Int. Cl.
C07K 16/28 (2006.01)

(52) U.S. Cl. ............... 530/388.73; 530/387.1; 530/387.3; 530/388.1; 530/388.2; 530/388.7

(58) Field of Classification Search ............... None
See application file for complete search history.

(56) References Cited

U.S. PATENT DOCUMENTS

| | | | |
|---|---|---|---|
| 5,225,539 A | 7/1993 | Winter | |
| 5,264,563 A | 11/1993 | Huse | |
| 5,523,388 A | 6/1996 | Huse | |
| 5,578,704 A | 11/1996 | Kim et al. | |
| 5,585,089 A | 12/1996 | Queen et al. | |
| 5,693,762 A | 12/1997 | Queen et al. | |
| 5,753,230 A * | 5/1998 | Brooks et al. | 424/158.1 |
| 5,766,591 A | 6/1998 | Brooks et al. | |
| 6,096,551 A | 8/2000 | Barbas et al. | |
| 6,180,370 B1 | 1/2001 | Queen et al. | |
| 6,531,580 B1 * | 3/2003 | Huse et al. | 530/388.22 |
| 6,590,079 B2 | 7/2003 | Huse et al. | |
| 6,596,850 B1 | 7/2003 | Huse | |
| 6,887,473 B1 | 5/2005 | Brooks et al. | |
| 7,371,382 B2 * | 5/2008 | Huse et al. | 424/144.1 |
| 7,422,744 B2 | 9/2008 | Huse et al. | |

FOREIGN PATENT DOCUMENTS

| | | |
|---|---|---|
| EP | 0 451 216 | 10/1991 |
| EP | 0 682 040 | 11/1993 |
| WO | WO 95/25543 | 9/1995 |
| WO | WO 96/40250 | 12/1996 |
| WO | WO 98/33919 | 8/1998 |

OTHER PUBLICATIONS

MacCallum et al., J. Mol. Biol. 262: 732-745, 1996.*
Padlan et al., PNAS 86: 5938-5942, 1989.*
Lamminmaki et al., J. Biol. Chem. 276: 36687-36694, 2001.*
Adams et al., "Increased Affinity Leads to Improved Selective Tumor Delivery of Single-Chain Fv Antibodies," *Cancer Res.* 58:485-490 (1998).
Alfthan, "Surface Plasmon resonance biosensors as a tool in antibody engineering," *Biosensors and Bioelectronics*, 13:653-663 (1998).
Biedler, "Mammalian expression and characterization of a dimeric single chain antibody specific for integrin alpha-v-beta-3," *Immunotech.*, 2:297 (1996).
Biotechnology Newswatch, pp. 11 (Feb. 6, 1995).
Biotechnology Newswatch, pp. 11-12 (Jan. 16, 1995).
Brooks et al., "Integrin alpha v beta 3 antagonists promote tumor regression by inducing apoptosis of angiogenic blood vessels.," *Cell* 79:1157-1164 (1994).
Carmeliet, "Integrin indecision," *Nature Medicine* 8:14-16 (2002).
Chen et al., "Enhancement and destruction of antibody function by somatic mutation: unequal occurrence is controlled by V gene combinatorial associations," *EMBO J.*, 14:2784-2794 (1995).
Cheresh et al., "Biosynthetic and functional properties of an Arg-Gly-Asp-directed receptor involved in human melanoma cell attachment to vitronectin, fibrinogen, and von Willebrand factor," *J. Biol. Chem.* 262(36):17703-17711 (1987).
Cheresh et al., "Integrin-mediated death: An explanation of the integrin-knockout phenotype?" *Nature Medicine* 8:193-194 (2002).
Cheresh, "Human endothelial cells synthesize and express an Arg-Gly-Asp directed adhesion redeptor involved in attachment to fibrinogen and von Willebrand factor," *Proc. Natl. Acad. Sci. USA* 84:6471-6475 (1987).
Choi et al., "Inhibition of neointimal hyperplasia by blocking alpha V beta 3 integrin with a small peptide antagonist GpenGRGDSPCA," *J. Vascular Surg.*, 19:125-134 (1994).
Chothia et al., "Canonical Structures for the Hypervariable Regions of Immunoglobulins," *J. Mol. Biol.* 196:901-917 (1987).
Chowdhury et al., "Improving antibody affinity by mimicking somatic hypermutation in vitro," *Nature Biotech.* 17:568-572 (1999).
Clark, "Protein Engineering of Antibody Molecules for Prophylactic and Therapeutic Applications in Man," Nottingham, England: Academic Titles (1993).
Colman, Effects of amino acid sequence changes on antibody-antigen interactions, *Res Immunol.*, 145:33-36 (1994).
Davies et al., "Affinity improvement of single antibody VH domains: Residues in all three hypervariable regions affect antigen binding," *Immunotech.*, 2:169-179 (1996).
Day, *Advanced Immunochemistry*, Second Ed., Wiley-Liss, Inc., New York, NY (1990).
Devlin et al., "Random peptide libraries: a source of specific protein binding molecules," *Science* 249:404-406 (1990).
Dorland'S Illustrated Medical Dictionary, Twenty-sixth Ed. W.B. Saunders Company, Philadelphia, 1981, p. 385.
Dueñas et al., "Selection of Phage Displayed Antibodies Based on Kinetic Constants," *Molec. Immunol.*, 33(3):279-285 (1996).

(Continued)

*Primary Examiner*—Phillip Gambel
(74) *Attorney, Agent, or Firm*—McDermott Will & Emery LLP

(57) ABSTRACT

The invention provides enhanced LM609 grafted antibodies exhibiting selective binding affinity to $\alpha_v\beta_3$, or a functional fragment thereof. The invention also provides nucleic acid molecules encoding the enhanced LM609 grafted antibodies. Additionally provided are methods of inhibiting a function of $\alpha_v\beta_3$ by contacting $\alpha_v\beta_3$ with an enhanced LM609 grafted antibody.

5 Claims, 15 Drawing Sheets

OTHER PUBLICATIONS

Foote et al., "Kinetic maturation of an immune response," *Nature* 352:530-532 (1991).
Glaser et al., "Antibody engineering by codon-based mutagenesis in a filamentous phage vector system," *J. Immunol.* 149:3903-3913 (1992).
Hawkins et al., "Selection of phage antibodies by binding affinity. Mimicking affinity maturation," *J. Mol. Biol.*, 226:889-896 (1992).
Huse et al., "Application of a Filamentous Phage pVIII Fusion Protein System Suitable for Efficient Production, Screening, and Mutagenisis of F(ab) Antibody Fragments," *J. Immunol.* 149:3914-3920 (1992).
Huse, "Combinatorial Antibody Expression Libraries in Filamentous Phage," In: Antibody Engineering: A Practical Guide, C.A.K. Borrebaeck, ed. W.H. Freeman and Co., Publishers, New York, pp. 103-120 (1991).
Huston et al., "Antigen Recognition and Targeted Delivery by the Single-Chain Fv," *Cell Biophysics*, 22:189-224 (1993).
Kabat et al., U.S. Dept. of Health and Human Services, "Sequences of Proteins of Immunological Interest," vol. 1 pp. i-xcvi (1991).
Kussie et al., "A single Engineered Amino Acid Substitution Changes antibody Fine Specificity," *J. Immunol.* 152:146-152 (1994).
Moore et al., "Directed evolution of a para-nitrobenzyl esterase for aqueous-organic solvents," *Nat Biotechnol.* 14:458-467 (1996).
Morrison et al., "Genetically Engineered Antibody Molecules," *Adv. Immunol.*, 44:65-92 (1989).
Myszka et al., "Kinetic analysis of a protein antigen-antibody interaction limited by mass transport on an optical biosensor," *Biophys. Chem.*, 64:127-137 (1997).
Newman et al., ""Primatization" of Recombinant Antibodies for Immunotherapy of Human Diseases: A Macaque/Human Chimeric Antibody Against Human CD4," *Biotechnol.*, 10:1455-1460 (1992).
Padlan, "A possible procedure for reducing the immunogenicity of antibody variable domains while preserving their ligand-binding properties," *Molecular Immunol.*, 28(4/5):489-498 (1991).
Plückthun et al., "Expression of functional antibody Fv and Fab fragments in *Escherichia coli*," *Meth. Enzymol.* 178-497-515 (1989).
Posey et al., "A Pilot Trial of Vitzin, A Humanized Anti-Vitronection Receptor (anti $\alpha\gamma\beta_3$) Antibody in Patients with Metastatic Cancer" *Cancer Biother. Radiopharm.* 16:125-132 (2001).
Rader et al., "A phage display approach for rapid antibody humanization: Designed combinatorial V gene libraries," *Proc. Natl. Acad. Sci.* 95:8910-8915 (1998).

Reynolds et al., "Enhanced pathological angiogenesis in mice lacking $\beta_3$ integrin or $\beta_3$ and $\beta_5$ integrins," *Nature Medicine* 8:27-34 (2002).
Rosok et al., "A Combinatorial Library Strategy for the Rapid Humanization of Annticarcinoma BR96 Fab," *J. Biol. Chem.* 271:22611-22618 (1996).
Rudikoff et al. "Single amino acid substitution altering antigen-binding specificity," *Proc. Natl. Acad. Sci.* 79:1979-1983 (1982).
Sandberg and Terwilliger, "Engineering multiple properties of a protein by combinatorial mutagenesis," *Proc. Natl. Acad. Sci.* 90:8367-8371 (1993).
Schier et al., "Efficient in vitro affinity maturation of phage antibodies using BIAcore guided selections," *Hum. Antibod. Hybridomas*, 7:97-105 (1996).
Schier et al., "Isolation of high-affinity monomeric human anti-c-erbB-2 single chain Fv using affinity-driven selection," *J. Mol. Biol.*, 255:28-43 (1996).
Schier et al., "Isolation of picomolar affinity anti-c-erbB-2 single-chain Fv by molecular evolution of the complementarity determining regions in the center of the antibody binding site," *J. Mol. Biol.*, 263:551-567 (1996).
Singer et al., "Optimal humanization of 1B4, an anti-CD18 murine monoclonal antibody, is achieved by correct choice of human V-region framework sequences," *J. Immunol.* 150(7):2844-2857 (1993).
Stedman's Medical Dictionary, 24th Ed., Williams & Wilkins, Baltimore, 1982, p. 403.
Studnicka et al., "Human engineered monoclonal antibodies retain full specific binding activity by preserving non-CDR complementarity-modulating residues," *Protein Engineering* 7:805-814 (1994).
Stupack et al., "Get a ligand, get a life: integrins, signaling and cell survival," *J. Cell Science* 115:3729-3738 (2002).
Thompson et al., "Affinity maturation of a high-affinity human monoclonal antibody against the third hypervariable loop of human immunodeficiency virus: use of phage display to improve affinity and broaden strain reactivity," *J. Mol. Biol.* 256:77-88 (1996).
Wu et al., "Stepwise in vitro affinity maturation of Vitaxin, an alphav beta3-specific humanized mAb," *Proc. Natl. Acad. Sci. USA* 95:6037-6042 (1998).
Webster's II New Riverside University Dictionary, The Riverside Publishing Company, Boston, 1994, p. 385.
Yelton et al., "Affinity Maturation of the BR96 Anti-Carcinoma Antibody by Condon-Based Mutagenesis," *J. Immunol.* 155:1994-2004 (1995).

* cited by examiner

| | | | | | | | | |
|---|---|---|---|---|---|---|---|---|
| CAG<br>Gln<br>1 | GTG<br>Val | CAG<br>Gln | CTG<br>Leu | GTG<br>Val<br>5 | GAG<br>Glu | TCT<br>Ser | GGG<br>Gly | GGA<br>Gly | GGC<br>Gly<br>10 | GTT<br>Val | GTG<br>Val | CAG<br>Gln | CCT<br>Pro | GGA<br>Gly<br>15 | AGG<br>Arg | 48 |
| TCC<br>Ser | CTG<br>Leu | AGA<br>Arg | CTC<br>Leu<br>20 | TCC<br>Ser | TGT<br>Cys | GCA<br>Ala | GCC<br>Ala | TCT<br>Ser<br>25 | GGA<br>Gly | TTC<br>Phe | ACC<br>Thr | TTC<br>Phe | AGT<br>Ser<br>30 | AGC<br>Ser | TAT<br>Tyr | 96 |
| GAC<br>Asp | ATG<br>Met | TCT<br>Ser<br>35 | TGG<br>Trp | GTT<br>Val | CGC<br>Arg | CAG<br>Gln | GCT<br>Ala<br>40 | CCG<br>Pro | GGC<br>Gly | AAG<br>Lys | GGT<br>Gly | CTG<br>Leu<br>45 | GAG<br>Glu | TGG<br>Trp | GTC<br>Val | 144 |
| GCA<br>Ala | AAA<br>Lys<br>50 | GTT<br>Val | AGT<br>Ser | GGT<br>Gly | GGT<br>Gly<br>55 | GGT<br>Gly | AGC<br>Ser | ACC<br>Thr | TAC<br>Tyr | TAT<br>Tyr<br>60 | GCT<br>Ala | GAC<br>Asp | TCT<br>Ser | GTG<br>Val | AAG<br>Lys | 192 |
| CAG<br>Gln<br>65 | GGC<br>Gly | CGA<br>Arg | TTC<br>Phe | ACC<br>Thr | ATC<br>Ile<br>70 | TCC<br>Ser | AGA<br>Arg | GAC<br>Asp | AAT<br>Asn | AGT<br>Ser<br>75 | AAG<br>Lys | AAC<br>Asn | ACC<br>Thr | CTA<br>Leu | TAC<br>Tyr<br>80 | 240 |
| CTG<br>Leu | CAA<br>Gln | ATG<br>Met | AAC<br>Asn | TCT<br>Ser<br>85 | CTG<br>Leu | AGA<br>Arg | GCC<br>Ala | GAG<br>Glu | GAC<br>Asp<br>90 | ACA<br>Thr | GCC<br>Ala | GTG<br>Val | TAT<br>Tyr | TAC<br>Tyr<br>95 | TGT<br>Cys | 288 |
| GCA<br>Ala | AGA<br>Arg | CAT<br>His | AAC<br>Asn<br>100 | TAC<br>Tyr | GGC<br>Gly | AGT<br>Ser | TTT<br>Phe | GCT<br>Ala<br>105 | TAC<br>Tyr | TGG<br>Trp | GGC<br>Gly | CAA<br>Gln | GGG<br>Gly<br>110 | ACT<br>Thr | ACA<br>Thr | 336 |
| GTG<br>Val | ACT<br>Thr | GTT<br>Val<br>115 | TCT<br>Ser | AGT<br>Ser | | | | | | | | | | | | 351 |

FIG. 1A

```
GAG ATT GTG CTA ACT CAG TCT CCA GCC ACC CTG TCT CTC AGC CCA GGA        48
Glu Ile Val Leu Thr Gln Ser Pro Ala Thr Leu Ser Leu Ser Pro Gly
  1               5                  10                  15

GAA AGG GCG ACT CTT TCC TGC AGG GCC AGT CAA AGT ATT AGC AAC CAC        96
Glu Arg Ala Thr Leu Ser Cys Arg Ala Ser Gln Ser Ile Ser Asn His
             20                  25                  30

CTA CAC TGG TAT CAA CAA CAA AGG CCT GGT CAA GCC CCA AGG CTC ATC       144
Leu His Trp Tyr Gln Gln Gln Arg Pro Gly Gln Ala Pro Arg Leu Ile
         35                  40                  45

AAG TAT CGT TCC CAG TCC ATC TCT GGG ATC CCC GCC AGG TTC AGT GGC       192
Lys Tyr Arg Ser Gln Ser Ile Ser Gly Ile Pro Ala Arg Phe Ser Gly
     50                  55                  60

AGT GGA TCA GGG ACA GAT TTC ACC CTC ACT ATC TCC AGT CTG GAG CCT       240
Ser Gly Ser Gly Thr Asp Phe Thr Leu Thr Ile Ser Ser Leu Glu Pro
 65                  70                  75                  80

GAA GAT TTT GCA GTC TAT TAC TGT CAA CAG AGT GGC AGC TGG CCT CAC       288
Glu Asp Phe Ala Val Tyr Tyr Cys Gln Gln Ser Gly Ser Trp Pro His
                 85                  90                  95

ACG TTC GGA GGG GGG ACC AAG GTG GAA ATT AAG                           321
Thr Phe Gly Gly Gly Thr Lys Val Glu Ile Lys
             100                 105
```

FIG. 1B

```
GAA GTG CAG CTG GTG GAG TCT GGG GGA GGC TTA GTG AAG CCT GGA AGG     48
Glu Val Gln Leu Val Glu Ser Gly Gly Gly Leu Val Lys Pro Gly Arg
  1               5                  10                  15

TCC CTG AGA CTC TCC TGT GCA GCC TCT GGA TTC GCT TTC AGT AGC TAT     96
Ser Leu Arg Leu Ser Cys Ala Ala Ser Gly Phe Ala Phe Ser Ser Tyr
             20                  25                  30

GAC ATG TCT TGG GTT CGC CAG ATT CCG GAG AAG AGG CTG GAG TGG GTC    144
Asp Met Ser Trp Val Arg Gln Ile Pro Glu Lys Arg Leu Glu Trp Val
         35                  40                  45

GCA AAA GTT AGT AGT GGT GGT GGT AGC ACC TAC TAT TTA GAC ACT GTG    192
Ala Lys Val Ser Ser Gly Gly Gly Ser Thr Tyr Tyr Leu Asp Thr Val
     50                  55                  60

CAG GGC CGA TTC ACC ATC TCC AGA GAC AAT GCC AAG AAC ACC CTA TAC    240
Gln Gly Arg Phe Thr Ile Ser Arg Asp Asn Ala Lys Asn Thr Leu Tyr
 65                  70                  75                  80

CTG CAA ATG AGC AGT CTG AAC TCT GAG GAC ACA GCC ATG TAT TAC TGT    288
Leu Gln Met Ser Ser Leu Asn Ser Glu Asp Thr Ala Met Tyr Tyr Cys
                 85                  90                  95

GCA AGA CAT AAC TAC GGC AGT TTT GCT TAC TGG GGC CAA GGG ACT CTG    336
Ala Arg His Asn Tyr Gly Ser Phe Ala Tyr Trp Gly Gln Gly Thr Leu
            100                 105                 110

GTC ACT GTC TCT GCA                                                351
Val Thr Val Ser Ala
        115
```

FIG. 2A

| | | | | | | | | | | | | | | | |
|---|---|---|---|---|---|---|---|---|---|---|---|---|---|---|---|
| GAT | ATT | GTG | CTA | ACT | CAG | TCT | CCA | GCC | ACC | CTG | TCT | GTG | ACA | CCA | GGA | 48 |
| Asp | Ile | Val | Leu | Thr | Gln | Ser | Pro | Ala | Thr | Leu | Ser | Val | Thr | Pro | Gly |
| 1 | | | | 5 | | | | | 10 | | | | | 15 | |
| GAT | AGC | GTC | AGT | CTT | TCC | TGC | CAG | GCC | AGC | CAA | AGT | ATT | AGC | AAC | CAC | 96 |
| Asp | Ser | Val | Ser | Leu | Ser | Cys | Gln | Ala | Ser | Gln | Ser | Ile | Ser | Asn | His |
| | | | 20 | | | | | 25 | | | | | 30 | | |
| CTA | CAC | TGG | TAT | CAA | CAA | AAA | TCA | CAT | GAG | TCT | CCA | AGG | CTT | CTC | ATC | 144 |
| Leu | His | Trp | Tyr | Gln | Gln | Lys | Ser | His | Glu | Ser | Pro | Arg | Leu | Leu | Ile |
| | | 35 | | | | | 40 | | | | | 45 | | | |
| AAG | TAT | CGT | TCC | CAG | TCC | ATC | TCT | GGG | ATC | CCC | TCC | AGG | TTC | AGT | GGC | 192 |
| Lys | Tyr | Arg | Ser | Gln | Ser | Ile | Ser | Gly | Ile | Pro | Ser | Arg | Phe | Ser | Gly |
| | 50 | | | | | 55 | | | | | 60 | | | | |
| AGT | GGA | TCA | GGG | ACA | GAT | TTC | GCT | CTC | AGT | ATC | AAC | AGT | GTG | GAG | ACT | 240 |
| Ser | Gly | Ser | Gly | Thr | Asp | Phe | Ala | Leu | Ser | Ile | Asn | Ser | Val | Glu | Thr |
| 65 | | | | | 70 | | | | | 75 | | | | | 80 |
| GAA | GAT | TTT | GGA | ATG | TAT | TTC | TGT | CAA | CAG | AGT | GGC | AGC | TGG | CCT | CAC | 288 |
| Glu | Asp | Phe | Gly | Met | Tyr | Phe | Cys | Gln | Gln | Ser | Gly | Ser | Trp | Pro | His |
| | | | | 85 | | | | | 90 | | | | | 95 | |
| ACG | TTC | GGA | GGG | GGG | ACC | AAG | CTG | GAA | ATT | AAG | | | | | | 321 |
| Thr | Phe | Gly | Gly | Gly | Thr | Lys | Leu | Glu | Ile | Lys |
| | | | 100 | | | | | 105 | | | |

FIG. 2B

| | | | | | | | | | | | | | | | |
|---|---|---|---|---|---|---|---|---|---|---|---|---|---|---|---|
| GAG | ATT | GTG | CTA | ACT | CAG | TCT | CCA | GCC | ACC | CTG | TCT | CTC | AGC | CCA | GGA |
| Glu | Ile | Val | Leu | Thr | Gln | Ser | Pro | Ala | Thr | Leu | Ser | Leu | Ser | Pro | Gly |
| 1 | | | | 5 | | | | | 10 | | | | | 15 | |

48

| | | | | | | | | | | | | | | | |
|---|---|---|---|---|---|---|---|---|---|---|---|---|---|---|---|
| GAA | AGG | GCG | ACT | CTT | TCC | TGC | CAG | GCC | AGC | CAA | AGT | ATT | AGC | AAC | CAC |
| Glu | Arg | Ala | Thr | Leu | Ser | Cys | Gln | Ala | Ser | Gln | Ser | Ile | Ser | Asn | His |
| | | 20 | | | | | 25 | | | | | 30 | | | |

96

| | | | | | | | | | | | | | | | |
|---|---|---|---|---|---|---|---|---|---|---|---|---|---|---|---|
| CTA | CAC | TGG | TAT | CAA | CAA | AGG | CCT | GGT | CAA | GCC | CCA | AGG | CTT | CTC | ATC |
| Leu | His | Trp | Tyr | Gln | Gln | Arg | Pro | Gly | Gln | Ala | Pro | Arg | Leu | Leu | Ile |
| | 35 | | | | | | 40 | | | | | 45 | | | |

144

| | | | | | | | | | | | | | | | |
|---|---|---|---|---|---|---|---|---|---|---|---|---|---|---|---|
| CGT/ATG | TAT | CGT | TCC | CAG | TCC | ATC | TCT | GGG | ATC | CCC | GCC | AGG | TTC | AGT | GGC |
| Arg/Met | Tyr | Arg | Ser | Gln | Ser | Ile | Ser | Gly | Ile | Pro | Ala | Arg | Phe | Ser | Gly |
| 50 | | | | | 55 | | | | | 60 | | | | | |

192

| | | | | | | | | | | | | | | | |
|---|---|---|---|---|---|---|---|---|---|---|---|---|---|---|---|
| AGT | GGA | TCA | GGG | ACA | GAT | TTC | ACC | CTC | ACT | ATC | TCC | AGT | CTG | GAG | CCT |
| Ser | Gly | Ser | Gly | Thr | Asp | Phe | Thr | Leu | Thr | Ile | Ser | Ser | Leu | Glu | Pro |
| 65 | | | | | 70 | | | | | 75 | | | | | 80 |

240

| | | | | | | | | | | | | | | | |
|---|---|---|---|---|---|---|---|---|---|---|---|---|---|---|---|
| GAA | GAT | TTT | GCA | GTC | TAT | TAC | TGT | CAA | CAG | AGT | GGC | AGC | TGG | CCT | CAC |
| Glu | Asp | Phe | Ala | Val | Tyr | Tyr | Cys | Gln | Gln | Ser | Gly | Ser | Trp | Pro | His |
| | | | 85 | | | | | | 90 | | | | | 95 | |

288

| | | | | | | | | |
|---|---|---|---|---|---|---|---|---|
| ACG | TTC | GGA | GGG | ACC | AAG | GTG | GAA | ATT | AAG |
| Thr | Phe | Gly | Gly | Thr | Lys | Val | Glu | Ile | Lys |
| | | 100 | | | | | | 105 | |

αVβ3-SPECIFIC ANTIBODIES

This application is a continuation of application Ser. No. 10/305,231, filed Nov. 25, 2002, now U.S. Pat. No. 7,371,382, which is a divisional of application Ser. No. 09/339,922, filed Jun. 24, 1999, now U.S. Pat. No. 6,531,580, the entire contents of each of which are incorporated herein.

BACKGROUND OF THE INVENTION

The present invention relates generally to integrin mediated diseases and, more particularly, to nucleic acids encoding $\alpha_v\beta_3$-inhibitory monoclonal antibodies and to CDR grafted $\alpha_v\beta_3$-inhibitory antibodies for the therapeutic treatment of $\alpha_v\beta_3$-mediated diseases.

Integrins are a class of cell adhesion receptors that mediate both cell-cell and cell-extracellular matrix adhesion events. Integrins consist of heterodimeric polypeptides where a single a chain polypeptide noncovalently associates with a single β chain. There are now about 14 distinct a chain polypeptides and at least about 8 different β chain polypeptides which constitute the integrin family of cell adhesion receptors. In general, different binding specificities and tissue distributions are derived from unique combinations of the α and β chain polypeptides or integrin subunits. The family to which a particular integrin is associated with is usually characterized by the β subunit. However, the ligand binding activity of the integrin is largely influenced by the a subunit. For example, vitronectin binding integrins contain the $\alpha_v$ integrin subunit.

It is now known that the vitronectin binding integrins consist of at least three different $\alpha_v$ containing integrins. These $\alpha_v$ containing integrins include $\alpha_v\beta_3$, $\alpha_v\beta_1$ and $\alpha_v\beta_5$, all of which exhibit different ligand binding specificities. For example, in addition to vitronectin, $\alpha_v\beta_3$ binds to a large variety of extracellular matrix proteins including fibronectin, fibrinogen, laminin, thrombospondin, von Willebrand factor, collagen, osteopontin and bone sialoprotein I. The integrin $\alpha_v\beta_1$ binds to fibronectin, osteopontin and vitronectin whereas $\alpha_v\beta_5$ is known to bind to vitronectin and osteopontin.

As cell adhesion receptors, integrins are involved in a variety of physiological processes including, for example, cell attachment, cell migration and cell proliferation. Different integrins play different roles in each of these biological processes and the inappropriate regulation of their function or activity can lead to various pathological conditions. For example, inappropriate endothelial cell proliferation during neovascularization of a tumor has been found to be mediated by cells expressing vitronectin binding integrins. In this regard, the inhibition of the vitronectin-binding integrin $\alpha_v\beta_3$ also inhibits this process of tumor neovascularization. By this same criteria, $\alpha_v\beta_3$ has also been shown to mediate the abnormal cell proliferation associated with restenosis and granulation tissue development in cutaneous wounds, for example. Additional diseases or pathological states mediated or influenced by $\alpha_v\beta_3$ include, for example, metastasis, osteoporosis, age-related macular degeneration and diabetic retinopathy, and inflammatory diseases such as rheumatoid arthritis and psoriasis. Thus, agents which can specifically inhibit vitronectin-binding integrins would be valuable for the therapeutic treatment of diseases.

Many integrins mediate their cell adhesive functions by recognizing the tripeptide sequence Arg-Gly-Asp (RGD) found within a large number of extracellular matrix proteins. A variety of approaches have attempted to model agents after this sequence to target a particular integrin-mediated pathology. Such approaches include, for example, the use of RGD-containing peptides and peptide analogues which rely on specificity to be conferred by the sequences flanking the RGD core tripeptide sequence. Although there has been some limited success, most RGD-based inhibitors have been shown to be, at most, selective for the targeted integrin and therefore exhibit some cross-reactivity to other non-targeted integrins. Such cross-reactive inhibitors therefore lack the specificity required for use as an efficacious therapeutic. This is particularly true for previously identified inhibitors of the integrin $\alpha_v\beta_3$.

Monoclonal antibodies on the other hand exhibit the specificity required to be used as an effective therapeutic. Antibodies also have the advantage in that they can be routinely generated against essentially any desired antigen. Moreover, with the development of combinatorial libraries, antibodies can now be produced faster and more efficiently than by previously used methods within the art. The use of combinatorial methodology also allows for the selection of the desired antibody along with the simultaneous isolation of the encoding heavy and light chain nucleic acids. Thus, further modification can be performed to the combinatorial antibody without the incorporation of an additional cloning step.

Regardless of the potential advantages associated with the use of monoclonal antibodies as therapeutics, these molecules nevertheless have the drawback in that they are almost exclusively derived from non-human mammalian organisms. Therefore, their use as therapeutics is limited by the fact that they will normally elicit a host immune response. Methods for substituting the antigen binding site or complementarity determining regions (CDRs) of the non-human antibody into a human framework have been described. Such methods vary in terms of which amino acid residues should be substituted as the CDR as well as which framework residues should be changed to maintain binding specificity. In this regard, it is understood that proper orientation of the β sheet architecture, correct packing of the heavy and light chain interface and appropriate conformation of the CDRs are all important for preserving antigen specificity and affinity within the grafted antibody. However, all of these methods require knowledge of the nucleotide and amino acid sequence of the non-human antibody and the availability of an appropriately modeled human framework.

Thus, there exists a need for the availability of nucleic acids encoding integrin inhibitory antibodies which can be used as compatible therapeutics in humans. For $\alpha_v\beta_3$-mediated diseases, the present invention satisfies this need and provides related advantages as well.

SUMMARY OF THE INVENTION

The invention provides enhanced LM609 grafted antibodies exhibiting selective binding affinity to $\alpha_v\beta_3$, or a functional fragment thereof. The invention also provides nucleic acid molecules encoding the enhanced LM609 grafted antibodies. Additionally provided are methods of inhibiting a function of $\alpha_v\beta_3$ by contacting $\alpha_v\beta_3$ with an enhanced LM609 grafted antibody.

BRIEF DESCRIPTION OF THE DRAWINGS

FIG. 1 shows the nucleotide and deduced amino acid sequence of the variable region of the antibody Vitaxin. FIG. 1A shows the nucleotide and deduced amino acid sequences for the Vitaxin heavy chain variable region (Gln1-Ser117; SEQ ID NOS:1 and 2, respectively) while FIG. 1B shows the nucleotide and deduced amino acid sequences for the Vitaxin light chain variable region (Glu1-Lys107; SEQ ID NOS:3 and 4, respectively).

FIG. 2 shows the nucleotide and deduced amino acid sequence of the variable region of the monoclonal antibody LM609. FIG. 2A shows the nucleotide and deduced amino acid sequence of the LM609 heavy chain variable region (SEQ ID NOS:5 and 6, respectively). The variable region extends from amino acid Glu1 to Ala117. FIG. 2B shows the nucleotide and deduced amino acid sequence of the LM609 light chain variable region (SEQ ID NOS:7 and 8, respectively). The variable region of the light chain extends from amino acid Asp1 to Lys107.

FIG. 4 shows the characterization of Vitaxin binding specificity.

FIG. 6 shows the reduction in tumor growth due to Vitaxin mediated inhibition of neovascularization.

FIG. 7 shows the nucleotide and deduced amino acid sequence of the light chain variable region of the LM609 grafted antibody fragment (Glu1-Lys107; SEQ ID NOS:31 and 32, respectively). Position 49 of the light chain variable region can at least be either Arg or Met. The nucleotide and deduced amino acid sequence of the heavy chain variable region of the LM609 grafted antibody fragment is shown in FIG. 1A (SEQ ID NOS:1 and 2, respectively).

FIG. 10 shows the inhibition of fibrinogen binding to $\alpha_v\beta_3$ by LM609 grafted antibody variants.

DETAILED DESCRIPTION OF THE INVENTION

Figure 3:
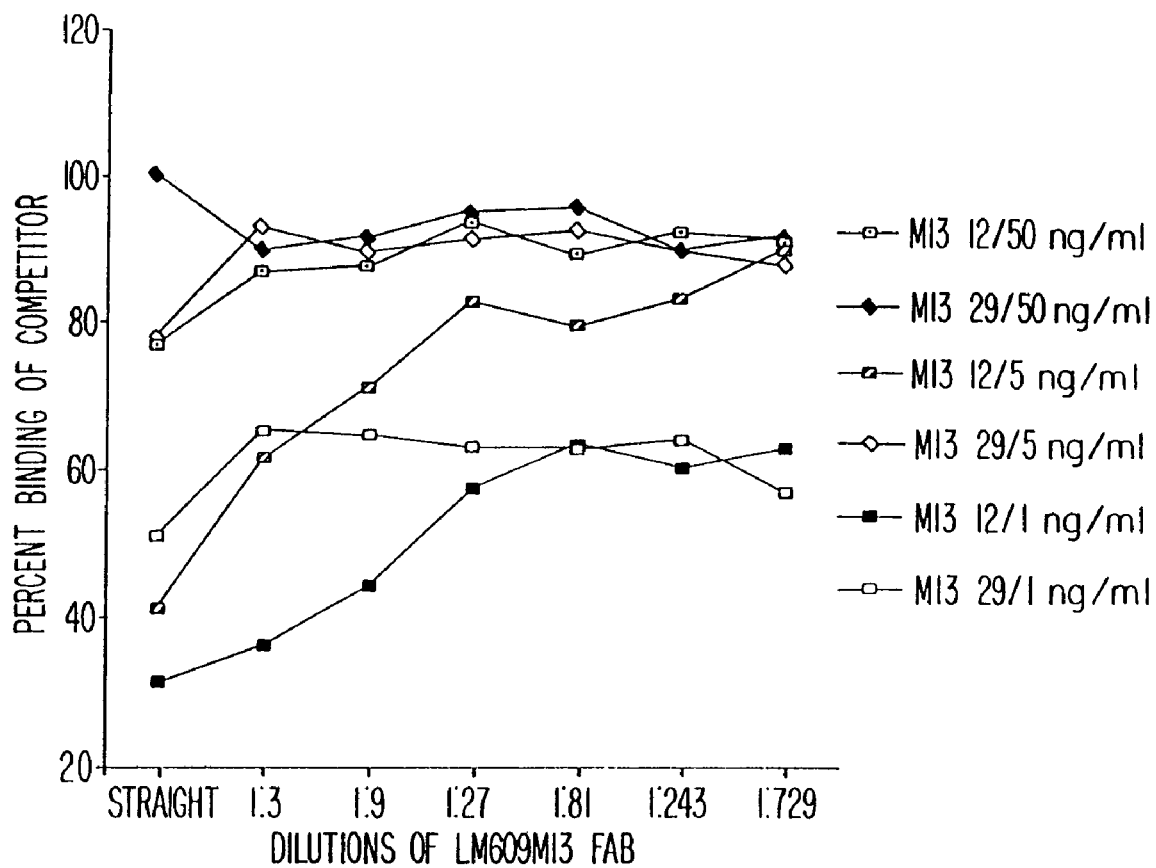
FIG. 3 shows the competitive inhibition of LM609 IgG binding to the integrin $\alpha_v\beta_3$ with recombinant LM609 Fab. Soluble recombinant murine LM609 Fab fragments were prepared from periplasmic fractions of M13 bacteriophage clones muLM609M13 12 and muLM609M13 29. The periplasm samples were serially diluted, mixed with either 1 ng/ml, 5 ng/ml, or 50 ng/ml of LM609 IgG and then incubated in 96 well plates coated with purified $\alpha_v\beta_3$. Plates were washed and bound LM609 IgG detected with goat anti-murine Fc specific antibody conjugated to alkaline phosphatase. Fab produced by clone muLM609M13 12 inhibits both 1 ng/ml and 5 ng/ml LM609 IgG binding at all concentrations of Fab greater than 1:27 dilution.

The invention is directed to nucleic acids encoding the monoclonal antibody (MAb) LM609. This antibody specifically recognizes the integrin $\alpha_v\beta_3$ and inhibits its functional activity. The invention is also directed to nucleic acids encoding and to polypeptides comprising non-murine grafted forms of LM609. These grafted antibodies retain the binding specificity and inhibitory activity of the parent murine antibody LM609. The invention is additionally directed to optimized forms of LM609 grafted antibodies that exhibit increased binding affinity and specificity compared to the non-mouse parental forms of the LM609 grafted antibody.

In one embodiment, the hybridoma expressing LM609 was used as a source to generate and clone cDNAs encoding LM609. The heavy and light chain encoding cDNAs were sequenced and their CDR regions were substituted into a human antibody framework to generate the non-murine form of the antibody. The substitution or grafting of the CDRs was performed by codon-based mutagenesis to generate a combinatorial antibody Fab library consisting of members that presented alternative residues at certain positions. Screening of the library resulted in the isolation of Vitaxin. As a grafted antibody containing human framework sequences, it is unlikely that Vitaxin will elicit a host immune response and can therefore be advantageously used for the treatment of $\alpha_v\alpha_3$-mediated diseases.

As used herein, the term "monoclonal antibody LM609" or "LM609" is intended to mean the murine monoclonal antibody specific for the integrin $\alpha_v\beta_3$ which is described by Cheresh, D. A. Proc. Natl, Acad. Sci. USA 84:6471-6475 (1987) and by Cheresh and Spiro J. Biol. Chem. 262:17703-17711 (1987). LM609 was produced against and is reactive with the M21 cell adhesion receptor now known as the integrin $\alpha_v\beta_3$. LM609 inhibits the attachment of M21 cells to $\alpha_v\beta_3$ ligands such as vitronectin, fibrinogen and von Willebrand factor (Cheresh and Spiro, supra) and is also an inhibitor of $\alpha_v\beta_3$-mediated pathologies such as tumor induced angiogenesis (Brooks et al. Cell 79:1157-1164 (1994), granulation tissue development in cutaneous wound (Clark et al., Am. J. Pathology, 148:1407-1421 (1996)) and smooth muscle cell migration such as that occurring during restenosis (Choi et al., J. Vascular Surg., 19:125-134 (1994); Jones et al., Proc. Natl. Acad. Sci. 93:2482-2487 (1996)).

As used herein, the term "Vitaxin" or Vitaxin™ is intended to refer to a non-mouse antibody or functional fragment thereof having substantially the same heavy and light chain CDR amino acid sequences as found in LM609. The term "Vitaxin" when used in reference to heavy or light chain polypeptides is intended to refer to a non-mouse heavy or light chain or functional fragment thereof having substantially the same heavy or light chain CDR amino acid sequences as found in the heavy or light chain of LM609, respectively. When used in reference to a functional fragment, not all LM609 CDRs need to be represented. Rather, only those CDRs that would normally be present in the antibody portion that corresponds to the functional fragment are intended to be referenced as the LM609 CDR amino acid sequences in the Vitaxin functional fragment. Similarly, the use of the term "Vitaxin" in reference to an encoding nucleic acid is intended to refer to a nucleic acid encoding a non-mouse antibody or functional fragment having substantially the same nucleotide sequence as the heavy and light chain CDR nucleotide sequences and encoding substantially the same CDR amino acid sequences as found in LM609.

As used herein, the term "LM609 grafted antibody" is intended to refer to a non-mouse antibody or functional fragment thereof having substantially the same heavy and light chain CDR amino acid sequences as found in LM609 and absent of the substitution of LM609 amino acid residues outside of the CDRs as defined by Kabat et al., U.S. Dept. of Health and Human Services, "Sequences of Proteins of Immunological Interest" (1983). The term "LM609 grafted antibody" or "LM609 grafted" when used in reference to heavy or light chain polypeptides is intended to refer to a non-mouse heavy or light chain or functional fragment thereof having substantially the same heavy or light chain CDR amino acid sequences as found in the heavy or light chain of LM609, respectively, and also absent of the substitution of LM609 residues outside of the CDRs as defined by Kabat et al., supra. When used in reference to a functional fragment, not all LM609 CDRs need to be represented. Rather, only those CDRs that would normally be present in the antibody portion that corresponds to the functional fragment are intended to be referenced as the LM609 CDR amino acid sequences in the LM609 grafted functional fragment. Similarly, the term "LM609 grafted antibody" or "LM609 grafted" used in reference to an encoding nucleic acid is intended to refer to a nucleic acid encoding a non-mouse antibody or functional fragment being absent of the substitution of LM609 amino acids outside of the CDRs as defined by Kabat et al., supra and having substantially the same nucleotide sequence as the heavy and light chain CDR nucleotide sequences and encoding substantially the same CDR amino acid sequences as found in LM609 and as defined by Kabat et al., supra.

The term "grafted antibody" or "grafted" when used in reference to heavy or light chain polypeptides or functional fragments thereof is intended to refer to a heavy or light chain or functional fragment thereof having substantially the same heavy or light chain CDR of a donor antibody, respectively, and also absent of the substitution of donor amino acid residues outside of the CDRs as defined by Kabat et al., supra. When used in reference to a functional fragment, not all donor CDRs need to be represented. Rather, only those CDRs that would normally be present in the antibody portion that corresponds to the functional fragment are intended to be referenced as the donor CDR amino acid sequences in the functional fragment. Similarly, the term "grafted antibody" or "grafted" when used in reference to an encoding nucleic acid is intended to refer to a nucleic acid encoding an antibody or functional fragment, being absent of the substitution of donor amino acids outside of the CDRs as defined by Kabat et al., supra and having substantially the same nucleotide sequence as the heavy and light chain CDR nucleotide sequences and encoding substantially the same CDR amino acid sequences as found in the donor antibody and as defined by Kabat et al., supra.

The meaning of the above terms are intended to include minor variations and modifications of the antibody so long as its function remains uncompromised. Functional fragments such as Fab, F(ab)$_2$, Fv, single chain Fv (scFv) and the like are similarly included within the definition of the terms LM609 and Vitaxin. Such functional fragments are well known to those skilled in the art. Accordingly, the use of these terms in describing functional fragments of LM609 or the Vitaxin antibody are intended to correspond to the definitions well known to those skilled in the art. Such terms are described in, for example, Harlow and Lane, *Antibodies: A Laboratory Manual*, Cold Spring Harbor Laboratory, New York (1989); *Molec. Biology and Biotechnology: A Comprehensive Desk Reference* (Myers, R. A. (ed.), New York: VCH Publisher, Inc.); Huston et al., *Cell Biophysics*, 22:189-224 (1993); Pluckthun and Skerra, *Meth. Enzymol.*, 178:497-515 (1989) and in Day, E. D., *Advanced Immunochemistry*, Second Ed., Wiley-Liss, Inc., New York, N.Y. (1990).

As with the above terms used for describing functional fragments of LM609, Vitaxin and a LM609 grafted antibody, the use of terms which reference other LM609, Vitaxin or LM609 grafted antibody domains, functional fragments, regions, nucleotide and amino acid sequences and polypeptides or peptides, is similarly intended to fall within the scope of the meaning of each term as it is known and used within the art. Such terms include, for example, "heavy chain polypeptide" or "heavy chain", "light chain polypeptide" or "light chain", "heavy chain variable region" ($V_H$) and "light chain variable region" ($V_L$) as well as the term "complementarity determining region" (CDR).

In the case where there are two or more definitions of a term which is used and/or accepted within the art, the definition of the term as used herein is intended to include all such meanings unless explicitly stated to the contrary. A specific example is the use of the term "CDR" to describe the non-contiguous antigen combining sites found within the variable region of both heavy and light chain polypeptides. This particular region has been described by Kabat et al., supra, and by Chothia et al., *J. Mol. Biol.* 196:901-917 (1987) and by MacCallum et al., *J. Mol. Biol.* 262:732-745 (1996) where the definitions include overlapping or subsets of amino acid residues when compared against each other. Nevertheless, application of either definition to refer to a CDR of LM609, Vitaxin, LM609 grafted antibodies or variants thereof is intended to be within the scope of the term as defined and used herein. The amino acid residues which encompass the CDRs as defined by each of the above cited references are set forth below in Table 1 as a comparison.

TABLE 1

CDR Definitions

|  | Kabat[1] | Chothia[2] | MacCallum[3] |
| --- | --- | --- | --- |
| $V_H$ CDR1 | 31-35 | 26-32 | 30-35 |
| $V_H$ CDR2 | 50-65 | 53-55 | 47-58 |
| $V_H$ CDR3 | 95-102 | 96-101 | 93-101 |
| $V_L$ CDR1 | 24-34 | 26-32 | 30-36 |
| $V_L$ CDR2 | 50-56 | 50-52 | 46-55 |
| $V_L$ CDR3 | 89-97 | 91-96 | 89-96 |

[1]Residue numbering follows the nomenclature of Kabat et al., supra
[2]Residue numbering follows the nomenclature of Chothia et al., supra
[3]Residue numbering follows the nomenclature of MacCallum et al., supra As used herein, the term "substantially" or "substantially the same" when used in reference to a nucleotide or amino acid sequence is intended to mean that the nucleotide or amino acid sequence shows a considerable degree, amount or extent of sequence identity when compared to a reference sequence. Such considerable degree, amount or extent of sequence identity is further considered to be significant and meaningful and therefore exhibit characteristics which are definitively recognizable or known. Thus, a nucleotide sequence which is substantially the same nucleotide sequence as a heavy or light chain of LM609, Vitaxin, or a LM609 grafted antibody including fragments thereof, refers to a sequence which exhibits characteristics that are definitively known or recognizable as encoding or as being the amino acid sequence of LM609, Vitaxin or a LM609 grafted antibody. Minor modifications thereof are included so long as they are recognizable as a LM609, Vitaxin or a LM609 grafted antibody sequence. Similarly, an amino acid sequence which is substantially the same amino acid sequence as a heavy or light chain of Vitaxin, a LM609 grafted antibody or functional fragment thereof, refers to a sequence which exhibits characteristics that are definitively known or recognizable as representing the amino acid sequence of Vitaxin or a LM609 grafted antibody and minor modifications thereof.

When determining whether a nucleotide or amino acid sequence is substantially the same as Vitaxin or a LM609 grafted antibody, consideration is given to the number of changes relative to the Vitaxin or LM609 grafted antibody together with whether the function is maintained. For example, a single amino acid change in a 3 amino acid CDR or several changes in a 16 amino acid CDR are considered to be substantially the same if $\alpha_v\beta_3$ binding function is maintained. Thus, a nucleotide or amino acid sequence is substantially the same if it exhibits characteristics that are definitively known or recognizable as representing the nucleotide or amino acid sequence of Vitaxin or a LM609 grafted antibody and minor modifications thereof as long as Vitaxin or LM609 grafted antibody function is maintained.

As used herein, the term "fragment" when used in reference to a nucleic acid encoding LM609, Vitaxin or a LM609 grafted antibody is intended to mean a nucleic acid having substantially the same sequence as a portion of a nucleic acid encoding LM609, Vitaxin or a LM609 grafted antibody. The nucleic acid fragment is sufficient in length and sequence to selectively hybridize to an LM609, a Vitaxin or a LM609 grafted antibody encoding nucleic acid or a nucleotide sequence that is complementary to an LM609, Vitaxin or LM609 grafted antibody encoding nucleic acid. Therefore, fragment is intended to include primers for sequencing and polymerase chain reaction (PCR) as well as probes for nucleic acid blot or solution hybridization. The meaning of the term is also intended to include regions of nucleotide sequences that do not directly encode LM609 polypeptides such as the introns, and the untranslated region sequences of the LM609 encoding gene.

As used herein, the term "functional fragment" when used in reference to Vitaxin, to a LM609 grafted antibody or to heavy or light chain polypeptides thereof is intended to refer to a portion of Vitaxin or a LM609 grafted antibody including heavy or light chain polypeptides which still retains some or all or the $\alpha_v\beta_3$ binding activity, $\alpha_v\beta_3$ binding specificity and/or integrin $\alpha_v\beta_3$-inhibitory activity. Such functional fragments can include, for example, antibody functional fragments such as Fab, F(ab)$_2$, Fv, single chain Fv (scFv). Other functional fragments can include, for example, heavy or light chain polypeptides, variable region polypeptides or CDR polypeptides or portions thereof so long as such functional fragments retain binding activity, specificity or inhibitory activity. The term is also intended to include polypeptides encompassing, for example, modified forms of naturally occurring amino acids such as D-stereoisomers, non-naturally occurring amino acids, amino acid analogues and mimetics so long as such polypeptides retain functional activity as defined above.

As used herein, the term "enhanced" when used in reference to Vitaxin, a LM609 grafted antibody or a functional fragment thereof is intended to mean that a functional characteristic of the antibody has been altered or augmented compared to a reference antibody so that the antibody exhibits a desirable property or activity. An antibody exhibiting enhanced activity can exhibit, for example, higher affinity or lower affinity binding, or increased or decreased association or dissociation rates compared to a reference antibody. An antibody exhibiting enhanced activity can also exhibit increased stability such as increased half-life in a particular organism. For example, an antibody activity can be enhanced to increase stability by decreasing susceptibility to proteolysis. If enhanced activity such as higher affinity binding or increased stability is desired, mutations can be introduced into framework or CDR amino acid residues and the resulting antibody variants screened for higher affinity binding to $\alpha_v\alpha_3$ or increased stability relative to a reference antibody such as the LM609 grafted parent antibody. An antibody exhibiting enhanced activity can also exhibit lower affinity binding, including decreased association rates or increased dissociation rates, if desired. An enhanced antibody exhibiting lower affinity binding is useful, for example, for penetrating a solid tumor. In contrast to a higher affinity antibody, which would bind to the peripheral regions of the tumor but would be unable to penetrate to the inner regions of the tumor due to its high affinity, a lower affinity antibody would be advantageous for penetrating the inner regions of the tumor.

The invention provides a nucleic acid encoding a heavy chain polypeptide for Vitaxin or a functional fragment thereof. Also provided is a nucleic acid encoding a light chain polypeptide for Vitaxin or a functional fragment thereof. The nucleic acids consist of substantially the same heavy or light chain variable region nucleotide sequences as those shown in FIGS. 1A and 1B (SEQ ID NOS:1 and 3, respectively) or a fragment thereof.

Vitaxin, including functional fragments thereof, is a non-mouse antibody which exhibits substantially the same binding activity, binding specificity and inhibitory activity as LM609. The Vitaxin Fv Fragment was produced by functionally replacing CDRs within human heavy and light chain variable region polypeptides with the CDRs derived from LM609. Functional replacement of the CDRs was performed by recombinant methods known to those skilled in the art. Such methods are commonly referred to as CDR grafting and are the subject matter of U.S. Pat. No. 5,225,539. Such methods can also be found described in "Protein Engineering of Antibody Molecules for Prophylactic and Therapeutic Applications in Man," Clark, M. (ed.), Nottingham, England: Academic Titles (1993).

Briefly, LM609 nucleic acid fragments having substantially the same nucleotide and encoding substantially the same amino acid sequence of each of the heavy and light chain CDRs were synthesized and substituted into each of the respective human chain encoding nucleic acids. To maintain functionality of the newly derived Vitaxin antibody, modifications were performed within the non-CDR framework region. These individual changes were made by generating a population of CDR grafted heavy and light chain variable regions wherein all possible changes outside of the CDRs were represented and then selecting the appropriate antibody by screening the population for binding activity. This screen resulted in the selection of the Vitaxin antibody described herein.

The nucleotide sequences of the Vitaxin heavy and light chain variable regions are shown in FIGS. 1A and 1B, respectively. These sequences correspond substantially to those that encode the heavy and light chain variable region polypeptides of Vitaxin. These Vitaxin nucleic acids are intended to include both the sense and anti-sense strands of the Vitaxin encoding sequences. Single- and double-stranded nucleic acids are similarly included as well as non-coding portions of the nucleic acid such as introns, 5'- and 3'-untranslated regions and regulatory sequences of the gene for example.

As shown in FIG. 1A, the Vitaxin heavy chain variable region polypeptide is encoded by a nucleic acid of about 351 nucleotides in length which begins at the amino terminal Gln1 residue of the variable region through to Ser117. This Vitaxin heavy chain variable region encoding nucleic acid is joined to a human IgG1 constant region to yield a coding region of 1431 nucleotides which encodes a heavy chain polypeptide of 477 total amino acids. Shown in FIG. 1B is the Vitaxin light chain variable region polypeptide which is encoded by a nucleic acid of about 321 nucleotides in length beginning at the amino terminal Glu1 residue of the variable region through to Lys107. This Vitaxin light chain variable region nucleic acid is joined to a human kappa construct region to yield a coding region of 642 nucleotides which code for a light chain polypeptide of 214 total amino acids.

Minor modification of these nucleotide sequences are intended to be included as heavy and light chain Vitaxin encoding nucleic acids and their functional fragments. Such minor modifications include, for example, those which do not change the encoded amino acid sequence due to the degeneracy of the genetic code as well as those which result in only a conservative substitution of the encoded amino acid sequence. Conservative substitutions of encoded amino acids include, for example, amino acids which belong within the following groups: (1) non-polar amino acids (Gly, Ala, Val, Leu, and Ile); (2) polar neutral amino acids (Cys, Met, Ser, Thr, Asn, and Gln); (3) polar acidic amino acids (Asp and Glu); (4) polar basic amino acids (Lys, Arg and His); and (5) aromatic amino acids (Phe, Trp, Tyr, and His). Other minor modifications are included within the nucleic acids encoding Vitaxin heavy and light chain polypeptides so long as the nucleic acid or encoded polypeptides retain some or all of their function as described herein.

Thus, the invention also provides a nucleic acid encoding a Vitaxin heavy chain or functional fragment thereof wherein the nucleic acid encodes substantially the same heavy chain variable region amino acid sequence of Vitaxin as that shown in FIG. 1A (SEQ ID NO:2) or a fragment thereof. Similarly, the invention also provides a nucleic acid encoding a Vitaxin light chain or functional fragment thereof wherein the nucleic acid encodes substantially the same light chain variable region amino acid sequence of Vitaxin as that shown in FIG. 1B (SEQ ID NO:4) or a fragment thereof.

In addition to conservative substitutions of amino acids, minor modifications of the Vitaxin encoding nucleotide sequences which allow for the functional replacement of amino acids are also intended to be included within the definition of the term. The substitution of functionally equivalent amino acids encoded by the Vitaxin nucleotide sequences is routine and can be accomplished by methods known to those skilled in the art. Briefly, the substitution of functionally equivalent amino acids can be made by identifying the amino acids which are desired to be changed, incorporating the changes into the encoding nucleic acid and then determining the function of the recombinantly expressed and modified Vitaxin polypeptide or polypeptides. Rapid methods for making and screening multiple simultaneous changes are well known within the art and can be used to produce a library of encoding nucleic acids which contain all possible or all desired changes and then expressing and screening the library for Vitaxin polypeptides which retain function. Such methods include, for example, codon based mutagenesis, random oligonucleotide synthesis and partially degenerate oligonucleotide synthesis.

Codon based mutagenesis is the subject matter of U.S. Pat. Nos. 5,264,563 and 5,523,388 and is advantageous for the above procedures since it allows for the production of essentially any and all desired frequencies of encoded amino acid residues at any and all particular codon positions within an oligonucleotide. Such desired frequencies include, for example, the truly random incorporation of all twenty amino acids or a specified subset thereof as well as the incorporation of a predetermined bias of one or more particular amino acids so as to incorporate a higher or lower frequency of the biased residues compared to other incorporated amino acid residues. Random oligonucleotide synthesis and partially degenerate oligonucleotide synthesis can similarly be used for producing and screening for functionally equivalent amino acid changes. However, due to the degeneracy of the genetic code, such methods will incorporate redundancies at a desired amino acid position. Random oligonucleotide synthesis is the coupling of all four nucleotides at each nucleotide position within a codon whereas partially degenerate oligonucleotide synthesis is the coupling of equal portions of all four nucleotides at the first two nucleotide positions, for example, and equal portions of two nucleotides at the third position. Both of these latter synthesis methods can be found described in, for example, Cwirla et al., *Proc. Natl. Acad. Sci. USA* 87:6378-6382, (1990) and Devlin et al., *Science* 249:404-406, (1990).

Identification of amino acids to be changed can be accomplished by those skilled in the art using current information available regarding the structure and function of antibodies as well as available and current information encompassing methods for CDR grafting procedures. For example, CDRs can be identified within the donor antibody by any or all of the criteria specified in Kabat et al., supra, Chothia et al., supra, and/or MacCallum et al., supra, and any or all non-identical amino acid residues falling outside of these CDR sequences can be changed to functionally equivalent amino acids. Using the above described methods known within the art, any or all of the non-identical amino acids can be changed either alone or in combination with amino acids at different positions to incorporate the desired number of amino acid substitutions at each of the desired positions. The Vitaxin polypeptides containing the desired substituted amino acids are then produced and screened for retention or augmentation of function compared to the unsubstituted Vitaxin polypeptides. Production of the substituted Vitaxin polypeptides can be accomplished by, for example, recombinant expression using methods known to those skilled in the art. Those Vitaxin polypeptides which exhibit retention or augmentation of function compared to unsubstituted Vitaxin are considered to contain minor modifications of the encoding nucleotide sequence which result in the functional replacement of one or more amino acids.

The functional replacement of amino acids is beneficial when producing grafted antibodies having human framework sequences since it allows for the rapid identification of equivalent amino acid residues without the need for structural information or the laborious procedures necessary to assess and identify which amino acid residues should be considered for substitution in order to successfully transfer binding function from the donor. Moreover, it eliminates the actual stepwise procedures to change and test the amino acids identified for substitution. Essentially, using the functional replacement approach described above, all non-identical amino acid residues between the donor and the human framework can be identified and substituted with any or all other possible amino acid residues at each non-identical position to produce a population of substituted polypeptides containing all possible or all desired permutations and combinations. The population of substituted polypeptides can then be screened for those substituted polypeptides which retain function. Using the codon based mutagenesis procedures described above, the generation of a library of substituted amino acid residues and the screening of functionally replaced residues has been used for the rapid production of grafted therapeutic antibodies as well as for the rapid alteration of antibody affinity. Such procedures are exemplified in, for example, Rosok et al.; *J. Biol. Chem.* 271:22611-22618 (1996) and in Glaser et al., *J. Immunol.* 149:3903-3913 (1992), respectively.

In addition to framework residues, amino acids in one or more CDRs can be functionally replaced to allow identification of a modified LM609 grafted antibody having enhanced activity. Using the methods described above for framework residues, amino acid substitutions can similarly be introduced into one or more CDRs in an LM609 grafted antibody. The modified LM609 grafted antibody can be tested for binding activity to determine whether $\alpha_v\beta_3$ binding activity is maintained. The modified LM609 grafted antibody can be further tested to determine if activity has been enhanced. Functional replacement of amino acid residues in one or more CDRs therefore allows the identification of an enhanced LM609 grafted antibody having a desirable property such as enhanced activity.

To generate modified LM609 grafted antibodies and select those with enhanced activity, several approaches can be employed in the selection of the number of residues within a CDR to mutate as well as the number of CDRs within a LM609 grafted antibody to modify. The choice of selection criteria for mutagenesis of CDRs will depend on the need and desired application of the enhanced antibody. For example, one or a few amino acid positions within a single CDR can be modified to contain selected amino acids at that position. Alternatively, the targeted amino acid positions can be modified to contain all possible amino acids at that position. The resultant population of modified antibodies can then be screened for enhanced activity.

The construction of modified LM609 grafted antibody populations can also be made where all amino acids positions within a CDR have been mutated to contain all possible amino acids and where amino acid positions within multiple CDRs have been modified to contain variant amino acid residues. In this way, populations can be constructed which range from 2 to >$10^7$ unique members. The larger the population, the more efficient will be the selection of an enhanced LM609 grafted antibody since there will be a larger number of different antibodies within the population. However, a small population of modified LM609 grafted antibodies can be made and successfully used for the selection of enhanced LM609 grafted antibodies. The size of the population of modified LM609 grafted antibodies will depend on the need of a particular application and can be determined by one skilled in the art.

The generation of modified LM609 grafted antibodies can be achieved by introducing amino acid substitutions into one or more CDRs of an LM609 grafted antibody. For example, single amino acid substitutions can be systematically introduced into a CDR by changing a given amino acid in the CDR to any or all amino acids. Amino acid substitutions can also be introduced into all amino acid positions in one or more of the CDRs or in all of the CDRs, generating a population of modified LM609 grafted antibody variants. This population of modified LM609 grafted antibody variants having single amino acid substitutions can be screened to identify those variants that maintain $\alpha_v\beta_3$ binding activity. The variants having $\alpha_v\beta_3$ binding activity can be further characterized to identify those variants having enhanced activity. Such a systematic approach to introducing single amino acid substitutions and generating a population of LM609 grafted antibody variants to screen for enhanced LM609 grafted antibodies having high affinity binding to $\alpha_v\beta_3$ is described in Example VI.

In addition to generating a population of modified LM609 grafted antibody variants, a particular CDR or a particular amino acid in a CDR can be selected to introduce one or more amino acid substitutions. For example, sequence homology or a structural model can be used to identify particular amino acid positions to introduce amino acid substitutions. In this example, only one or a few modified LM609 grafted antibody variants are generated and screened for binding activity to $\alpha_v\alpha_3$. One of skill in the art will know or can determine whether it is desirable to generate a large population of modified LM609 grafted antibody variants or to generate a limited number of modified LM609 grafted antibody variants to screen and identify an enhanced LM609 grafted antibody having enhanced activity.

In addition to identifying enhanced LM609 grafted antibodies by generating a population of modified LM609 grafted antibodies having single amino acid substitutions in a CDR and screening for enhanced activity, enhanced LM609 grafted antibody variants can also be generated by combining two or more mutations, each known to independently result in enhanced activity, into a single antibody. When there are more than two mutations, an efficient way to identify combinations of mutations which further augment activity is to construct all possible combinations and permutations and then select for those with enhanced activity. For example, two single mutations in one or more CDRs can be combined to generate a new modified LM609 grafted antibody having two CDR mutations and screened to determine if the $\alpha_v\beta_3$ binding activity is increased over that of the single mutants. Similarly, three mutations can be combined and the resulting modified LM609 grafted antibody screened for enhanced binding activity. Using such an approach of combining CDR mutations, a new population of modified LM609 grafted antibody variants can be generated by incorporating all combinations of the single CDR mutations resulting in enhanced activity into new modified LM609 grafted antibody variants and screening to obtain an optimized enhanced LM609 grafted antibody.

An iterative, step-wise approach to identifying an enhanced LM609 grafted antibody is advantageous in that it allows the identification of an antibody having optimal binding activity without the need to generate and screen a large number of modified LM609 grafted antibody variants. For example, using the approach described in Examples VI and VII in which single mutants were identified and combined into a new population of LM609 grafted antibody variants, enhanced LM609 grafted antibodies having higher affinity were identified by generating 2592 unique variants. In contrast, complete randomization of a single eight amino acid residue CDR would require >$10^{10}$ unique variants. Therefore, such an iterative approach allows identification of enhanced LM609 grafted antibodies having enhanced activity such as high affinity binding by generating a relatively small number of unique modified LM609 grafted antibody variants and screening and identifying those enhanced LM609 grafted antibody variants exhibiting high affinity binding.

An iterative, step-wise approach to identifying enhanced LM609 variants can also be performed using additional steps. Instead of generating all combinations of single amino acid mutations, the single amino acid mutations can be combined in pairs to generate all combinations of double mutants and screened for activity. Those double mutants having enhanced activity can be combined with any or all single mutants to generate triple mutants that are screened for enhanced binding activity. Each iterative round of generating modified LM609 grafted antibody variants can incorporate additional single mutations, and the resulting modified LM609 grafted antibodies can be screened for enhanced activity. The stepwise generation of LM609 grafted antibody variants can thus be used to identify an optimized LM609 grafted antibody. Additionally, such an iterative approach also allows for the identification of numerous enhanced antibodies which exhibit a range of different, enhanced binding activities.

An optimized LM609 grafted antibody can also be referred to as an LM609-like grafted antibody or an $\alpha_v\beta_3$-specific grafted antibody and is recognizable because the antibody or functional fragments thereof retains the functional characteristics of LM609. For example, enhanced LM609 grafted antibody variants, which have a single amino acid substitution and have enhanced activity, can be identified and correlated with a specific amino acid substitution. These amino acid substitutions can be combined to generate a new modified LM609 grafted antibody that is tested for activity. Such a combination of advantageous CDR amino acid substitutions can result in an optimized LM609 grafted antibody with multiple CDRs having at least one amino acid substitution or a single CDR having multiple amino acid substitutions, where the modified LM609 grafted antibody has enhanced activity.

Enhanced LM609 grafted antibodies, particularly those optimized by functional replacement of amino acid residues in the CDRs, have desirable enhanced properties such as increased affinity. For example, an optimized LM609 grafted antibody having increased affinity will have higher affinity than the parent antibody used for introducing functional replacement of amino acids. Higher affinity is determined relative to a reference antibody having a similar structure. For example, if the optimized LM609 grafted antibody is an intact antibody containing two heavy chains and two light chains, then higher affinity is determined relative to the intact parent LM609 grafted antibody. Similarly, if the optimized LM609 grafted antibody is an Fab, then higher affinity is determined relative to the Fab of the parent LM609 grafted antibody.

Although it is not necessary to proceed through multiple optimization steps to obtain a high affinity LM609 grafted antibody, in general, the increase in affinity can correlate with the number of modifications within and between CDRs as well as with the number of optimization steps. Therefore, LM609 grafted antibodies will exhibit a variety of ranges. For example, LM609 grafted antibodies having enhanced affinity will have up to about 2-fold higher affinity or greater, generally greater than about 2- to 5-fold higher affinity such as greater than about 4- to 5-fold higher affinity or about 5- to 10-fold higher affinity than the reference antibody. Particularly, a LM609 grafted antibody having enhanced affinity will have greater than about 10- to 50-fold higher affinity, greater than about 50-fold higher affinity, or greater than about 100-fold higher affinity than the reference antibody.

As described above, functional replacement of CDR amino acid residues can be used to identify LM609 grafted antibodies exhibiting higher affinity than a parent LM609 grafted antibody. Methods discussed above or below for introducing minor modifications into Vitaxin or LM609 grafted antibody encoding nucleotide sequences can similarly be used to generate a library of modified LM609 grafted antibody variants, including methods such as codon based mutagenesis, random oligonucleotide synthesis and partially degenerate oligonucleotide synthesis. For example, codon based mutagenesis has been used to generate such a library of modified LM609 grafted antibody variants having single amino acid substitutions (see Example VI).

After generating a library of modified LM609 grafted antibody variants, the variants can be expressed and screened for binding activity to $\alpha_v\beta_3$. Methods well known to those skilled in the art related to determining antibody-antigen interactions are used to screen for modified LM609 grafted antibodies exhibiting binding activity to $\alpha_v\beta_3$ (Harlow and Lane, supra). For example, an ELISA method has been used to screen a library of modified LM609 grafted antibody variants to identify those variants that maintained $\alpha_v\beta_3$ binding activity (see Example VI). Only those modified LM609 grafted antibodies that maintain $\alpha_v\beta_3$ binding activity are considered for further characterization.

Modified LM609 grafted antibodies having $\alpha_v\beta_3$ binding activity can be further characterized to determine which modified LM609 grafted antibody has enhanced activity. The type of assay used to assess enhanced activity depends on the particular desired characteristic. For example, if altered binding activity is desired, then binding assays that allow determination of binding affinity are used. Such assays include binding assays, competition binding assays and surface plasmon resonance as described in Example VI.

Introduction of single amino acid substitutions into CDRs of LM609 grafted antibodies can be used to generate a library of modified LM609 grafted antibodies and screen for binding activity to $\alpha_v\alpha_3$. Those modified LM609 grafted antibodies exhibiting binding activity to $\alpha_v\alpha_3$ can then be further characterized to identify enhanced LM609 grafted antibodies exhibiting enhanced activity such as higher binding affinity. For example, using such an approach, a number of enhanced LM609 grafted antibodies having single amino acid substitutions were generated using the heavy chain variable region shown in FIG. 1a (SEQ ID NO:2) and the light chain variable region shown in FIG. 7 (SEQ ID NO:32), and LM609 grafted antibodies were identified displaying 2 to 13-fold improved affinity over the parent LM609 grafted antibody (see Example VI).

Following identification of enhanced LM609 grafted antibodies having a single amino acid substitution, the amino acid mutations can be combined to further enhance activity. Methods discussed above for introducing single amino acid substitutions into CDRs can similarly be applied to combine amino acid substitutions. For example, a combinatorial library of amino acid mutations that resulted in enhanced $\alpha_v\alpha_3$ binding affinity was generated using degenerate oligonucleotides and two site hybridization mutagenesis as described in Example VII. Enhanced LM609 grafted antibodies containing multiple CDR amino acid substitutions were generated using the heavy chain variable region shown in FIG. 1a (SEQ ID NO:2) and the light chain variable region shown in FIG. 7 (SEQ ID NO:32), and LM609 grafted antibodies were identified having 20-fold higher affinity to greater than 90-fold higher affinity than the parent LM609 grafted antibody.

In addition to combining CDR amino acid substitutions to generate an enhanced or optimized LM609 grafted antibody, CDR amino acid substitutions can also be combined with framework mutations that contribute desirable properties to a LM609 grafted antibody. Thus, mutations in CDR or framework regions that enhance activity can be combined to further optimize LM609 grafted antibodies.

The invention further provides fragments of Vitaxin heavy and light chain encoding nucleic acids wherein such fragments consist substantially of the same nucleotide or amino acid sequence as the variable region of Vitaxin heavy or light chain polypeptides. The variable region of the Vitaxin heavy chain polypeptide consists essentially of nucleotides 1-351 and of amino acid residues Gln1 to Ser117 of FIG. 1A (SEQ ID NOS:1 and 2, respectively). The variable region of the Vitaxin light chain polypeptide consists essentially of nucleotides 1-321 and of amino acid residues Glu1 to Lys107 of FIG. 1B (SEQ ID NOS:3 and 4, respectively). The termini of such variable region encoding nucleic acids is not critical so long as the intended purpose and function remains the same.

Fragments additional to the variable region nucleic acid fragments are provided as well. Such fragments include, for example, nucleic acids consisting substantially of the same nucleotide sequence as a CDR of a Vitaxin-heavy or light chain polypeptide. Sequences corresponding to the Vitaxin CDRs include, for example, those regions defined by Kabat et al., supra, and/or those regions defined by Chothia et al., supra, as well as those defined by MacCallum et al., supra. The Vitaxin CDR fragments for each of the above definitions correspond to the nucleotides set forth below in Table 2. The nucleotide sequence numbering is taken from the primary sequence shown in FIGS. 1A and 1B (SEQ ID NOS:1 and 3) and conforms to the definitions previously set forth in Table 1.

TABLE 2

Vitaxin CDR Nucleotide Residues

|  | Kabat | Chothia | MacCallum |
|---|---|---|---|
| $V_H$ CDR1 | 91-105 | 76-96 | 88-105 |
| $V_H$ CDR2 | 148-198 | 157-168 | 139-177 |
| $V_H$ CDR3 | 295-318 | 298-315 | 289-315 |
| $V_L$ CDR1 | 70-102 | 76-96 | 88-108 |
| $V_L$ CDR2 | 148-168 | 148-156 | 136-165 |
| $V_L$ CDR3 | 265-291 | 271-288 | 265-288 |

Similarly, the Vitaxin CDR fragments for each of the above definitions correspond to the amino acid residues set forth below in Table 3. The amino acid residue number is taken from the primary sequence shown in FIGS. 1A and 1B (SEQ ID NOS:2 and 4) and conforms to the definitions previously set forth in Table 1.

TABLE 3

Vitaxin CDR Amino Acid Residues

|  | Kabat | Chothia | MacCallum |
|---|---|---|---|
| $V_H$ CDR1 | Ser31-Ser35 | Gly26-Tyr32 | Ser30-Ser35 |
| $V_H$ CDR2 | Lys50-Gly66 | Ser53-Gly56 | Trp47-Tyr59 |
| $V_H$ CDR3 | His99-Tyr106 | Asn100-Ala105 | Ala97-Ala105 |
| $V_L$ CDR1 | Gln24-His34 | Ser26-His32 | Ser30-Tyr36 |
| $V_L$ CDR2 | Tyr50-Ser56 | Tyr50-Ser52 | Leu46-Ile55 |
| $V_L$ CDR3 | Gln89-Thr97 | Ser91-His96 | Gln89-His96 |

Thus, the invention also provides nucleic acid fragments encoding substantially the same amino acid sequence as a CDR of a Vitaxin heavy or light chain polypeptide.

Nucleic acids encoding Vitaxin heavy and light chain polypeptides and fragments thereof are useful for a variety of diagnostic and therapeutic purposes. For example, the Vitaxin nucleic acids can be used to produce Vitaxin antibodies and functional fragments thereof having binding specificity and inhibitory activity against the integrin $\alpha_v\alpha_3$. The antibody and functional fragments thereof can be used for the diagnosis or therapeutic treatment of $\alpha_v\alpha_3$-mediated disease. Vitaxin and functional fragments thereof can be used, for example, to inhibit binding activity or other functional activities of $\alpha_v\beta_3$ that are necessary for progression of an $\alpha_v\beta_3$-mediated disease. Other functional activities necessary for progression of $\alpha_v\beta_3$-mediated disease include, for example, the activation of $\alpha_v\beta_3$, $\alpha_v\beta_3$-mediated signal transduction and the $\alpha_v\beta_3$-mediated prevention of apoptosis. Advantageously, however, Vitaxin comprises non-mouse framework amino acid sequences and as such is less antigenic in regard to the induction of a host immune response. The Vitaxin nucleic acids of the inventions can also be used to model functional equivalents of the encoded heavy and light chain polypeptides.

Thus, the invention provides Vitaxin heavy chain and Vitaxin light chain polypeptides or functional fragments thereof. The Vitaxin heavy chain polypeptide exhibits substantially the same amino acid sequence as that shown in FIG. 1A (SEQ ID NO:2) or functional fragment thereof whereas the Vitaxin light chain polypeptide exhibits substantially the same amino acid sequence as that shown in FIG. 1B (SEQ ID NO:4) or functional fragment thereof. Also provided is a Vitaxin antibody or functional fragment thereof. The antibody is generated from the above heavy and light chain polypeptides or functional fragments thereof and exhibits selective binding affinity to $\alpha_v\beta_3$.

The invention provides a nucleic acid encoding a heavy chain polypeptide for a LM609 grafted antibody. Also provided is a nucleic acid encoding a light chain polypeptide for a LM609 grafted antibody. The nucleic acids consist of substantially the same heavy chain variable region nucleotide sequence as that shown in FIG. 1A (SEQ ID NO:1) and substantially the same light chain variable region nucleotide sequence as that shown in FIG. 7 (SEQ ID NO:31) or a fragment thereof.

LM609 grafted antibodies, including functional fragments thereof, are non-mouse antibodies which exhibit substantially the same binding activity, binding specificity and inhibitory activity as LM609. The LM609 grafted antibody Fv fragments described herein are produced by functionally replacing the CDRs as defined by Kabat et al., hereinafter referred to as "Kabat CDRs," within human heavy and light chain variable region polypeptides with the Kabat CDRs derived from LM609. Functional replacement of the Kabat CDRs is performed by the CDR grafting methods previously described and which is the subject matter of U.S. Pat. No. 5,225,539, supra. Substitution of amino acid residues outside of the Kabat CDRs can additionally be performed to maintain or augment beneficial binding properties so long as such amino acid substitutions do not correspond to a donor amino acid at that particular position. Such substitutions allow for the modulation of binding properties without imparting any mouse sequence characteristics onto the antibody outside of the Kabat CDRs. Although the production of such antibodies is described herein with reference to LM609 grafted antibodies, the substitution of such non-donor amino acids outside of the Kabat CDRs can be utilized for the production of essentially any grafted antibody. The production of LM609 grafted antibodies is described further below in Example V.

The nucleotide sequences of the LM609 grafted antibody heavy and light chain variable regions are shown in FIGS. 1A and 7, respectively. These sequences correspond substantially to those that encode the heavy and light chain variable region polypeptides of a LM609 grafted antibody. These nucleic acids are intended to include both the sense and anti-sense strands of the LM609 grafted antibody encoding sequences. Single- and double-stranded nucleic acids are similarly included as well as non-coding portions of the nucleic acid such as introns, 5'- and 3'-untranslated regions and regulatory sequences of the gene for example.

The nucleotide and amino acid residue boundaries for a LM609 grafted antibody are identical to those previously described for Vitaxin. For example, a LM609 grafted antibody heavy chain variable region polypeptide is encoded by a nucleic acid of about 351 nucleotides in length which begins at the amino terminal Gln1 residue of the variable region through to Ser17 (FIG. 1A, SEQ ID NOS:1 and 2, respectively). The LM609 grafted antibody light chain variable region polypeptide is encoded by a nucleic acid of about 321 nucleotides in length beginning at the amino terminal Glu1 residue of the variable region through to Lys107 (FIG. 7, SEQ ID NOS:31 and 32, respectively). As with Vitaxin, minor modification of these nucleotide sequences are intended to be included as heavy and light chain variable region encoding nucleic acids and their functional fragments.

Thus, the invention also provides a nucleic acid encoding a LM609 grafted antibody heavy chain wherein the nucleic acid encodes substantially the same heavy chain variable region amino acid sequence as that shown in FIG. 1A (SEQ ID NO:2) or fragment thereof. Similarly, the invention also provides a nucleic acid encoding a LM609 grafted antibody light chain wherein the nucleic acid encodes substantially the same light chain variable region amino acid sequence as that shown in FIG. 7 (SEQ ID NO:32) or fragment thereof.

In addition to conservative substitutions of amino acids, minor modifications of the LM609 grafted antibody encoding nucleotide sequences which allow for the functional replacement of amino acids are also intended to be included within the definition of the term. Identification of amino acids to be changed can be accomplished by those skilled in the art using current information available regarding the structure and function of antibodies as well as available and current information encompassing methods for CDR grafting procedures. The substitution of functionally equivalent amino acids encoded by the LM609 grafted antibody nucleotide sequences is routine and can be accomplished by methods known to those skilled in the art. As described previously, such methods include, for example, codon based mutagenesis, random oligonucleotide synthesis and partially degenerate oligonucleotide synthesis and are beneficial when producing grafted antibodies since they allow for the rapid identification of equivalent amino acid residues without the need for structural information.

The invention further provides fragments of LM609 grafted antibody heavy and light chain encoding nucleic acids wherein such fragments consist substantially of the same nucleotide or amino acid sequence as the variable region of a LM609 grafted antibody heavy or light chain polypeptide. As with Vitaxin, the termini of such variable region encoding nucleic acids is not critical so long as the intended purpose and function remains the same.

Fragments additional to the variable region nucleic acid fragments are provided as well and include, for example, nucleic acids consisting substantially of the same nucleotide sequence as a CDR of a LM609 grafted antibody heavy or light chain polypeptide. As with Vitaxin, sequences corresponding to the LM609 grafted antibody CDRs include, for example, those regions defined by Kabat et al., supra, Chothia et al., supra, as well as those defined by MacCallum et al., supra. The LM609 grafted antibody CDR regions will be similar to those described previously for Vitaxin. Moreover, such regions are well known and can be determined by those skilled in the art given the LM609 sequences and teachings provided herein. Thus, the invention also provides nucleic acid fragments encoding substantially the same amino acid sequence as a CDR of a LM609 grafted antibody heavy or light chain polypeptide.

As with Vitaxin, nucleic acids encoding LM609 grafted antibody heavy and light chain polypeptides and fragments thereof are useful for a variety of diagnostic and therapeutic purposes. For example, LM609 grafted antibody encoding nucleic acids can be used to produce recombinant antibodies and functional fragments thereof having binding specificity and inhibitory activity against the integrin $\alpha_v\alpha_3$. The antibody and functional fragments thereof can be used for the diagnosis or therapeutic treatment of $\alpha_v\beta_3$-mediated disease. Such diseases and methods of use for anti-$\alpha_v\beta_3$ antibodies have been described previously in reference to Vitaxin and are equally applicable to the LM609 grafted antibodies described herein.

Thus, the invention provides LM609 grafted antibody heavy chain and Vitaxin light chain polypeptides or functional fragments thereof. The LM609 grafted antibody heavy chain polypeptide exhibits substantially the same amino acid sequence as that shown in FIG. 1A (SEQ ID NO:2) or functional fragment thereof whereas the LM609 grafted antibody light chain polypeptide exhibits substantially the same amino acid sequence as that shown in FIG. 7 (SEQ ID NO:32). Also provided is a LM609 grafted antibody or functional fragment thereof. The antibody is generated from the above heavy and light chain polypeptides or functional fragments thereof and exhibits selective binding affinity to $\alpha_v\beta_3$.

The invention provides an enhanced LM609 grafted antibody exhibiting selective binding affinity to $\alpha_v\beta_3$. The enhanced LM609 grafted antibody contains at least one amino acid substitution in one or more CDRs of a LM609 grafted heavy chain variable region polypeptide or a LM609 grafted light chain variable region polypeptide, wherein the $\alpha_v\beta_3$ binding affinity of the enhanced LM609 grafted antibody is maintained or enhanced.

To identify enhanced LM609 grafted antibodies, a library of modified LM609 grafted antibodies was generated as described above and in Example VI. Initially, LM609 CDRs were identified and selected to introduce single amino acid substitutions. Utilizing the numbering system of Kabat et al., supra, the CDR residues selected for mutagenesis were $V_H$ CDR1 Gly-Phe-Thr-Phe-Ser-Ser-Tyr-Asp-Met-Ser (SEQ ID NO:34) (Gly$^{26}$-Ser$^{35}$); $V_H$ CDR2 Trp-Val-Ala-Lys-Val-Ser-Ser-Gly-Gly-Gly (SEQ ID NO:36) and Ser-Thr-Tyr-Tyr-Leu-Asp-Thr-Val-Gln-Gly (SEQ ID NO:38) (Trp$^{47}$-Gly$^{65}$); $V_H$ CDR3 Ala-Arg-His-Asn-Tyr-Gly-Ser-Phe-Ala-Tyr (SEQ ID NO:40) (Ala$^{93}$-Tyr$^{102}$); $V_L$ CDR1 Gln-Ala-Ser-Gln-Ser-Ile-Ser-Asn-His-Leu-His-Trp-Tyr (SEQ ID NO:42) (Gln$^{24}$-Tyr$^{36}$); $V_L$ CDR2 Leu-Leu-Ile-Arg-Tyr-Arg-Ser-Gln-Ser-Ile-Ser (SEQ ID NO:44) (Leu$^{46}$-Ser$^{56}$); and $V_L$ CDR3 Gln-Gln-Ser-Gly-Ser-Trp-Pro-His-Thr (SEQ ID NO:46) (Gln$^{89}$-Thr$^{97}$).

The nucleotide sequences encoding the CDR residues selected for mutagenesis were $V_H$ CDR1 GGA TTC ACC TTC AGT AGC TATGAC ATG TCT (SEQ ID NO:33); $V_H$ CDR2 TGG GTCGCA AAA GTT AGT AGT GGT GGT GGT (SEQ ID NO:35) and AGC ACC TAC TAT TTA GAC ACT GTG CAG GGC (SEQ ID NO:37); $V_H$ CDR3 GCA AGA CAT AAC TAC GGC AGT TTT GCT TAC (SEQ ID NO:39); $V_L$ CDR1 CAG GCC AGC CAA AGT ATT AGC AAC CAC CTA CAC TGG TAT (SEQ ID NO:41); $V_L$ CDR2 CTT CTC ATC CGT TAT CGT TCC CAG TCC ATC TCT (SEQ ID NO:43); and $V_L$ CDR3 CAA CAG AGT GGC AGC TGG CCT CAC ACG (SEQ ID NO:45).

Single amino acid substitutions can be introduced into the CDRs of an LM609 grafted antibody to generate a population of modified LM609 grafted antibodies. For example, every amino acid in one or more CDRs can be mutated to any or all amino acids to generate a population of modified LM609 grafted antibodies and the population screened for $\alpha_v\beta_3$ binding activity. Although this population is generated by mutating amino acids in CDRs, populations can also be constructed where changes are made in the framework region residues or in both the CDRs and the framework. Such mutations in the variable regions can be made separately, in combination, or step-wise. Thus, the invention also provides for an enhanced LM609 grafted antibody, where the amino acid substitution is in the CDR or in the framework region.

The invention additionally provides an enhanced LM609 grafted antibody exhibiting enhanced binding affinity. Enhanced LM609 grafted antibodies exhibiting enhanced binding affinity include those containing at least one of the following CDRs having single amino acid substitutions:

a $V_H$ CDR1 selected from the group consisting of Gly-Thr-Thr-Phe-Ser-Ser-Tyr-Asp-Met-Ser (SEQ ID NO:48), Gly-Phe-Thr-Trp-Ser-Ser-Tyr-Asp-Met-Ser (SEQ ID NO:50) and Gly-Phe-Thr-Phe-Leu-Ser-Tyr-Asp-Met-Ser (SEQ ID NO:52);

a $V_H$ CDR2 selected from the group consisting of Trp-Val-Ala-Lys-Val-Lys-Ser-Gly-Gly-Gly (SEQ ID NO:54), Ser-Thr-Tyr-Tyr-Pro-Asp-Thr-Val-Gln-Gly (SEQ ID NO:56) and Ser-Thr-Tyr-Tyr-Leu-Asp-Thr-Val-Glu-Gly (SEQ ID NO:58);

a $V_H$ CDR3 selected from the group consisting of Ala-Arg-His-Asn-His-Gly-Ser-Phe-Ala-Tyr (SEQ ID NO:60), Ala-Arg-His-Asn-Tyr-Gly-Ser-Tyr-Ala-Tyr (SEQ ID NO:62), Ala-Arg-His-Asn-Tyr-Gly-Ser-Phe-Asp-Tyr (SEQ ID NO:64), Ala-Arg-His-Asn-Tyr-Gly-Ser-Phe-Tyr-Tyr (SEQ ID NO:66), Ala-Arg-His-Asn-Tyr-Gly-Ser-Phe-Ala-Ser (SEQ ID NO:68), Ala-Arg-His-Asn-Tyr-Gly-Ser-Phe-Ala-Thr (SEQ ID NO:70), Ala-Arg-His-Asn-Tyr-Gly-Ser-Phe-Ala-Asp (SEQ ID NO:72), Ala-Arg-His-Asn-Tyr-Gly-Ser-Phe-Ala-Glu (SEQ ID NO:74), Ala-Arg-His-Asn-Tyr-Gly-Ser-Phe-Ala-Met (SEQ ID NO:76), Ala-Arg-His-Asn-Tyr-Gly-Ser-Phe-Ala-Gly (SEQ ID NO:78) and Ala-Arg-His-Asn-Tyr-Gly-Ser-Phe-Ala-Ala (SEQ ID NO:80); the $V_L$ CDR1 Gln-Ala-Ser-Gln-Ser-Ile-Ser-Asn-Phe-Leu-His-Trp-Tyr (SEQ ID NO:82); the $V_L$ CDR2 Leu-Leu-Ile-Arg-Tyr-Ser-Ser-Gln-Ser-Ile-Ser (SEQ ID NO:84); and a $V_L$ CDR3 selected from the group consisting of Gln-Gln-Ser-Asn-Ser-Trp-Pro-His-Thr (SEQ ID NO:86), Gln-Gln-Ser-Thr-Ser-Trp-Pro-His-Thr (SEQ ID NO:88), Gln-Gln-Ser-Gly-Ser-Trp-Pro-Leu-Thr (SEQ ID NO:90) and Gln-Gin-Ser-Gly-Ser-Trp-Pro-Gln-Thr (SEQ ID NO:92).

The nucleotide sequences encoding the CDRs having single amino acid substitutions were $V_H$ CDR1 GGA ACT ACC TTC AGT AGC TAT GAC ATG TCT (SEQ ID NO:47), GGA TTC ACC TGG AGT AGC TAT GAC ATG TCT (SEQ ID NO:49), and GGA TTC ACC TTC CTG AGC TAT GAC ATG TCT (SEQ ID NO:51); $V_H$ CDR2 TGG GTC GCA AAA GTT AAA AGT GGT GGT GGT (SEQ ID NO:53), AGC ACC TAC TAT CCT GAC ACT GTG. CAG GGC (SEQ ID NO:55), and AGC ACC TAC TAT TTA GAC ACT GTG GAG GGC (SEQ ID NO:57); $V_H$ CDR3 GCA AGA CAT AAC CAT GGC AGT TTT GCT TAC (SEQ ID NO:59), GCA AGA CAT AAC TAC GGC AGT TAT GCT TAC (SEQ ID NO:61), GCA AGA CAT AAC TAC GGC AGT TTT GAT TAC (SEQ ID NO:63), GCA AGA CAT AAC TAC GGC AGT TTT TAT TAC (SEQ ID NO:65), GCA AGA CAT AAC TAC GGC AGT TTT GCT TCT (SEQ ID NO:67), GCA AGA CAT AAC TAC GGC AGT TTT GCT ACT (SEQ ID NO:69), GCA AGA CAT AAC TAC GGC AGT TTT GCT GAT (SEQ ID NO:71), GCA AGA CAT AAC TAC GGC AGT TTT GCT GAA (SEQ ID NO:73), GCA AGA CAT AAC TAC GGC AGT TTT GCT ATG (SEQ ID NO:75), GCA AGA CAT AAC TAC GGC AGT TTT GCT GGG (SEQ ID NO:77), and GCA AGA CAT AAC TAC GGC AGT TTT GCT GCT (SEQ ID NO:79); $V_L$ CDR1 CAG GCC AGC CAA AGT ATT AGC AAC TTT CTA CAC TGG TAT (SEQ ID NO:81); $V_L$ CDR2 CTT CTC ATC CGT TAT TCT TCC CAG TCC ATC TCT (SEQ ID NO:83); and $V_L$ CDR3 CAA CAG AGT AAT AGC TGG CCT CAC ACG (SEQ ID NO:85), CAA CAG AGT ACT AGC TGG CCT CAC ACG (SEQ ID NO:87), CAA CAG AGT GGC AGC TGG CCT CTG ACG (SEQ ID NO:89) and CAA CAG AGT GGC AGC TGG CCT CAG ACG (SEQ ID NO:91).

Enhanced LM609 grafted antibodies having CDRs with single amino acid substitutions and higher affinity binding than the parent LM609 grafted antibody can also be identified, where the corresponding amino acid mutations are combined to generate new modified LM609 grafted antibodies. Identification is performed by screening for $\alpha_v\beta_3$ binding activity. In some combinations, the LM609 grafted antibody will comprise at least one CDR having two or more amino acid substitutions. The invention provides an enhanced LM609 grafted antibody containing at least one of the following CDRs containing multiple amino acid substitutions: a $V_H$ CDR3 selected from the group consisting of Ala-Arg-His-Asn-His-Gly-Ser-Phe-Ala-Ser (SEQ ID NO:94); Ala-Arg-His-Asn-His-Gly-Ser-Phe-Tyr-Ser (SEQ ID NO: 96); Ala-Arg-His-Asn-Tyr-Gly-Ser-Phe-Tyr-Glu (SEQ ID NO:98); and Ala-Arg-His-Asn-Tyr-Gly-Ser-Phe-Tyr-Ser (SEQ ID NO:100).

The nucleotide sequences encoding the CDRS having multiple amino acid substitutions were $V_H$ CDR3 GCA AGA CAT AAC CAT GGC AGT TTT GCT TCT (SEQ ID NO:93), GCA AGA CAT AAC CAT GGC AGT TTT TAT TCT (SEQ ID NO:95), GCA AGA CAT AAC TAC GGC AGT TTT TAT GAG (SEQ ID NO:97), and GCA AGA CAT AAC TAC GGC AGT TTT TAT TCT (SEQ ID NO:99).

The invention also provides an enhanced LM609 grafted antibody exhibiting selective binding affinity to $\alpha_v\alpha_3$, wherein the enhanced LM609 grafted antibody contains at least one amino acid substitution in two or more CDRs of a LM609 grafted heavy chain variable region polypeptide or a LM609 grafted light chain variable region polypeptide.

An enhanced LM609 grafted antibody containing at least one amino acid substitution in two or more CDRs of a LM609 grafted heavy chain variable region polypeptide or a LM609 grafted light chain variable region polypeptide can include an LM609 grafted antibody containing the combination of CDRs selected from the group consisting of: the $V_L$ CDR1 SEQ ID NO:57 and the $V_H$ CDR3 SEQ. ID NO:50; the $V_L$ CDR1 SEQ ID NO:57, the $V_H$ CDR2 SEQ ID NO:44 and the $V_H$ CDR3 SEQ ID NO:50; the $V_L$ CDR1 SEQ ID NO:57, the $V_H$ CDR2 SEQ ID NO:44 and the $V_H$ CDR3 SEQ ID NO:52; the $V_L$ CDR1 SEQ ID NO:57, the $V_H$ CDR2 SEQ ID NO:44 and the $V_H$ CDR3 SEQ ID NO:51; the $V_L$ CDR1 SEQ ID NO:57 and the $V_H$ CDR3 SEQ ID NO:52; the $V_L$ CDR3 SEQ ID NO:59, the $V_H$ CDR2 SEQ ID NO:44 and the $V_H$ CDR3 SEQ ID NO:50; the $V_L$ CDR3 SEQ ID NO:61 and $V_H$ CDR3 SEQ ID NO:50; and the $V_L$ CDR3 SEQ ID NO:61, the $V_H$ CDR2 SEQ ID NO:44 and $V_H$ CDR3 SEQ ID NO:50.

In addition to enhanced LM609 grafted antibodies containing two or more CDRs having single amino acid substitutions, the invention also provides enhanced LM609 grafted antibodies wherein at least one of the CDRs has two or more amino acid substitutions.

Enhanced LM609 grafted antibodies having at least one CDR with two or more amino acid substitutions can include those containing the combination of CDRs selected from the group consisting of: the $V_L$ CDR1 SEQ ID NO:57, the $V_H$ CDR2 SEQ ID NO:44 and the $V_H$ CDR3 SEQ ID NO:63; the $V_L$ CDR3 SEQ ID NO:61, the $V_H$ CDR2 SEQ ID NO:44 and the $V_H$ CDR3 SEQ ID NO:63; the $V_L$ CDR3 SEQ ID NO:61, the $V_L$ CDR2 SEQ ID NO:44 and the $V_H$ CDR3 SEQ ID NO:4; the $V_L$ CDR3 SEQ ID NO:61 and the $V_H$ CDR3 SEQ ID NO:63; the $V_L$ CDR3 SEQ ID NO:61 and the $V_H$ CDR3 SEQ ID NO:65; and the $V_L$ CDR3 SEQ ID NO:61, the $V_H$ CDR2 SEQ ID NO:44 and the $V_H$ CDR3 SEQ ID NO:66.

The invention additionally provides a high affinity LM609 grafted antibody exhibiting selective binding affinity to $\alpha_v\beta_3$. The high affinity LM609 grafted antibody contains at least one amino acid substitution in one or more CDRs of a LM609 grafted heavy chain variable region polypeptide or a LM609 grafted light chain variable region polypeptide, wherein the $\alpha_v\beta_3$ binding affinity of the high affinity LM609 grafted antibody is enhanced.

High affinity antibodies can include those containing the combination of CDRs selected from the group consisting of: the $V_L$ CDR1 SEQ ID NO:57 and the $V_H$ CDR3 SEQ ID NO:50; the $V_L$ CDR1 SEQ ID NO:57, the $V_H$ CDR2 SEQ ID NO:44 and the $V_H$ CDR3 SEQ ID NO:50; the $V_L$ CDR1 SEQ ID NO:57, the $V_H$ CDR2 SEQ ID NO:44 and the $V_H$ CDR3 SEQ ID NO:52; the $V_L$ CDR1 SEQ ID NO:57, the $V_H$ CDR2 SEQ ID NO:44 and the $V_H$ CDR3 SEQ ID NO:51; the $V_L$ CDR1 SEQ ID NO:57 and the $V_H$ CDR3 SEQ ID NO:52; the $V_L$ CDR3 SEQ ID NO:59, the $V_H$ CDR2 SEQ ID NO:44 and the $V_H$ CDR3 SEQ ID NO:50; the $V_L$ CDR3 SEQ ID NO:61, the $V_H$ CDR2 SEQ ID NO:44 and the $V_H$ CDR3 SEQ ID NO:63; the $V_L$ CDR3 SEQ ID NO:61 and $V_H$ CDR3 SEQ ID NO:50; the $V_L$ CDR3 SEQ ID NO:61, the $V_H$ CDR2 SEQ ID NO:44 and $V_H$ CDR3 SEQ ID NO:50; the V, CDR1 SEQ ID NO:57, the $V_H$ CDR2 SEQ ID NO:44 and the $V_H$ CDR3 SEQ ID NO:63; the $V_L$ CDR3 SEQ ID NO:61, the $V_H$ CDR2 SEQ ID NO:44 and the $V_H$ CDR3 SEQ ID NO:64; the $V_L$ CDR3 SEQ ID NO:61 and the $V_H$ CDR3 SEQ ID NO:63; the $V_L$ CDR3 SEQ ID NO:61 and the $V_H$ CDR3 SEQ ID NO:65; and the $V_L$ CDR3 SEQ ID NO:61, the $V_H$ CDR2 SEQ ID NO:44 and the $V_H$ CDR3 SEQ ID NO:66.

As described above, enhanced LM609 antibodies can be further modified by introducing additional mutations in one or more CDRs or framework residues. As disclosed herein, the enhanced LM609 grafted antibody clone 6H6 (Table 10) was further modified by introducing mutations into one or more CDRs (see Example VIII). These 6H6 variants were found to have high affinity binding to $\alpha_v\beta_3$ and were resistant to proteolysis.

The invention further provides enhanced LM609 grafted antibodies comprising the $V_H$ CDR2 Lys-Val-Ser-Ser-Gly-Gly-Gly-Ser-Thr-Tyr-Tyr-Pro-Asp-Thr-Val-Gln-Gly (SEQ ID NO:104); the $V_H$ CDR3 His-Leu-His-Gly-Ser-Phe-Ala-Ser (SEQ ID NO:106); or the $V_L$ CDR1 Gln-Ala-Ser-Gln-Ser-Ile-Ser-Asn-Phe-Leu-His (SEQ ID NO:110). The invention also provides a nucleic acid molecule comprising a nucleotide sequence selected from the group consisting of SEQ ID NO:103, SEQ ID NO:105, and SEQ ID NO:109.

The invention also provides an enhanced LM609 grafted antibody comprising the $V_H$ CDR1 Gly-Phe-Thr-Phe-Ser-Ser-Tyr-Asp-Met-Ser (SEQ ID NO:34); the $V_H$ CDR2 Lys-Val-Ser-Ser-Gly-Gly-Gly-Ser-Thr-Tyr-Tyr-Leu-Asp-Thr-Val-Gln-Gly (SEQ ID NO:102); the $V_H$ CDR3 His-Leu-His-Gly-Ser-Phe-Ala-Ser (SEQ ID NO:106); the $V_L$ CDR1 Gln-Ala-Ser-Gln-Ser-Ile-Ser-Asn-His-Leu-His (SEQ ID NO:108); the $V_L$ CDR2 Tyr-Arg-Ser-Gln-Ser-Ile-Ser (SEQ ID NO:112); and the $V_L$ CDR3 Gln-Gln-Ser-Gly-Ser-Trp-Pro-Leu-Thr (SEQ ID NO:90).

The invention also provides a nucleic acid molecule comprising the nucleotide sequence referenced as SEQ ID NO:33 encoding a $V_H$ CDR1; the nucleotide sequence referenced as SEQ ID NO:101 encoding a $V_H$ CDR2; the nucleotide sequence referenced as SEQ ID NO:105 encoding a $V_H$ CDR3; the nucleotide sequence referenced as SEQ ID NO:107 encoding a $V_L$ CDR1; the nucleotide sequence referenced as SEQ ID NO:111 encoding a $V_L$ CDR2; and the nucleotide sequence referenced as SEQ ID NO:89 encoding a $V_L$ CDR3.

The invention additionally provides an enhanced LM609 grafted antibody comprising the $V_H$ CDR1 Gly-Phe-Thr-Phe-Ser-Ser-Tyr-Asp-Met-Ser (SEQ ID NO:34); the $V_H$ CDR2 Lys-Val-Ser-Ser-Gly-Gly-Gly-Ser-Thr-Tyr-Tyr-Leu-Asp-Thr-Val-Gln-Gly (SEQ ID NO:102); the $V_H$ CDR3 His-Leu-His-Gly-Ser-Phe-Ala-Ser (SEQ ID NO:106); the $V_L$ CDR1 Gln-Ala-Ser-Gln-Ser-Ile-Ser-Asn-Phe-Leu-His (SEQ ID NO:110); the $V_L$ CDR2 Tyr-Arg-Ser-Gln-Ser-Ile-Ser (SEQ ID NO:112); and the $V_L$ CDR3 Gln-Gln-Ser-Gly-Ser-Trp-Pro-Leu-Thr (SEQ ID NO:90).

The invention additionally provides a nucleic acid molecule comprising the nucleotide sequence referenced as SEQ ID NO:33 encoding a $V_H$ CDR1; the nucleotide sequence referenced as SEQ ID NO:101 encoding a $V_H$ CDR2; the nucleotide sequence referenced as SEQ ID NO:105 encoding a $V_H$ CDR3; the nucleotide sequence referenced as SEQ ID NO:109 encoding a $V_L$ CDR1; the nucleotide sequence referenced as SEQ ID NO:111 encoding a $V_L$ CDR2; and the nucleotide sequence referenced as SEQ ID NO:89 encoding a $V_L$ CDR3.

The invention further provides an enhanced LM609 grafted antibody comprising the $V_H$ CDR1 Gly-Phe-Thr-Phe-Ser-Ser-Tyr-Asp-Met-Ser (SEQ ID NO:34); the $V_H$ CDR2 Lys-Val-Ser-Ser-Gly-Gly-Gly-Ser-Thr-Tyr-Tyr-Pro-Asp-Thr-Val-Gln-Gly (SEQ ID NO:104); the $V_H$ CDR3 His-Leu-His-Gly-Ser-Phe-Ala-Ser (SEQ ID NO:106); the $V_L$ CDR1 Gln-Ala-Ser-Gln-Ser-Ile-Ser-Asn-Phe-Leu-His (SEQ ID NO:110); the V. CDR2 Tyr-Arg-Ser-Gln-Ser-Ile-Ser (SEQ ID NO:112); and the $V_L$ CDR3 Gln-Gln-Ser-Gly-Ser-Trp-Pro-Leu-Thr (SEQ ID NO:90).

The invention further provides a nucleic acid molecule comprising the nucleotide sequence referenced as SEQ ID NO:33 encoding a $V_H$ CDR1; the nucleotide sequence referenced as SEQ ID NO:103 encoding a $V_H$ CDR2; the nucleotide sequence referenced as SEQ ID NO:105 encoding a $V_H$ CDR3; the nucleotide sequence referenced as SEQ ID NO:109 encoding a $V_L$ CDR1; the nucleotide sequence referenced as SEQ ID NO:111 encoding a $V_L$ CDR2; and the nucleotide sequence referenced as SEQ ID NO:89 encoding a $V_L$ CDR3.

The invention additionally provides a nucleic acid encoding an enhanced LM609 grafted antibody exhibiting selective binding affinity to $\alpha_v\beta_3$. The enhanced LM609 grafted antibody encoded by the nucleic acid contains at least one amino acid substitution in one or more CDRs of a LM609 grafted heavy chain variable region polypeptide or a LM609 grafted light chain variable region polypeptide, wherein the $\alpha_v\beta_3$ binding affinity of the enhanced LM609 grafted antibody is maintained or enhanced.

The invention further provides a nucleic acid encoding a high affinity LM609 grafted antibody exhibiting selective binding affinity to $\alpha_v\beta_3$. The high affinity LM609 grafted antibody encoded by the nucleic acid contains at least one amino acid substitution in one or more CDRs of a LM609 grafted heavy chain variable region polypeptide or a LM609 grafted light chain variable region polypeptide, wherein the $\alpha_v\beta_3$ binding affinity of the high affinity LM609 grafted antibody is enhanced.

The invention provides a nucleic acid encoding a heavy chain polypeptide for monoclonal antibody LM609 or functional fragment thereof. Also provided is a nucleic acid encoding a light chain polypeptide for monoclonal antibody LM609 or a functional fragment thereof. The nucleic acids consist of substantially the same heavy or light chain variable region nucleotide sequences as that shown in FIGS. 2A and 2B (SEQ ID NOS:5 and 7, respectively) or a fragment thereof.

As described previously, monoclonal antibody LM609 has been shown in the art to have binding activity to the integrin $\alpha_v\beta_3$. Although specificity can in principle be generated towards essentially any target, LM609 is an integrin inhibitory antibody that exhibits substantial specificity and inhibitory activity to a single member within an integrin family. In this case, LM609 exhibits substantial specificity and inhibitory activity to the $\alpha_v\beta_3$ integrin within the $\beta_3$ family. The amino acid or nucleotide sequence of monoclonal antibody LM609 has never been previously isolated and characterized.

The isolation and characterization of LM609 encoding nucleic acids was performed by techniques known to those skilled in the art and which are described further below in the Examples. Briefly, cDNA from hybridoma LM609 was generated and used as the source for which to isolate LM609 encoding nucleic acids. Isolation was performed by first determining the N-terminal amino acid sequence for each of the heavy and light chain polypeptides and then amplifying by PCR the antibody encoding sequences from the cDNA. The 5' primers were reverse translated to correspond to the newly determined N-terminal amino acid sequences whereas the 3' primers corresponded to sequences substantially similar to antibody constant region sequences. Amplification and cloning of the products resulted in the isolation of the nucleic acids encoding heavy and light chains of LM609.

The nucleotide sequences of the LM609 heavy and light chain variable region sequences are shown in FIGS. 2A and 2B, respectively. These sequences correspond substantially to those that encode the variable region heavy and light chain polypeptides of LM609. As with the vitaxin nucleic acids, these LM609 nucleic acids are intended to include both sense and anti-sense strands of the LM609 encoding sequences. Single- and double-stranded nucleic acids are also include as well as non-coding portions of the nucleic acid such as introns, 5'- and 3'-untranslated regions and regulatory sequences of the gene for example.

As shown in FIG. 2A, the LM609 heavy chain variable region polypeptide is encoded by a nucleic acid of about 351 nucleotides in length which begins at the amino terminal Glu1 residue of the variable region through to Ala 117. The murine LM609 antibody heavy chain has an IgG2a constant region. Shown in FIG. 2B is the LM609 light chain variable region polypeptide which is encoded by a nucleic acid of about 321 nucleotides in length which begins at the amino terminal Asp1 residue of the variable region through to Lys 107. In the functional antibody, LM609 has a kappa light chain constant region.

As with the Vitaxin nucleic acids, minor modifications of these LM609 nucleotide sequences are intended to be included as heavy and light chain LM609 encoding nucleic acids. Such minor modifications are included within the nucleic acids encoding LM609 heavy and light chain polypeptides so long as the nucleic acids or encoded polypeptides retain some or all of their function as described.

Thus, the invention also provides a nucleic acid encoding a LM609 heavy chain or functional fragment wherein the nucleic acid encodes substantially the same variable region amino acid sequence of monoclonal antibody LM609 as that shown in FIG. 2A (SEQ ID NO:6) or a fragment thereof. Similarly, the invention also provides a nucleic acid encoding a LM609 light chain or functional fragment wherein the nucleic acid encodes substantially the same variable region amino acid sequence of monoclonal antibody LM609 as that shown in FIG. 2B (SEQ ID NO:8) or a fragment thereof.

The invention further provides fragments of LM609 heavy and light chain encoding nucleic acids wherein such fragments consist substantially of the same nucleotide or amino acid sequence as the variable region of LM609 heavy or light chain polypeptides. The variable region of the LM609 heavy chain polypeptide consists essentially of nucleotides 1-351 and of amino acid residues Glu1 to Ala117 of FIG. 2A (SEQ ID NOS:5 and 6, respectively). The variable region of the LM609 light chain polypeptide consists essentially of nucleotides 1-321 and of amino acid residues Asp1 to Lys107 of FIG. 2B (SEQ ID NOS:7 and 8, respectively). The termini of such variable region encoding nucleic acids is not critical so long as the intended purpose and function remains the same. Such intended purposes and functions include, for example, use for the production of recombinant polypeptides or as hybridization probes for heavy and light chain variable region sequences.

Fragments additional to the variable region nucleic acid fragments are provided as well. Such fragments include, for example, nucleic acids consisting substantially of the same nucleotide sequence as a CDR of a LM609 heavy or light chain polypeptide. Sequences corresponding to the LM609 CDRs include, for example, those regions within the variable region which are defined by Kabat et al., supra, and/or those regions within the variable regions which are defined by Chothia et al., supra, as well as those regions defined by MacCallum et al., supra. The LM609 CDR fragments for each of the above definitions correspond to the nucleotides set forth below in Table 4. The nucleotide sequence numbering is taken from the primary sequence shown in FIGS. 2A and 2B (SEQ ID NOS:5 and 7) and conforms to the definitions previously set forth in Table 1.

TABLE 4

| LM609 CDR Nucleotide Residues | | | |
|---|---|---|---|
| | Kabat | Chothia | MacCallum |
| $V_H$ CDR1 | 91-105 | 76-96 | 88-105 |
| $V_H$ CDR2 | 148-198 | 157-168 | 139-177 |
| $V_H$ CDR3 | 295-318 | 298-315 | 288-315 |
| $V_L$ CDR1 | 70-102 | 76-96 | 88-108 |
| $V_L$ CDR2 | 148-168 | 148-156 | 136-165 |
| $V_L$ CDR3 | 265-291 | 271-288 | 265-288 |

Similarly, the LM609 CDR fragments for each of the above definitions correspond to the amino acid residues set forth below in Table 5. The amino acid residue numbering is taken from the primary sequence shown in FIGS. 2A and 2B (SEQ ID NOS:6 and 8) and conforms to the definitions set forth in Table 1.

TABLE 5

| LM609 CDR Amino Acid Residues | | | |
|---|---|---|---|
| | Kabat | Chothia | MacCallum |
| $V_H$ CDR1 | Ser31-Ser35 | Gly26-Tyr32 | Ser30-Ser35 |
| $V_H$ CDR2 | Lys50-Gly66 | Ser53-Gly56 | Trp47-Tyr59 |
| $V_H$ CDR3 | His99-Tyr106 | Asn100-Ala105 | Ala97-Alal05 |
| $V_L$ CDR1 | Gln24-His34 | Ser26-His32 | Ser30-Tyr36 |
| $V_L$ CDR2 | Tyr50-Ser56 | Tyr50-Ser52 | Leu46-Ile55 |
| $V_L$ CDR3 | Gln89-Thr97 | Ser91-His96 | Gln89-His96 |

Nucleic acids encoding LM609 heavy and light chain polypeptides and fragments thereof are useful for a variety of diagnostic and therapeutic purposes. For example, the LM609 nucleic acids can be used to produce recombinant LM609 antibodies and functional fragments thereof having binding specificity and inhibitory activity against the integrin $\alpha_v\beta_3$. The antibody and functional fragments thereof can be used to determine the presence or absence of $\alpha_v\beta_3$ in a sample to diagnose the susceptibility or occurrence of an $\alpha_v\beta_3$-mediated disease. Alternatively, the recombinant LM609 antibodies and functional fragments thereof can be used for the therapeutic treatment of $\alpha_v\beta_3$-mediated diseases or pathological state. As with Vitaxin, recombinant LM609 and functional fragments thereof can be used to inhibit the binding activity or other functional activities of $\alpha_v\beta_3$ that are necessary for progression of the $\alpha_v\beta_3$-mediated disease or pathological state.

The LM609 nucleic acids of the invention can also be used to model functional equivalents of the encoded heavy and light chain polypeptides. Such functional equivalents can include, for example, synthetic analogues or mimics of the encoded polypeptides or functional fragments thereof. A specific example would include peptide mimetics of the LM609 CDRs that retain some or substantially the same binding or inhibitory activity of LM609. Additionally, the LM609 encoding nucleic acids can be used to engineer and produce nucleic acids which encode modified forms or derivatives of the antibody LM609, its heavy and light chain polypeptides and functional fragments thereof. As described previously, such modified forms or derivatives include, for example, non-mouse antibodies, their corresponding heavy and light chain polypeptides and functional fragments thereof which exhibit substantially the same binding and inhibitory activity as LM609.

The invention also provides a method of treating an $\alpha_v\beta_3$-mediated disease. The method consists of administering an effective amount of Vitaxin, a LM609 grafted antibody, an enhanced antibody thereof, or a functional fragment thereof under conditions which allow binding to $\alpha_v\beta_3$. Also provided is a method of inhibiting a function of $\alpha_v\beta_3$. The method consists of contacting $\alpha_v\beta_3$ with Vitaxin, a LM609 grafted antibody or a functional fragment thereof under conditions which allow binding to $\alpha_v\beta_3$.

As described previously, Vitaxin and LM609 grafted antibodies are monoclonal antibodies which exhibit essentially all of the binding characteristics as does its parental CDR-donor antibody LM609. These characteristics include, for example, significant binding specificity and affinity for the integrin $\alpha_v\beta_3$. The Examples below demonstrate these binding properties and further show that the binding of such antibodies to $\alpha_v\beta_3$ inhibits $\alpha_v\beta_3$ ligand binding and function. Thus, Vitaxin and LM609 grafted antibodies are useful for a large variety of diagnostic and therapeutic purposes directed to the inhibition of $\alpha_v\beta_3$ function.

The integrin $\alpha_v\beta_3$ functions in numerous cell adhesion and migration associated events. As such, the dysfunction or dysregulation of this integrin, its function; or of cells expressing this integrin, is associated with a large number of diseases and pathological conditions. The inhibition $\alpha_v\beta_3$ binding or function can therefore be used to treat or reduce the severity of such $\alpha_v\beta_3$-mediated pathological conditions. Described below are examples of several pathological conditions mediated by $\alpha_v\beta_3$, since the inhibition of at least this integrin reduces the severity of the condition. These examples are intended to be representative and as such are not inclusive of all $\alpha_v\beta_3$-mediated diseases. For example, there are numerous pathological conditions additional to those discussed below which exhibit the dysregulation of $\alpha_v\beta_3$ binding, function or the dysregulation of cells expressing this integrin and in which the pathological condition can be reduced, or will be found to be reduced, by inhibiting the binding $\alpha_v\beta_3$. Such pathological conditions which exhibit this criteria, are intended to be included within the definition of the term as used herein.

Angiogenesis, or neovascularization, is the process where new blood vessels form from pre-existing vessels within a tissue. As described further below, this process is mediated by endothelial cells expressing $\alpha_v\beta_3$ and inhibition of at least this integrin, inhibits new vessel growth. There are a variety of pathological conditions that require new blood vessel formation or tissue neovascularization and inhibition of this process inhibits the pathological condition. As such, pathological conditions that require neovascularization for growth or maintenance are considered to be $\alpha_v\beta_3$-mediated diseases. The extent of treatment, or reduction in severity, of these diseases will therefore depend on the extent of inhibition of neovascularization. These $\alpha_v\beta_3$-mediated diseases include, for example, inflammatory disorders such as immune and non-immune inflammation, chronic articular rheumatism, psoriasis, disorders associated with inappropriate or inopportune invasion of vessels such as diabetic retinopathy, neovascular glaucoma and capillary proliferation in atherosclerotic plaques as well as cancer disorders. Such cancer disorders can include, for example, solid tumors, tumor metastasis, angiofibromas, retrolental, fibroplasia, hemangiomas, Kaposi's sarcoma and other cancers which require neovascularization to support tumor growth. Additional diseases which are considered angiogenic include psoriasis and rheumatoid arthritis as well as retinal diseases such as macular degeneration. Diseases other than those requiring new blood vessels which are $\alpha_v\beta_3$-mediated diseases include, for example, restenosis and osteoporosis.

Treatment of the $\alpha_v\beta_3$-mediated diseases can be performed by administering an effective amount of Vitaxin, a LM609 grafted antibody, an enhanced antibody thereof, or a functional fragment thereof so as to bind to $\alpha_v\beta_3$ and inhibit its function. Administration can be performed using a variety of methods known in the art. The choice of method will depend on the specific $\alpha_v\beta_3$ mediated disease and can include, for example, the in vivo, in situ and ex vivo administration of Vitaxin, a LM609 grafted antibody or functional fragment thereof, to cells, tissues, organs, and organisms. Moreover, such antibodies or functional fragments can be administered to an individual exhibiting or at risk of exhibiting an $\alpha_v\beta_3$-mediated disease. Definite clinical diagnosis of an $\alpha_v\beta_3$-mediated disease warrants the administration of Vitaxin, a LM609 grafted antibody or a functional fragment thereof. Prophylactic applications are warranted in diseases where the $\alpha_v\beta_3$-mediated disease mechanisms precede the onset of overt clinical disease. Thus, individuals with familial history of disease and predicted to be at risk by reliable prognostic indicators can be treated prophylactically to interdict $\alpha_v\beta_3$-mediated mechanisms prior to their onset.

Vitaxin, a LM609 grafted antibody, an enhanced antibody thereof, or functional fragments thereof can be administered in a variety of formulations and pharmaceutically acceptable media for the effective treatment or reduction in the severity of an $\alpha_v\beta_3$-mediated disease. Such formulations and pharmaceutically acceptable medias are well known to those skilled in the art. Additionally, Vitaxin, a LM609 grafted antibody or functional fragments thereof can be administered with other compositions which can enhance or supplement the treatment or reduction in severity of an $\alpha_v\beta_3$-mediated disease. For example, the coadministration of Vitaxin or a LM609 grafted antibody to inhibit tumor-induced neovascularization and a chemotherapeutic drug to directly inhibit tumor growth is one specific case where the administration of other compositions can enhance or supplement the treatment of an $\alpha_v\beta_3$-mediated disease.

Vitaxin, a LM609 grafted antibody or functional fragments are administered by conventional methods, in dosages which are sufficient to cause the inhibition of $\alpha_v\beta_3$ integrin binding at the sight of the pathology. Inhibition can be measured by a variety of methods known in the art such as in situ immunohistochemistry for the prevalence of $\alpha_v\beta_3$ containing cells at the site of the pathology as well as include, for example, the observed reduction in the severity of the symptoms of the $\alpha_v\beta_3$-mediated disease.

In vivo modes of administration can include intraperitoneal, intravenous and subcutaneous administration of Vitaxin, a LM609 grafted antibody or a functional fragment thereof. Dosages for antibody therapeutics are known or can be routinely determined by those skilled in the art. For example, such dosages are typically administered so as to achieve a plasma concentration from about 0.01 µg/ml to about 100 µg/ml, preferably about 1-5 µg/ml and more preferably about 5 µg/ml. In terms of amount per body weight, these dosages typically correspond to about 0.1-300 mg/kg, preferably about 0.2-200 mg/kg and more preferably about 0.5-20 mg/kg. Depending on the need, dosages can be administered once or multiple times over the course of the treatment. Generally, the dosage will vary with the age, condition, sex and extent of the $\alpha_v\beta_3$-mediated pathology of the subject and should not be so high as to cause adverse side effects. Moreover, dosages can also be modulated by the physician during the course of the treatment to either enhance the treatment or reduce the potential development of side effects. Such procedures are known and routinely performed by those skilled in the art.

The specificity and inhibitory activity of Vitaxin, LM609 grafted antibodies, an enhanced antibody thereof and functional fragments thereof allow for the therapeutic treatment of numerous $\alpha_v\beta_3$-mediated diseases. Such diseases include, for example, pathological conditions requiring neovascularization such as tumor growth, and psoriasis as well as those directly mediated by $\alpha_v\beta_3$ such as restenosis and osteoporosis. Thus, the invention provides methods as well as Vitaxin and LM609 grafted antibody containing compositions for the treatment of such diseases.

It is understood that modifications which do not substantially affect the activity of the various embodiments of this invention are also included within the definition of the invention provided herein. Accordingly, the following examples are intended to illustrate but not limit the present invention.

EXAMPLE I

Isolation and Characterization of LM609 Encoding Nucleic Acids

This Example shows the cloning and sequence determination of LM609 encoding nucleic acids.

LM609 is directed against the human vitronectin receptor, integrin $\alpha_v\beta_3$. $\alpha_v\beta_3$ is highly upregulated in melanoma, glioblastoma, and mammary carcinoma and plays a role in the proliferation of M21 melanoma cells both in vitro and in vivo. $\alpha_v\beta_3$ also plays a role in angiogenesis, restenosis and the formation of granulation tissue in cutaneous wounds. LM609 has been shown to inhibit the adhesion of M21 cells to vitronectin as well as prevent proliferation of M21 cells in vitro. Thus, grafting of LM609 could result in a clinically valuable therapeutic agent.

cDNA Synthesis of LM609 Variable Regions: For cDNA synthesis, total RNA was prepared from 108 LM609 hybridoma cells using a modification of the method described by Chomczynski and Sacchi (Chomczynski and Sacchi, *Analyt. Biochem.* 162:156 (1987)). LM609 variable (V) region genes were cloned by reverse transcription-polymerase chain reaction (RT-PCR) and cDNA was synthesized using BRL Superscript kit. Briefly, 5 µg of total cellular RNA, 650 ng oligo dT and H$_2$O were brought to a total volume of 55 µl. The sample was heated to 70° C. for 10 min and chilled on ice. Reaction buffer was added and the mixture brought to 10 mM DTT and 1 mM dNTPs and heated at 37° C. for 2 minutes. 5 µl (1000 units) reverse transcriptase was added and incubated at 37° C. for 1 hour and then chilled on ice.

All oligonucleotides were synthesized by β-cyanoethyl phosphoramidite chemistry on an ABI 394 DNA synthesizer. Oligonucleotides used for PCR amplification and routine site-directed mutagenesis were purified using oligonucleotide purification cartridges (Applied Biosystems, Foster City, Calif.). Forward PCR primers were designed from N-terminal protein sequence data generated from purified LM609 antibody. The forward PCR primers contained sequences coding for the first six amino acids in each antibody variable chain (protein sequenced at San Diego State University). The sequence of the light chain forward PCR primer (997) was 5'-GCC CAA CCA GCC ATG CCC GAT ATT GTG CTA ACT CAG-3' (SEQ ID NO:19) whereas the light chain reverse PCR primer (734) was 5'-AC AGT TGG TGC AGC ATC AGC-3' (SEQ ID NO:20) used. This reverse primer corresponds to mouse light chain kappa amino acid residues 109-115. The sequence of the heavy chain forward PCR primer (998) was 5'-ACC CCT GTG GCA AAA GCC GAA GTG CAG CTG GTG GAG-3' (SEQ ID NO:21). Heavy chain reverse PCR primer 733: 5'-GA TGG GGG TGT CGT TTT GGC-3' SEQ ID NO:22). The PCR primers also contain regions of homology with specific sequences within the immunoexpression vector.

V$_L$ and V$_H$ chains were amplified in two separate 50 µl reaction mixtures containing 2 µl of the cDNA-RNA heteroduplex, 66.6 mM Tris-HCl pH 8.8, 1.5 mM MgCl$_2$, 0.2 mM of each four dNTPs, 10 mM 2-mercaptoethanol, 0.25 units Taq polymerase (Boehringer-Mannheim, Indianapolis, Ind.) and 50 pmoles each of primers 997 and 734 and 998 and 733, respectively. The mixtures were overlaid with mineral oil and cycled for two rounds of PCR with each cycle consisting of 30 seconds at 94° C. (denature)/30 seconds at 50° C. (anneal), and 30 seconds at 72° C. (synthesis). This reaction was immediately followed by 30 cycles of PCR consisting of 30 seconds at 94° C. (denature), 30 seconds at 55° C. (anneal), and 30 seconds at 72° C. (synthesis) followed by a final synthesis reaction for 5 minutes at 72° C. The reaction products were pooled, extracted with CHCl$_3$ and ethanol precipitated.

Amplified products were resuspended in 20 µl TE buffer (10 mM Tris-HCl, 1 mM EDTA, pH 8.0) and electrophoresed on a 5% polyacrylamide gel. Bands migrating at expected molecular weights of V$_H$ and V$_L$ were excised, chemically eluted from the gel slice, extracted with organic solvents and ethanol precipitated.

Cloning of amplified V$_H$ and V$_L$ genes into M13 phage immunoexpression vector: The amplified V region gene products were sequentially cloned into the phage immunoexpression vector by hybridization mutagenesis (Near, R. *Biotechniques* 12:88 (1992); Yelton et al., *J. Immunol.* 155:1994-2003 (1995)). Introduction of the amplified V$_L$ and V$_H$ sequences by hybridization mutagenesis positions the antibody sequences in frame with the regulatory elements contained in the M13 vector required for efficient Fab expression. One advantage of this technique is that no restriction endonuclease sites need to be incorporated into the $V_L$ or $V_H$ gene sequences for cloning as is done with conventional DNA ligation methods.

To perform the cloning, 400 ng each of the double-stranded amplified products were first phosphorylated with polynucleotide kinase. 100 ng of the phosphorylated LM609 $V_L$ product was mixed with 250 ng of uridinylated BS11 phage immunoexpression vector, denatured by heating to 90° C. and annealed by gradual cooling to room temperature. BS11 is an M13 immunoexpression vector derived from M13 IX and encodes $CH_1$ of murine IgG1 and murine kappa light chain constant domain (Huse, W. D. In: *Antibody Engineering: A Practical Guide*, C. A. K. Borrebaeck, ed. W. H. Freeman and Co., Publishers, New York, pp. 103-120 (1991)). Nucleotide sequences included in the PCR amplification primers anneal to complementary sequences present in the single-stranded BS11 vector. The annealed mixture was fully converted to a double-stranded molecule with T4 DNA polymerase plus dNTPs and ligated with T4 ligase. 1 μl of the mutagenesis reaction was electroporated into *E. coli* strain DH10B, titered onto a lawn of XL-1 *E. coli* and incubated until plaques formed. Plaque lift assays were performed as described using goat anti-murine kappa chain antibody conjugated to alkaline phosphatase (Yelton et al., supra; Huse, W. D., supra). Fifteen murine light chain positive M13 phage clones were isolated, pooled and used to prepare uridinylated vector to serve as template for hybridization mutagenesis with the PCR amplified LM609 $V_H$ product.

Clones expressing functional murine LM609 Fab were identified by binding to purified $\alpha_v\beta_3$ by ELISA. Briefly, Immulon II ELISA plates were coated overnight with 1 μg/ml (100 ng/well) $\alpha_v\beta_3$ and nonspecific sites blocked for two hours at 27° C. Soluble Fabs were prepared by isolating periplasmic fractions of cultures of *E. coli* strain MK30-3 (Boehringer Mannheim Co.) infected with the Fab expressing M13 phage clones. Periplasm fractions were mixed with binding buffer 100 mM NaCl, 50 mM Tris pH 7.4, 2 mM $CaCl_2$, 1 mM $MgCl_2$, 1 mM $MnCl_2$, 0.02% $NaN_3$, 1 mg/ml BSA and incubated with immobilized $\alpha_v\beta_3$ for two hours at 27° C. Plates were washed with binding buffer and bound Fab detected with goat anti-murine kappa chain antibody conjugated to alkaline phosphatase. Four $\alpha_v\beta_3$ reactive clones were identified: muLM609M13 12, 29, 31 and 69. MuLM609M13 12 and 29 gave the strongest signals in the ELISA assay. DNA sequence analysis showed that clones muLM609M13 12, 31 and 69 all had identical light chain sequence and confirmed the previously determined N-terminal amino acid sequence of purified LM609 light chain polypeptide. All four clones had identical $V_H$ DNA sequence and also confirmed the previously determined N-terminal amino acid sequence of purified LM609 heavy chain polypeptide.

To further characterize the binding activity of each clone, soluble Fab fractions were prepared from 50 ml cultures of *E. coli* strain MK30-3 infected with clones 12 and 29 and evaluated for binding to $\alpha_v\beta_3$ in a competitive ELISA with LM609 IgG. The results of this ELISA are shown in FIG. 3. Clone muLM609M13 12 was found to inhibit LM609 IgG binding (at LM609 IgG concentrations of 1 ng/ml and 5 ng/ml) to $\alpha_v\beta_3$ in a concentration dependent manner at periplasm titers ranging from neat to 1:80. Clone muLM609M13 12 was plaque purified and both the V region heavy and light chain DNA sequences again determined. Complete DNA sequence of the final clone, muLM609M13 12-5, is shown in FIGS. 2A and 2B.

EXAMPLE II

Construction of Vitaxin: A CDR Grafted LM609 Functional Fragment

One goal of grafting antibodies is to preserve antibody specificity and affinity when substituting non-human CDRs into a human antibody framework. Another goal is to minimize the introduction of foreign amino acid sequences so as to reduce the possible antigenicity with a human host. This Example describes procedures for accomplishing both of these goals by producing libraries of grafted antibodies which represent all possible members which exhibit the highest affinities for the desired antigen.

The above library was constructed in *E. coli* wherein the possible CDR and framework changes were incorporated using codon-based mutagenesis (Kristensson et al., In: Vaccines 95. Cold Spring Harbor Laboratory Press. Cold Spring Harbor, N.Y. (1995); Rosok et al., *J. Biol. Chem.* (271:22611-22613 (1996)). Using these procedures, a library was constructed and a functionally active humanized anti-$\alpha_v\beta_3$-inhibitory antibody was identified.

For the construction of one grafted form of LM609, human framework sequences showing the highest degree of identity to the murine LM609 V region gene sequences were selected for receiving the LM609 CDRs. Human heavy chain V region M72 'CL (HHC30Q, HC Subgroup 3, Kabat et al., supra) had 88% identity to frameworks 1, 2 and 3 of LM609 heavy chain and human light chain V region LS1 'CL (HKL312, Kappa subgroup 3, Kabat et al., supra) had 79% identity to frameworks 1, 2 and 3 of LM609 light chain. Murine LM609 CDR sequences, as defined by Kabat et al., supra were grafted onto the human frameworks. Residues predicted to be buried that might affect the structure and therefore the binding properties of the original murine combining site were taken into consideration when designing possible changes (Singer et al., supra; Padlan, E. A. *Mol. Immunol.* 28:489-498 (1991)). This analysis of framework residues considered to be important for preserving the specificity and affinity of the combining site revealed only a few differences. For example, in the heavy chain sequence, the predicted buried residues displayed 100% identity. Of particular note is that Arg16 in human heavy chain V region M72 'CL is a relatively uncommon residue among human chains. However, this residue was also found to be present in LM609 $V_H$ and therefore was retained. Similarly, Arg19 in LM609 is a relatively rare residue among murine heavy chains but it is found to occur in M72 'CL and was therefore retained. In the light chain sequences, two nonidentical buried residues were identified between LM609 and LS1 'CL framework regions at positions 49 and 87. These two positions were therefore incorporated into the grafted antibody library as both human and murine alternatives.

Full-length grafted V region genes were synthesized by PCR using long overlapping oligonucleotides. Light chain oligonucleotides containing mixed amino acid residues at positions 49 and 87 were synthesized as described in Glaser et al. (*J. Immunol.* 149:3903-3913 (1992)) and as illustrated in the oligonucleotides represented as $V_L$ oligo3 and $V_L$ oligo4. (SEQ ID NOS:16 and 17, respectively). All long oligonucleotides were gel purified.

Grafted LM609 heavy and light chain V regions were constructed by mixing 5 overlapping oligonucleotides at equimolar concentrations, in the presence of annealing PCR primers. The heavy chain oligonucleotides map to the following nucleotide positions: $V_H$ oligonucleotide 1 ($V_H$ oligo1), nucleotides (nt) 1-84; (SEQ ID NO:9); $V_H$ oligo2, nt 70-153, (SEQ ID NO:10); $V_H$ oligo3, nt 138-225 (SEQ ID NO:11); $V_H$ oligo4, nt 211-291 (SEQ ID NO:12); $V_H$ oligo5, nt 277-351 (SEQ ID NO:13). Similarly, the Vitaxin light chain oligonucleotides map to the following nucleotide positions: $V_L$ oligonucleotide 1 ($V_L$ oligo1), nucleotides (nt) 1-87; (SEQ ID NO:14); $V_L$ oligo2, nt 73-144, (SEQ ID NO:15); $V_L$ oligo3, nt 130-213 (SEQ ID NO:16); $V_L$ oligo4, nt 199-279 (SEQ ID NO:17); $V_L$ oligo5, nt 265-321 (SEQ ID NO:18). The nucleotide sequences of oligonucleotides used to construct grafted LM609 heavy and light chain variable regions are shown in Table 6. Codon positions 49 and 87 in $V_L$ oligo3, and $V_L$ oligo4 represent the randomized codons. The annealing primers contained at least 18 nucleotide residues complementary to vector sequences for efficient annealing of the amplified V region product to the single-stranded vector. The annealed mixture was fully converted to a double-stranded molecule with T4 DNA polymerase plus dNTPs and ligated with T4 ligase.

To generate the library, a portion of the mutagenesis reaction (1 μl) was electroporated into *E. coli* strain DH10B (BRL), titered onto a lawn of XL-1 (Stratagene, Inc.) and incubated until plaques formed. Replica filter lifts were prepared and plaques containing $V_H$ gene sequences were screened either by hybridization with a digoxigenin-labeled oligonucleotide complementary to LM609 heavy chain CDR 2 sequences or reactivity with 7F11-alkaline phosphatase conjugate, a monoclonal antibody raised against the decapeptide sequence Tyr Pro Tyr Asp Val Pro Asp Tyr Ala Ser (SEQ ID NO:28) appended to the carboxy terminus of the vector $CH_1$ domain (Biosite, Inc., San Diego, Calif.). Fifty clones that were double-positive were pooled and used to prepare uridinylated template for hybridization mutagenesis with the amplified grafted LM609 $V_L$ product.

TABLE 6

Oligonucleotides Used to Construct Grafted
LM609 Heavy and Light Chain Variable Regions SEQ ID NO: 9
CAGGTGCAGC TGGTGGAGTC TGGGGGAGGC GTTGTGCAGC
CTGGAAGGTC CCTGAGACTC TCCTGTGCAG CCTCTGGATT CACC SEQ ID NO: 10
AACTTTTGCG ACCCACTCCA GACCCTTGCC CGGAGCCTGG
CGAACCCAAG ACATGTCATA GCTACTGAAG GTGAATCCAG AGGC SEQ ID NO: 11
TGGGTCGCAA AAGTTAGTAG TGGTGGTGGT AGCACCTACT
ATTTAGACAC TGTGCAGGGC CGATTCACCA TCTCCAGAGA
CAATAGT SEQ ID NO: 12
TGCACAGTAA TACACGGCTG TGTCCTCCGC TCTCAGAGAC
TTCATTTGCA GGTATAGGGT GTTCTTACTA TTGTCTCTGG A SEQ ID NO: 13
GTGTATTACT GTGCAAGACA TAACTACGGC ACTTTTGCTT
ACTGGGGCCA AGGGACTACA GTGACTGTTT CTACT SEQ ID NO: 14
GAGATTGTGC TAACTCAGTC TCCAGCCACC CTGTCTCTCA
GCCCAGGAGA AAGGGCGACT CTTTCCTGCC AGGCCAGCCA
AAGTATT SEQ ID NO: 15
GATGAGAAGC CTTGGGCTT GACCAGGCCT TTGTTGATAC
CAGTGTAGGT GGTTGCTAAT ACTTTGGCTG GC TABLE 6-continued Oligonucleotides Used to Construct Grafted
LM609 Heavy and Light Chain Variable Regions SEQ ID NO: 16
CCAAGGCTTC TCATCWASTA TCGTTCCCAG TCCATCTCTG
GGATCCCCGC CAGGTTCAGT GGCAGTGGAT CAGGGACAGA TTTC SEQ ID NO: 17
GCTGCCACTC TGTTGACAGW AATAGACTGC AAAATCTTCA
GGCTCCAGAC TGGAGATAGT GAGGGTGAAA TCTGTCCCTG A

SEQ ID NO: 18
CAACGAGTG GCAGCTGGCC TCACACGTTC GGAGGGGGGA
CCAAGGTGGA AATTAAG

The mutagenesis reaction was performed as described above with the $V_H$ oligonucleotides except that the $V_L$ oligonucleotides 1 to 5 were employed (SEQ ID NOS:14 to 18, respectively). The reaction was electroporated into *E. coli* strain DH10B and filter lifts probed with either goat anti-human kappa chain antibody conjugated to alkaline phosphatase or a goat anti-human Fab antibody using an alkaline phosphatase conjugated rabbit anti-goat secondary reagent for detection. Positive clones co-expressing both $V_H$ and $V_L$ gene sequences were selected (160 total) and used to infect *E. coli* strain MK30-3 for preparing soluble Fab fragments.

The soluble Fab fragments were screened for binding to $\alpha_v\beta_3$ in an ELISA assay. Four clones that were shown from the ELISA to strongly bind $\alpha_v\beta_3$ were identified and further characterized. These clones were termed huLM609M13-34, 54, 55 and 145. All four clones were plaque purified and three independent subclones from each clone was used to prepare Fab fragments for additional binding analysis to $\alpha_v\beta_3$ by ELISA.

In this additional ELISA, duplicate plates were coated with $\alpha_v\beta_3$ ligand and incubated with the huLM609 periplasmic samples. In one plate, bound huLM609 Fab was detected with goat anti-human kappa chain antibody conjugated to alkaline phosphatase and in the other plate bound huLM609 Fab was detected with 7F11-alkaline phosphatase conjugate, the monoclonal antibody recognizing the decapeptide tag. Subclones huLM609M13-34-1, 2 and 3 and huLM609M13-145-1, 2 and 3 all yielded double positive signals indicating that the Fabs contain functional $V_H$ and $V_L$ polypeptides. These results were confirmed in an ELISA assay on M21 cells, a cell line that expresses the integrin $\alpha_v\beta_3$.

DNA sequence analysis of subclones huLM609M13-34-3 and huLM609M13-145-3 revealed mutations introduced into the library by errors due to oligonucleotide synthesis or by errors arising during PCR amplification. These mutations were corrected in clone huLM609M13-34-3 by site-directed mutagenesis. In the light chain sequence the following corrections were made: His36 to Tyr36 and Lys18 to Arg18. In the heavy chain sequence the following corrections were made: Glu1 to Gln1, Asn3 to Gln3, Leu11 to Val11. Additionally, during the construction of LM609 grafted molecules, residue 28 from the heavy chain was considered to be a non-critical framework residue and the human residue (Thr28) was retained. Subsequently, however, it has been determined that residue 28 can be considered part of the CDR. Therefore, residue 28 was converted to the corresponding mouse residue at that position (Ala28) using site directed mutagenesis with the oligonucleotide 5'-GCT ACT GAA GGC GAA TCC AGA G-3' (SEQ ID NO:29). This change was later determined to not provide benefit over the human framework threonine at this site, and the threonine was retained. The final grafted LM609 clone was designated huLM609M13 1135-4 and is termed herein Vitaxin. The DNA sequence of clone Vitaxin is shown in FIGS. 2A and 2B.

EXAMPLE III

Functional Characterization of Vitaxin

This Example shows the characterization of Vitaxin's binding specificity, affinity and functional activity in a number of in vitro binding and cell adhesion assays.

The binding specificity of Vitaxin for the integrin $\alpha_v\beta_3$ was initially assessed by measuring binding to $\alpha_v\beta_3$ and its cross-reactivity to other $\alpha_v$- or $\beta_3$-containing integrins. Specifically, binding specificity was assessed by measuring binding to $\alpha_{11b}\beta_3$, the major integrin expressed on platelets, and to $\alpha_v\beta_5$, an integrin found prevalent on endothelial cells and connective tissue cell types.

Briefly, to determine crossreactivity, integrins were coated onto an ELISA plate and a series of antibody dilutions were measured for Vitaxin binding activity against $\alpha_v\beta_3$ and the other integrins. The integrins $\alpha_v\beta_3$ and $\alpha_v\beta_5$ were isolated by affinity chromatography as described by Cheresh (1987), supra, and Cheresh and Spiro (1987), supra. $\alpha_{11b}\beta_3$ was purchased from CalBiochem. Briefly, an LM609 affinity column (Cheresh and Spiro (1987), supra) was used to isolate $\alpha_v\beta_3$ from an octylglucoside human placental lysate, whereas an anti-$\alpha_v$ affinity column was used to isolate $\alpha_v\beta_5$ from the $\alpha_v\beta_3$-depleted column flow through. Antibody binding activity was assessed by ELISA using a goat anti-human IgG-alkaline phosphatase conjugate. As a control, a purified human $IgG_1$ antibody was used since Vitaxin contains a human $IgG_1$ backbone.

Figure 4A:
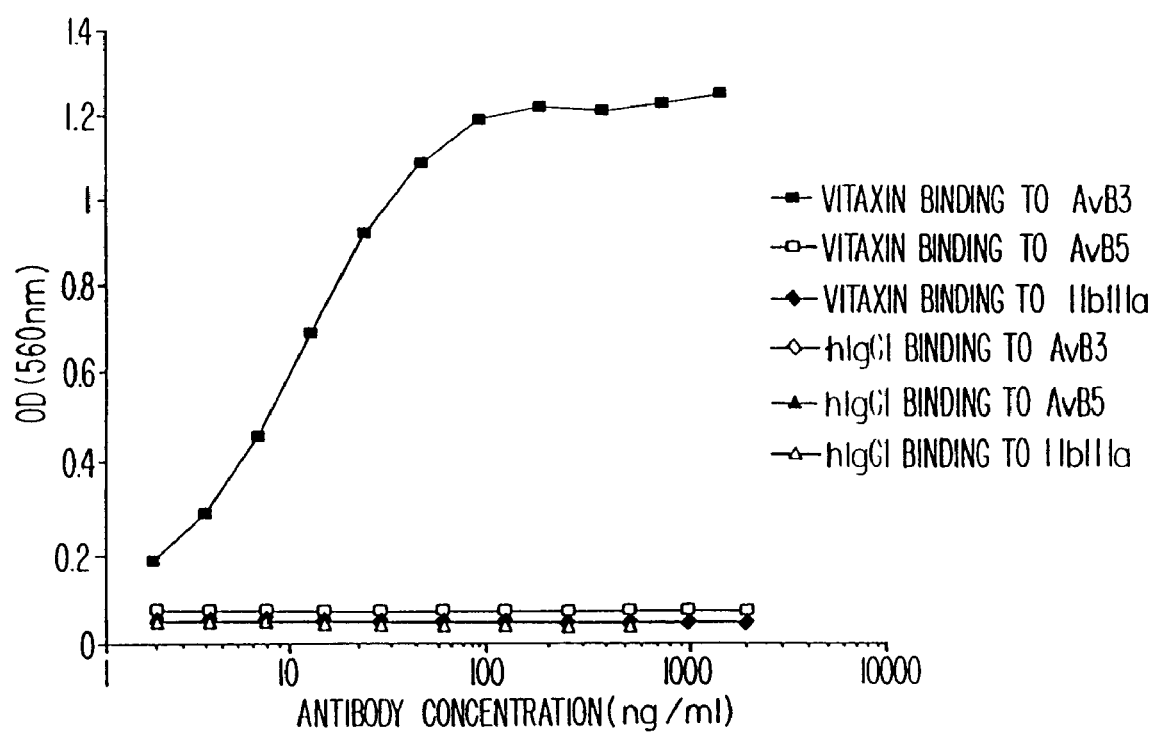
FIG. 4A shows specific binding of Vitaxin to the integrin $\alpha_v\beta_3$ compared to integrins $\alpha_{IIb}\beta_3$ and $\alpha_v\beta_5$.

The results of this assay are shown in FIG. 4A and reveal that Vitaxin specifically binds to $\alpha_v\beta_3$ with high affinity. There was no detectable binding to the other $\alpha_v$- or $\beta_3$-containing integrins at antibody concentrations over 1.0 mg/ml.

In a further series of binding studies, the binding affinity and specificity was assessed in a competitive binding assay with the parental LM609 antibody against $\alpha_v\beta_3$. Competitive binding was measured in an ELISA assay as described above with LM609 being the labeled antibody. Binding of LM609 was determined in the presence of increasing concentrations of Vitaxin competitor. Alternatively, the control competitor antibody was again a human $IgG_1$.

Figure 4B:
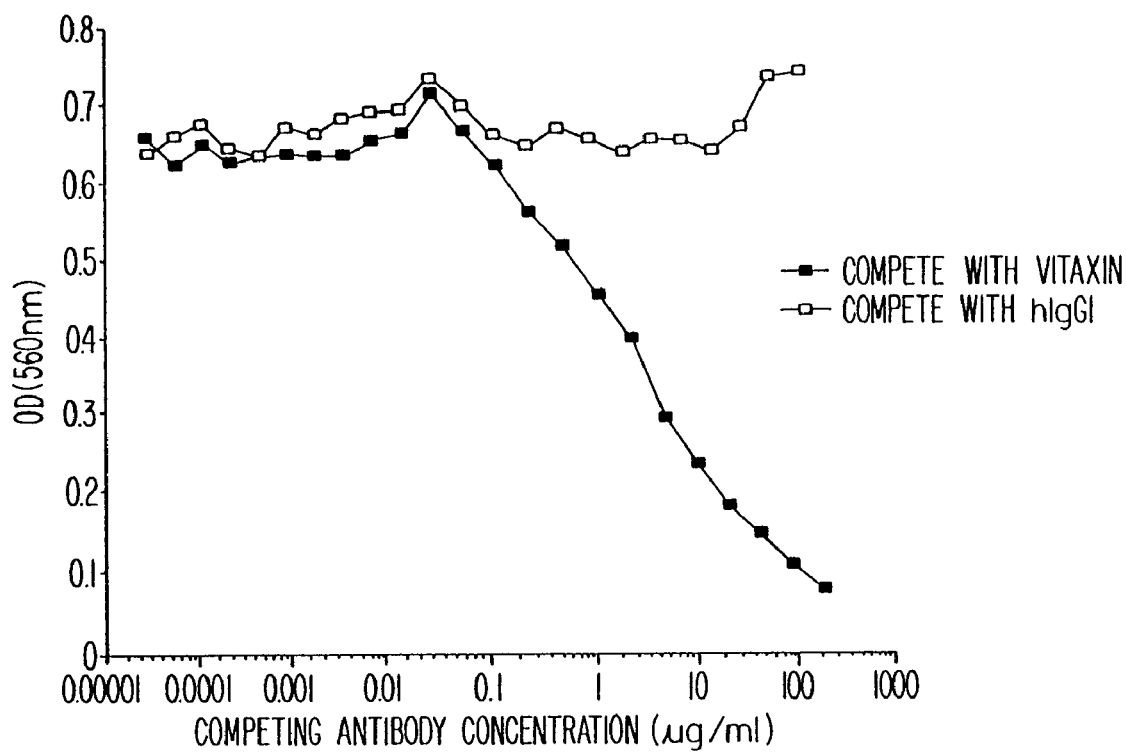
FIG. 4B shows the competitive inhibition of LM609 binding to $\alpha_v\beta_3$ by Vitaxin.

The results of this competition are presented in FIG. 4B and show that specific inhibition of LM609 binding can be observed at Vitaxin concentrations of over 0.1 µg/ml. Almost complete inhibition is observed at Vitaxin concentrations greater than 100 µg/ml. This level of competitive inhibition indicates that the parental monoclonal antibody LM609 and the grafted version Vitaxin exhibit essentially identical specificity.

Binding affinity and specificity were also assessed by measuring the inhibitory activity of Vitaxin on $\alpha_v\beta_3$ binding to fibrinogen. For these studies, $\alpha_v\beta_3$ was plated onto ELISA plates as described above for the Vitaxin/$\alpha_v\beta_3$ binding studies. Inhibitory activity of Vitaxin was determined by measuring the amount of bound biotinylated fibrinogen in the presence of increasing concentrations of Vitaxin or control antibody. Briefly, fibrinogen was purchased from CalBiochem and biotinylated with N-hydroxysuccinimidobiotin as described by the manufacturer (Pierce Life Science and Analytical Research). Streptavidin alkaline phosphatase was used to detect the bound fibrinogen.

Figure 4C:
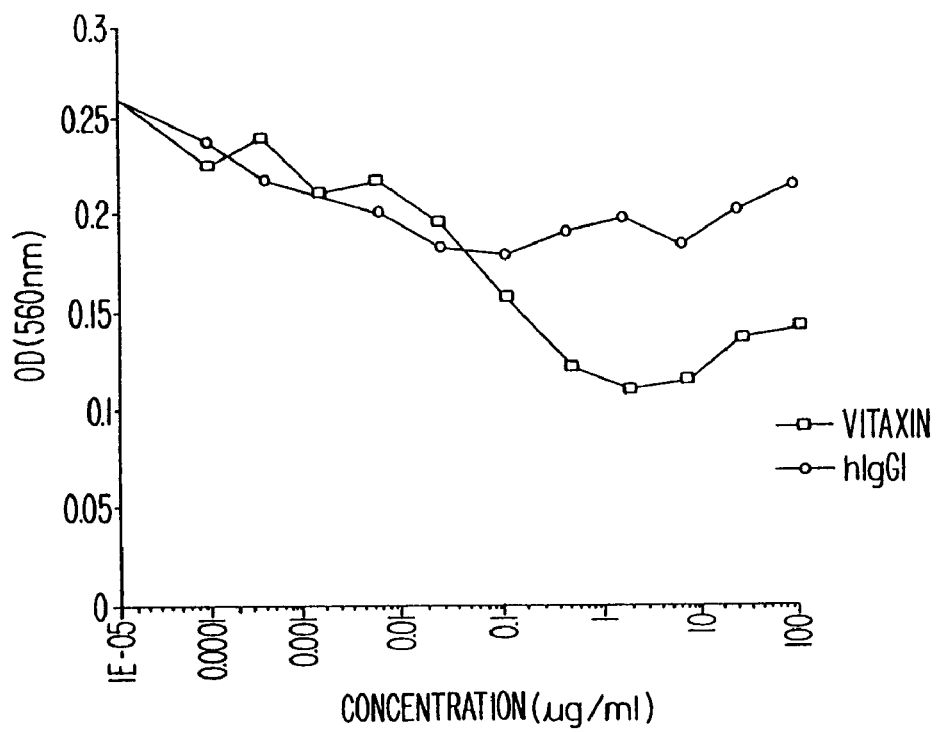
FIG. 4C shows the competitive inhibition of fibrinogen binding to $\alpha_v\beta_3$ by Vitaxin.

The results of this assay are presented in FIG. 4C and reveal a specific binding inhibition at Vitaxin concentrations higher than about 0.1 µg/ml. These results, combined with those presented above showing specific binding of Vitaxin to $\alpha_v\beta_3$ and competitive inhibition of LM609, demonstrate that Vitaxin maintains essentially all of the binding characteristics and specificity exhibited by the parental murine monoclonal antibody LM609. Described below are additional functional studies which corroborate these conclusions based on in vitro binding assays.

Additional functional studies were performed to further assess the specificity of Vitaxin binding. These studies were directed to the inhibition of integrin $\alpha_v\beta_3$ binding in cell adhesion assays. Endothelial cell adhesion events are an important component in the angiogenic process and inhibition of $\alpha_v\beta_{3}\alpha_v\beta_{3v}$ is known to reduce the neovascularization of tumors and thereby reduce the rate of tumor growth. The inhibition of $\alpha_v\beta_3$-mediated cell attachment by Vitaxin in these assays is indicative of the inhibitory activity expected when this antibody is used in situ or in vivo.

Briefly, $\alpha_v\beta_3$-positive M21 melanoma cells grown in RPMI containing 10% FBS were used for these cell binding assays. Cells were released from the culture dish by trypsinization and re-suspended in adhesion buffer at a concentration of $4\times10^5$ cells/ml (see below). Vitaxin, LM609 or purified human $IgG_1$ (control antibody), were diluted to the desired concentration in 250 µl adhesion buffer (10 mM Hepes, 2 mM $MgCl_2$, 2 mM $CaCl_2$, 0.2 mM $MnCl_2$, and 1% BSA in Hepes buffered saline at pH 7.4) and added to wells of a 48-well plate precoated with fibrinogen. The fibrinogen was isolated as described above. Each well was coated with 200 µl fibrinogen at a concentration of 10 µg/ml for 1 hour at 37° C. For the assay, an equal volume of cells (250 µl) containing Vitaxin, LM609 or isotype matched control antibody was added to each of the wells, mixed by gentle shaking and incubated for 20 minutes at 37° C. Unbound cells were removed by washing with adhesion buffer until no cells remained in control wells coated with BSA alone. Bound cells were visualized by staining with crystal violet which was subsequently extracted with 100 µl acetic acid (10%) and quantitated by determining the absorbance of the solubilized dye at 0.560 nm.

Figure 5A:
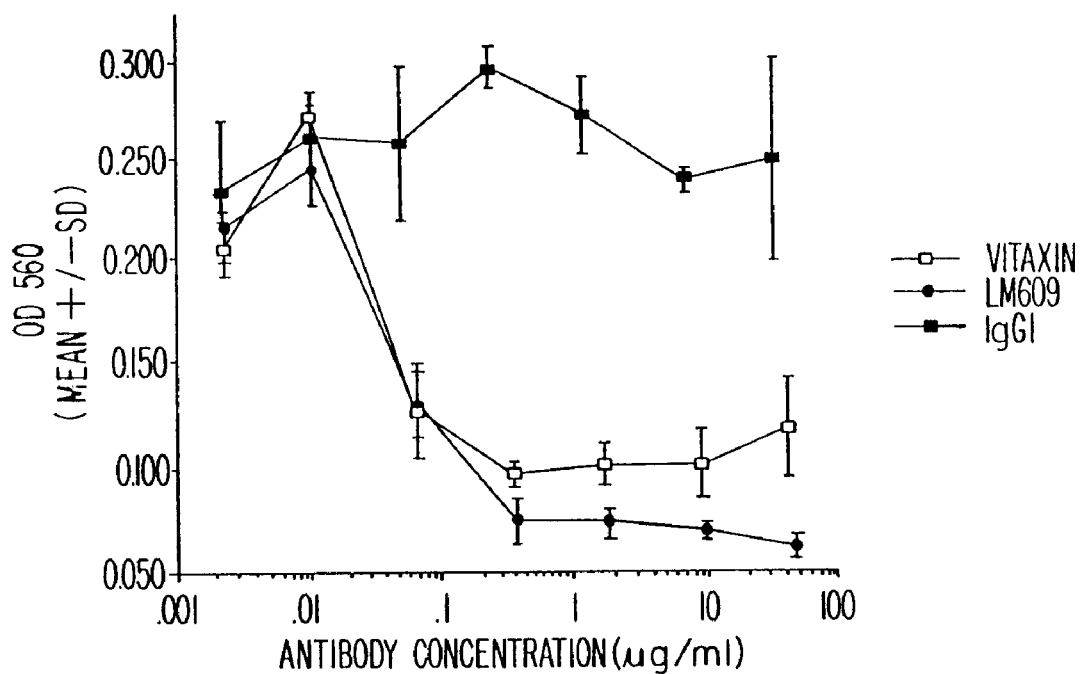
FIG. 5 shows the inhibition of $\alpha_v\beta_3$-mediated cell attachment (5A) and migration (5B) by Vitaxin.
Figure 5B:
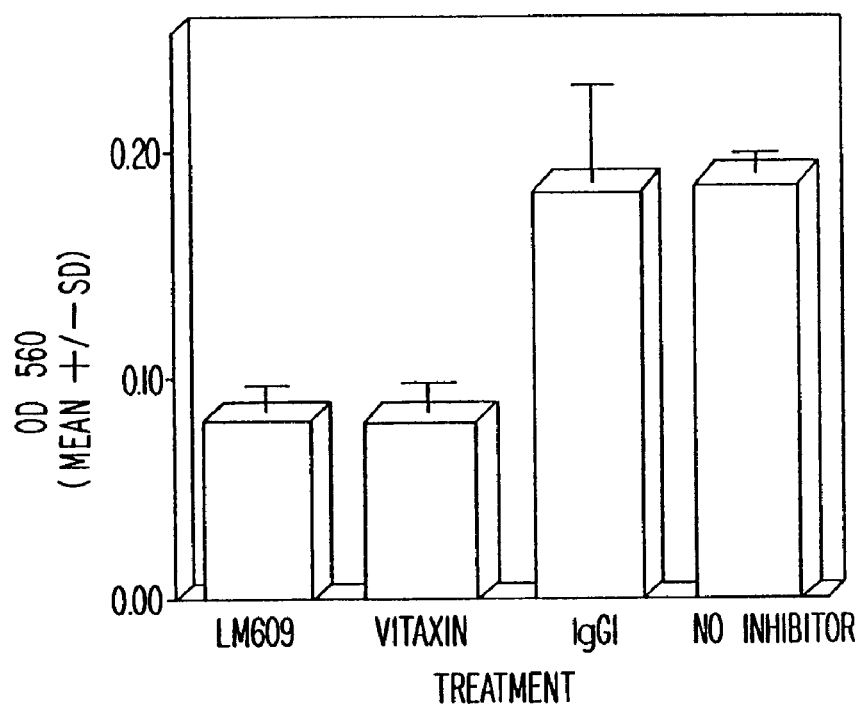

The results of this assay are shown in FIG. 5A and reveal that both Vitaxin and parental antibody LM609 inhibit M21 cell adhesion to fibrinogen over the same concentration range. The inhibitory concentration for 50% maximal adhesion was calculated to be about 50 ng/ml. Specificity of Vitaxin was shown by the lack of inhibition observed by the control $IgG_1$ antibody.

In addition to the above cell adhesion results, the inhibitory activity of Vitaxin was also tested in an endothelial cell migration assay. In this regard, the transwell cell migration assay was used to assess the ability of Vitaxin to inhibit endothelial cell migration (Choi et al., *J. Vascular Surg.*, 19:125-134 (1994) and Leavesly et al., *J. Cell Biol*, 121:163-170 (1993)).

Briefly, human umbilical vein endothelial cells in log phase and at low passage number were harvested by gentle trypsinization, washed and resuspended at a concentration of $2\times10^6$ cells/ml in 37° C. HBS containing 1% BSA (20 mM HEPES, 150 mM NaCl, 1.8 mM $CaCl_2$, 1.8 mM $MgCl_2$, 5 mM KCl, and 5 mM glucose, pH 7.4). Antibodies (Vitaxin, LM609, and $IgG_1$ control) were diluted to 10 µg/ml from stock solutions. Antibodies were added to cells in a 1:1 dilution (final concentration of antibodies=5 µg/ml; final concentration of cells=$1\times10^6$ cells/ml) and incubated on ice for 10-30 minutes. The cell/antibody suspensions (200 µl to each compartment) were then added to the upper compartments of a Transwell cell culture chamber (Corning Costar), the lower compartments of which had been coated with 0.5 ml of 10

μg/ml vitronectin (in HBS). Vitronectin serves as the chemoattractant for the endothelial cells. The chambers were placed at 37° C. for 4 hours to allow cell migration to occur.

Visualization of cell migration was performed by first removing the remaining cells in the upper compartment with a cotton swab. Cells that had migrated to the lower side of the insert were stained with crystal violet for 30 minutes, followed by solubilization in acetic acid and the absorbance of the dye was measured at a wavelength of 550 nm. The amount of absorbance is directly proportional to the number of cells that have migrated from the upper to the lower chamber. The results of the assay are presented in FIG. 7B. Both Vitaxin and the parental antibody LM609 yielded essentially identical inhibitory results. Specifically, Vitaxin and LM609 inhibited about 60% of the vitronectin-induced migration of endothelial cells compared to the $IgG_1$ control and to a sample with no inhibitor.

EXAMPLE IV

Vitaxin-Mediated Inhibition of $\alpha_v\beta_3$ in Animal Models

This Example describes the inhibition of tumor growth by Vitaxin in two animal models. Tumor growth was inhibited by inhibiting at least $\alpha_v\beta_3$-mediated neovascularization with Vitaxin.

The first model measures angiogenesis in the chick chorioallantoic membrane (CAM). This assay is a well recognized model for in vivo angiogenesis because the neovascularization of whole tissue is occurring. Specifically, the assay measures growth factor induced angiogenesis of chicken CAM vessels growing toward the growth factor-impregnated filter disk or into the tissue grown on the CAM. Inhibition of neovascularization is based on the amount and extent of new vessel growth or on the growth inhibition of tissue on the CAM. The assay has been described in detail by others and has been used to measure neovascularization as well as the neovascularization of tumor tissue (Ausprunk et al., *Am. J. Pathol.*, 79:597-618 (1975); Ossonski et al. *Cancer Res.*, 40:2300-2309 (1980); Brooks et al. *Science*, 264:569-571 (1994a) and Brooks et al. *Cell*, 79:1157-1164 (1994b).

Briefly, for growth factor induced angiogenesis filter disks are punched from #1 Whatman Qualitative Circles using a skin biopsy punch. Disks are first sterilized by exposure to UV light and then saturated with varying concentrations of TNF-α or HBSS as a negative control (for at least 1 hour) under sterile conditions. Angiogenesis is induced by placing the saturated filter disks on the CAMS.

Inhibition of angiogenesis is performed by treating the embryos with various amounts of Vitaxin and controls (antibody or purified human $IgG_1$). The treatments are performed by intravenous injection approximately 24 hours after disk placement. After 48 hours, CAMs are dissected and angiogenesis is scored on a scale of 1-4. HBSS saturated filter disks are used as the negative control, representing angiogenesis that may occur in response to tissue injury in preparing CAMs, and, values for these CAMS are subtracted out as background. Purified human $IgG_1$ is used as the negative control for injections since Vitaxin is of the human $IgG_1$ subclass. Vitaxin was found to inhibit TNF-α induced angiogenesis in a dose dependent manner. Maximal inhibition occurred with a single dose of Vitaxin at 300 μg which resulted in greater than 80% inhibition compared to the human $IgG_1$ control.

In addition to the above described CAM assay using growth factor-induced neovascularization, additional studies were performed utilizing tumor-induced neovascularization. For these assays, angiogenesis was induced by transplantating of $\alpha_v\beta_3$-negative tumor fragments into the CAMs. The use of $\alpha_v\beta_3$-negative tumor fragments ensures that any inhibition of tumor growth is due to the inhibition of $\alpha_v\beta_3$-mediated neovascularization by CAM-derived endothelial cells and not to adhesion events mediated by $\alpha_v\beta_3$ present on the tumor cells.

Inhibition of tumor growth was assessed by placing a single cell suspension of FG ($8\times10^6$ cells, pancreatic carcinoma) and HEp-3 cells ($5\times10^5$ cells, laryngeal carcinoma) onto CAMs in 30 μl. One week later, tumors are removed and cut into approximately 50 mg fragments at which time they are placed onto new CAMs. After 24 hours of this second placement embryos are injected intravenously with Vitaxin or human $IgG_1$ as a negative control. The tumors are allowed to grow for about 7 days following which they are removed and weighed.

Figure 6A:
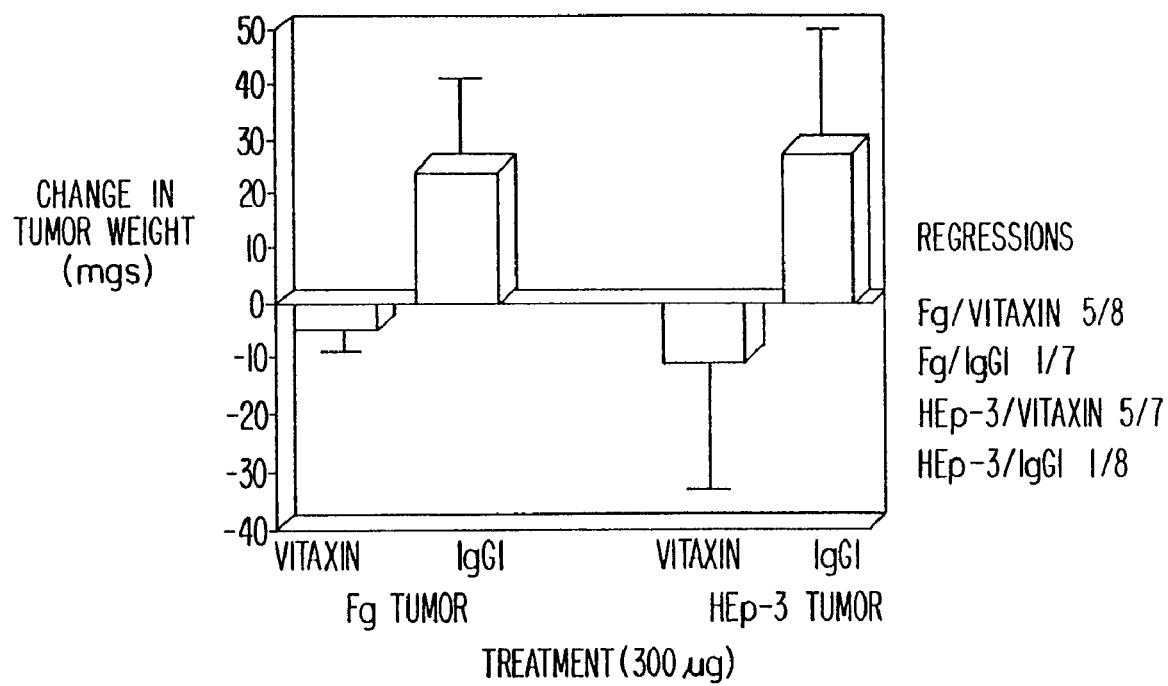
FIG. 6A shows the inhibition of the $\alpha_v\beta_3$-negative Fg and HEp-3 human tumor fragments grown on chick chorioallantoic membranes (CAMs) following Vitaxin treatment.

The results of Vitaxin treatment on the neovascularization of tumors is shown in FIG. 6A. The data is expressed as a mean change in tumor weight and demonstrate that Vitaxin is able to inhibit the growth of $\alpha_v\beta_3$-negative tumors such as FG and HEp-3 tumor fragments. More specifically, there was a mean weight change for Vitaxin treated FG tumor fragments of −5.38 whereas a change of −11.0 was observed for Vitaxin treated HEp-3 tumors. The $IgG_1$ controls exhibited positive mean weight changes of 25.29 and 28.5 for the FG and HEp-3 tumor fragments, respectively. These results were obtained following a single intravenous injection.

In a second animal model, the inhibition of Vx2 carcinoma cells in rabbits was used as a measure of Vitaxin's inhibitory effect on tumors. The Vx2 carcinoma is a transplantable carcinoma derived from a Shope virus-induced papilloma. It was first described in 1940 and has since been used extensively in studies on tumor invasion, tumor-host interactions and angiogenesis. The Vx2 carcinoma is fibrotic in nature, highly aggressive, and exhibits features of an anaplastic type carcinoma. Propagation of Vx2 tumor is accomplished through serial transplantation in donor rabbits. Following subcutaneous transplantation, it has been reported that after an initial inflammatory reaction, host repair mechanisms set in between days 2 and 4. This repair mechanism is characterized by the formation of new connective tissue and the production of new capillaries. The newly formed capillaries are restricted to the repair zone at day 4, however, by day 8 they have extended to the outer region of the tumor. These characteristics and the pharmacokinetics of Vitaxin in rabbits were used to determine initial doses and scheduling of treatments for these experiments. The elimination half life of Vitaxin in animal serum dosed at 1, 5, and 10 mg/kg was found to be 38.9, 60.3, and 52.1 hours, respectively.

Growth of Vx2 tumors in the above animal model was used to study the effect of Vitaxin after early administration on primary tumor growth in rabbits implanted subcutaneously with Vx2 carcinoma. Briefly, Vx2 tumors (50 mg) were transplanted into the inner thigh of rabbits through an incision between the skin and muscle. Measurements of the primary tumor were taken throughout the experiment through day 25. At day 28 after the transplantation animals were sacrificed and tumors were excised and weighed. By day 28, tumors became extremely irregular in shape and as a result, measurements became difficult and were not reflective of tumor volume. Therefore measurements were assessed only through day 25.

In a first study, rabbits were treated starting at day 1 post tumor implantation with 5 and 1 mg/kg Vitaxin every four days for 28 days for a total of 7 doses). In both groups, inhibition of tumor growth was observed. In a second series of studies, rabbits were treated beginning at day 7 post tumor implantation as described above for a total of 5 doses. Inhibition of tumor growth was also observed.

It should be noted that administering a grafted antibody as a repeat dose treatment to rabbits might generate an immune response that can have a neutralizing effect on Vitaxin thus potentially comprising efficacy. Preliminary data suggest that approximately 25-50% of the animals develop such a response.

Figure 6B:
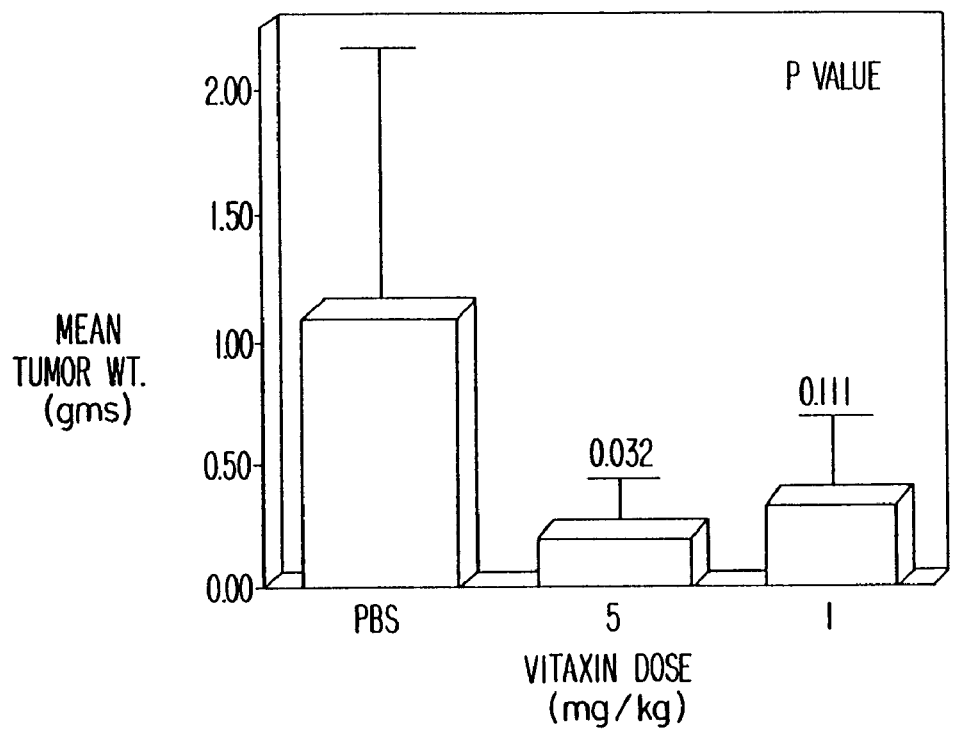
FIG. 6B shows the growth inhibition of Vx2 carcinomas implanted subcutaneously in rabbits at two different Vitaxin doses administered 1 day post implantation.
Figure 6C:
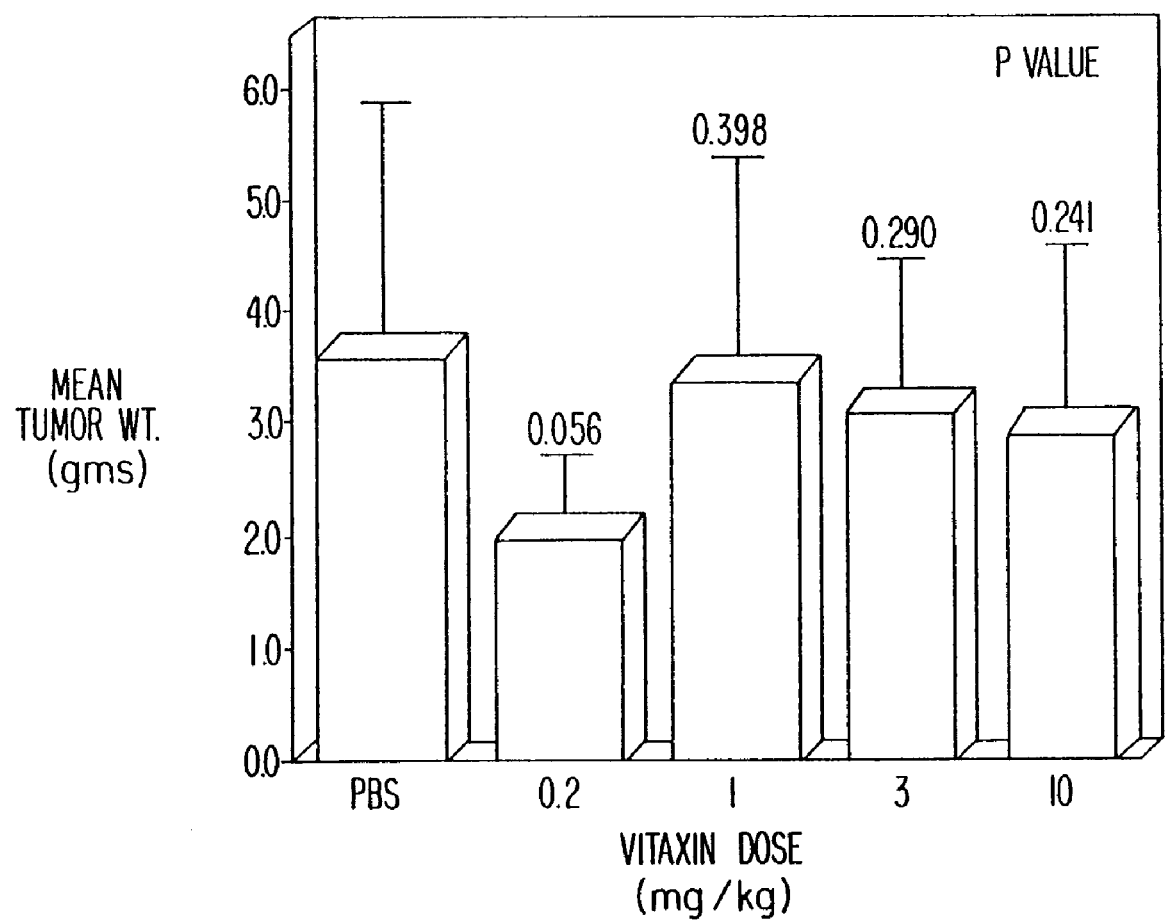
FIG. 6C similarly shows Vx2 tumor growth inhibition as in FIG. 6B, except that four different Vitaxin doses were administered beginning at 7 days post implantation.

The results of each of the Vitaxin treatments described above is shown in FIGS. 6B and 6C. In the rabbits receiving treatments on day 1, inhibition of tumor growth was observed in both the 1 mg/kg and the 5 mg/kg dosing groups compared to the control PBS treated control. Specifically, a growth inhibition of about 67 and 80% was observed, respectively, as measured by the mean tumor weight. A lesser degree of inhibition was observed in animals that began Vitaxin treatment on day 7 post implantation. These results are shown in FIG. 6C. In all cases, inhibition of tumor growth was not see at Vitaxin concentrations lower than 0.2 mg/kg.

EXAMPLE V

Construction of LM609 Grafted Functional Antibody Fragments

This Example shows the construction of functional LM609 grafted antibody fragments in which only the CDRs have been transferred from the LM609 donor antibody to a human acceptor framework.

CDR grafting of LM609 to produce a functional antibody fragment was accomplished by the methods set forth below. These procedures are applicable for the CDR grafting of essentially any donor antibody where amino acid residues outside of the CDRs from the donor antibody are not desired in the final grafted product.

Briefly, the protein sequence of the LM609 antibody, was determined by cloning and sequencing the cDNA that encodes the variable regions of the heavy and light chains as described in Example I. The CDRs from the LM609 donor antibody were identified and grafted into homologous human variable regions of a human acceptor framework. Identification of CDR regions were based on the combination of definitions published by Kabat et al., and MacCallum et al.

The boundaries of the CDR regions have been cumulatively defined by the above two publications and are residues 30-35, 47-66 and 97-106 for CDRs 1, 2 and 3, respectively, of the heavy chain variable region and residues 24-36, 46-56, and 89-97 for CDRs 1, 2 and 3, respectively, of the light chain variable region. Non-identical donor residues within these boundaries but outside of CDRs as defined by Kabat et al. were identified and were not substituted into the acceptor framework. Instead, functional non-donor amino acid residues were identified and substituted for certain of these non-identical residues.

As described below, the only non-identical residue outside of the CDRs as defined by Kabat et al. but within the CDRs as defined above is at position 49 of the LM609 light chain. To identify functional non-donor amino acids at this position, a library of nineteen antibodies was constructed that contained all non-donor amino acids at position 49 and then screened for binding activity against $\alpha_v\beta_3$.

Human immunoglobulin sequences were identified from the Brookhaven Protein Data Bank-Kabat Sequences of Proteins of Immunological Interest database (release 5.0). Human framework sequences showing significant identity to the murine LM609 variable region gene sequences were selected for receiving the LM609 CDRs. Human heavy chain variable region M72 'CL had 88% identity to frameworks 1, 2 and 3 of LM609 heavy chain and human light chain V region LS1 'CL had 79% identity to frameworks 1, 2 and 3 of LM609 light chain. With the exclusion of non-identical residues outside of the CDRs as defined by Kabat et al. murine LM609 CDR sequences as defined by Kabat et al. and MacCallum et al. were grafted onto the human frameworks. Using this grafting scheme, the final grafted product does not contain any amino acid residues outside of the CDRs as defined by Kabat et al. which are identical to an LM609 amino acid at the corresponding position (outside of residues: 31-35, 50-66 and 99-106 for CDRs 1, 2 and 3, respectively, of the heavy chain variable region and residues 24-34, 50-56, and 89-97 for CDRs 1, 2 and 3, respectively, of the light chain variable region). Moreover, no intermediates are produced which contain an amino acid residue outside of the CDRs as defined by Kabat et al. which are identical to the LM609 amino acid at that position. The CDR grafting procedures are set forth below.

Full-length CDR grafted variable region genes were synthesized by PCR using long overlapping oligonucleotides as described previously in Example II. The heavy chain variable region oligonucleotides were those described previously as SEQ ID NOS:9-13. The light chain variable region oligonucleotides were synthesized so as to contain the CDR grafted variable region as well as a stop codon at position 49. The five oligonucleotides for the light chain LM609 grafted variable region are show as SEQ ID NOS:23-27 where the second oligonucleotide in the series contains the stop codon at position 49 (SEQ ID NO:24). The nucleotide sequences of oligonucleotides used to construct LM609 grafted light chain variable region is shown in Table 7.

TABLE 7

Oligonucleotides Used to Construct LM609 Grafted Light Chain Variable Region

SEQ ID NO: 23
GAGATTGTGC TAACTCAGTC TCCAGCCACC CTGTCTCTCA
GCCCAGGAGA AAGGGCGACT CTTTCCTGCC AGGCCAGCCA
AAGTATT

SEQ ID NO: 24
TTAGATGAGA AGCCTTGGGG CTTGACCAGG CCTTTGTTGA
TACCAGTGTA GGTGGTTGCT AATACTTTGG CTGGC

SEQ ID NO: 25
CCAAGGCTTC TCATCTAATA TCGTTCCCAG TCCATCTCTG
GGATCCCCGC CAGGTTCAGT GGCAGTGGAT CAGGGACAGA TTTC

SEQ ID NO: 26
GCTGCCACTC TGTTGACAGT AATAGACTGC AAAATCTTCA
GGCTCCAGAC TGGAGATAGT GAGGGTGAAA TCTGTCCCTG A

SEQ ID NO:27
CAACAGAGTG GCAGCTGGCC TCACACGTTC GGAGGGGGA
CCAAGGTGGA AATTAAG

All long oligonucleotides were gel purified. CDR grafting of the LM609 heavy chain variable region was constructed by mixing 5 overlapping oligonucleotides (SEQ ID NOS:9-13), at equimolar concentrations, in the presence of annealing PCR primers containing at least 18 nucleotide residues complementary to vector sequences for the efficient annealing of the amplified V region product to the single-stranded vector. The annealed mixture was fully converted to a double-stranded molecule with T4 DNA polymerase plus dNTPs and ligated with T4 ligase. The mutagenesis reaction (1 μl) was electroporated into *E. coli* strain DH10B (BRL), titered onto a lawn of XL-1 (Stratagene, Inc.) and incubated until plaques formed. Replica filter lifts were prepared and plaques containing $V_H$ gene sequences were screened either by hybridization with a digoxigenin-labeled oligonucleotide complementary to LM609 heavy chain CDR 2 sequences or reactivity with 7F11-alkaline phosphatase conjugate, a monoclonal antibody raised against the decapeptide sequence Tyr Pro Tyr Asp Val Pro Asp Tyr Ala Ser (SEQ ID NO:28) appended to the carboxy terminus of the vector $CH_1$ domain (Biosite, Inc., San Diego, Calif.).

Fifty clones that were double-positive were pooled and used to prepare uridinylated template for hybridization mutagenesis with the amplified CDR grafted LM609 $V_L$ product constructed in a similar fashion using the five overlapping oligonucleotides shown as SEQ ID NOS:23-27. The mutagenesis reaction was electroporated into *E. coli* strain DH10B. Randomly picked clones were sequenced to identify a properly constructed template for construction of the non-donor library at position 49. This template was prepared as a uridinylated template and an oligonucleotide population of the following sequence was used for site directed mutagenesis.

GGGAACGATA-19aa-GATGAGAAGC

The sequence 19aa in the above primer (SEQ ID NO:30) represents the fact that this primer specifies a sequence population consisting of 19 different codon sequences that encode each of the 19 non-donor amino acids. These amino acids are those not found at position 49 of LM609 and include all amino acids except for Lys. Clones that resulted from this mutagenesis were picked and antibody expressed by these clones were prepared. These samples were then screened for binding to $\alpha_v\beta_3$ in an ELISA assay. Clones having either Arg or Met amino acids in position 49 were functionally identified. The nucleotide and amino acid sequence of the LM609 grafted heavy chain variable region is show in FIG. 1A (SEQ ID NOS:1 and 2, respectively). The nucleotide and amino acid sequence of the LM609 grafted light chain variable region is shown in FIG. 7 (SEQ ID NOS:31 and 32, respectively).

EXAMPLE VI

Generation of LM609 Grafted Antibodies Having Enhanced Activity

This example shows in vitro maturation of LM609 grafted antibody to obtain antibody variants having increased affinity to $\alpha_v\beta_3$ relative to the parent LM609 grafted antibody.

To optimize the affinity of LM609 grafted antibody in vitro, an M13 phage system was used, which permits the efficient synthesis, expression, and screening of libraries of functional antibody fragments (Fabs). The contribution of each of the six CDRs of the Ig heavy and light chains was assessed. The CDRs were defined broadly based on a combination of sequence variability and antibody structural models (Kabat et al., *J. Biol. Chem.* 252:6609-6616 (1977); Chothia et al., supra; MacCallum et al., supra). Thus, one library was constructed for each CDR, with the exception of H2 which was split into two libraries due to its long (20 amino acids) length. The variable region frameworks which harbored the mutated CDRs were the heavy chain variable region shown in FIG. 1*a* (SEQ ID NO:2) and the light chain variable region shown in FIG. 7 (SEQ ID NO:32).

CDRs were chosen from the heavy chain variable region shown in FIG. 1*a* (SEQ ID NO:2) and the light chain variable region shown in FIG. 7 (SEQ ID NO:32). Briefly, utilizing the numbering system of Kabat et al., supra, the residues chosen for mutagenesis of the CDRs (Table 9) were: $Gln^{24}$-$Tyr^{36}$ in light chain CDR1 (L1); $Leu^{46}$-$Ser^{56}$ in light chain CDR2 (L2); $Gln^{89}$-$Thr^{97}$ in light chain CDR3 (L3); $Gly^{26}$-$Ser^{35}$ in heavy chain CDR1 (H1); $Trp^{47}$-$Gly^{65}$ in heavy chain CDR2 (H2); and $Ala^{93}$-$Tyr^{102}$ in heavy chain CDR3 (H3). Libraries were created for each CDR, with the oligonucleotides designed to mutate a single CDR residue in each clone. Due to the extended length of H2, two libraries mutating residues 47-55 (H2a) and 56-65 (H2b), respectively, were constructed to cover this region.

The template for generating light chain CDR3 mutants contained Gly at position 92. However, it was subsequently determined that position 92 of the light chain CDR3 was inadvertently deduced to be a Gly, resulting in humanized LM609 grafted antibodies being constructed with Gly at that position. It was later realized that the original LM609 sequence contained an Asn at position 92. Using the methods described herein to introduce mutations into CDRs of an LM609 grafted antibody, an LM609 grafted antibody having Asn at position 92 of light chain CDR3 was found to have $\alpha_v\beta_3$ binding activity (see Table 9), confirming the identification of $Asn^{92}$ as a functional LM609 grafted antibody. Thus, antibodies containing light chain CDR3 having Gly or Asn at position 92 are active in binding $\alpha_v\beta_3$.

Oligonucleotides encoding a single mutation were synthesized by introducing NN(G/T) at each CDR position as described previously (Glaser et al., supra). The antibody libraries were constructed in M131XL604 vector by hybridization mutagenesis as described previously, with some modifications (Rosok et al., *J. Biol. Chem.* 271:22611-22618 (1996); Huse et al., *J. Immunol.* 149:3914-3920 (1992); Kunkel, *Proc. Natl. Acad. Sci. USA* 82:488-492 (1985), Kunkel et al., *Methods Enzymol.* 154:367-382 (1987)). Briefly, the oligonucleotides were annealed at a 20:1 molar ratio to uridinylated LM609 grafted antibody template (from which the corresponding CDR had been deleted) by denaturing at 85° C. for 5 min, ramping to 55° C. for 1 h, holding at 55° C. for 5 min, then chilling on ice. The reaction was extended by polymerization electroporated into DH10B and titered onto a lawn of XL-1 Blue. The libraries consisted of pools of variants, each clone containing a single amino acid alteration in one of the CDR positions. Utilizing codon-based mutagenesis, every position in all of the CDRs was mutated, one at a time, resulting in the subsequent expression of all twenty amino acids at each CDR residue (Glaser et al., supra). The CDR libraries ranged in size from 288 (L3) to 416 (L1) unique members and contained a total of 2336 variants.

To permit the efficient screening of the initial libraries, a highly sensitive plaque lift assay, termed capture lift, was employed (Watkins et al., *Anal. Biochem.* 256 (1998)). Briefly, phage expression libraries expressing LM609 grafted antibody variants were initially screened by a modified plaque lift approach, in which the nitrocellulose was pre-coated with goat anti-human kappa antibody and blocked with bovine serum albumin prior to application to the phage-infected bacterial lawn. Following the capture of phage-expressed LM609 grafted antibody variant Fabs, filters were incubated with 1.0 μg/ml biotinylated $\alpha_v\beta_3$ for 3 h at 4° C., washed four times, incubated with 2.3 μg/ml NeutrAvidin-alkaline phosphatase (Pierce Chemical Co.; Rockford, Ill.) for 15 min at 25° C., and washed four times. All dilutions and washes were in binding buffer. Variants that bound $\alpha_v\beta_3$ were identified by incubating the filters for 10-15 min in 0.1 M Tris, pH 9.5, containing 0.4 mM 2,2'-di-p-nitrophenyl-5,5'-diphenyl-3, 3'-(3,3'-dimethoxy-4,4'-diphenylene)ditetrazolium chloride and 0.38 mM 5-bromo-4-chloro-3-indoxyl phosphate mono-(p-toluidinium) salt (JBL Scientific, Inc.; San Luis Obispo, Calif.).

To generate biotinylated $\alpha_v\beta_3$ receptor was purified from human placenta by affinity chromatography, as described previously (Smith and Cheresh, *J. Biol. Chem.* 263:18726-18731 (1988)). To biotinylate $\alpha_v\beta_3$, purified receptor was dialyzed into 50 mM HEPES, pH 7.4, 150 mM NaCl, 1.0 mM $CaCl_2$, containing 0.1% NP-40 (binding buffer) and incubated with 100-fold molar excess sulfosuccinimidobiotin for 3 h at 4° C. The reaction was terminated by the addition of 50 mM ethanolamine.

Phage expressed LM609 grafted antibody variants were selectively captured on nitrocellulose filters coated with goat anti-human kappa chain antibody, probed with biotinylated $\alpha_v\beta_3$, and detected with NeutrAvidin-alkaline phosphatase. Initially, biotinylated $\alpha_v\beta_3$ was titrated on lifts containing phage expressing the LM609 grafted antibody parent molecule only. Subsequently, the concentration of biotinylated $\alpha_v\beta_3$ was decreased to yield a barely perceptible signal. In this way, only clones expressing higher affinity variants were readily identified during screening of the variant libraries. Following the exhaustive capture lift screening of $\geq 2500$ clones from each library, 300 higher affinity variants were identified (see Table 10). The greatest number of clones displaying improved affinity were identified in the H3 (185) and L3 (52) CDRs, though variants with improved affinity were identified in every CDR.

LM609 grafted antibody variants identified by capture lift as having $\alpha_v\beta_3$ binding activity were further characterized to determine binding affinity to $\alpha_v\beta_3$, specificity for $\alpha_v\beta_3$ over other integrins, and $\alpha_v\beta_3$ association and dissociation rates. For these assays, purified Fab of LM609 grafted antibody variants was used. Briefly, Fab was expressed as described previously and was released from the periplasmic space by sonic oscillation (Watkins et al., supra, 1997). Cells collected from one liter cultures were lysed in 10 ml 50 mM Tris, pH 8.0, containing 0.05% Tween 20. Fab was bound to a 1 ml protein A column (Pharmacia) which had been equilibrated with 50 mM glycine, pH 8, containing 250 mM NaCl, washed with the same buffer, and eluted with 10 ml of 100 mM glycine, pH 3, into one-tenth volume 1 M Tris, pH 8. Purified Fab was quantitated as described previously (Watkins et al., supra, 1997).

LM609 grafted antibody variants were tested for binding to $\alpha_v\beta_3$ and specificity of binding to $\alpha_v\beta_3$ relative to $\alpha_v\beta_5$ and $\alpha_{IIb}\beta_3$. For ELISA titration of Fab on immobilized $\alpha_v\beta_3$ and the related integrins $\alpha_v\beta_5$ and $\alpha_{IIb}\beta_3$, Immulon II microtiter plates were coated with 1 µg/ml purified receptor in 20 mM Tris, pH 7.4, 150 mM NaCl, 2 mM $CaCl_2$, 1 mM $MgCl_2$, 1 mM $MnCl_2$, washed once, and blocked in 3% BSA in 50 mM Tris, pH 7.4, 100 mM NaCl, 2 mM $CaCl_2$, 1 mM $MgCl_2$ for 1 h at 25° C. Human $\alpha_{IIb}\beta_3$, purified from platelets, was obtained from Enzyme Research Laboratories, Inc. (South Bend, Ind.) and $\alpha_v\beta_5$ was purified from placental extract depleted of $\alpha_v\beta_3$, as described previously (Smith et al., *J. Biol. Chem.* 265:11008-11013 (1990)). Just prior to use, the plates were washed two times and were then incubated 1 h at 25° C. with various dilutions of Fab. The plates were washed five times, incubated 1 h at 25° C. with goat anti-human kappa-alkaline phosphatase diluted 2000-fold, washed five times, and developed as described previously (Watkins et al., supra, 1997). All dilutions and washes were in 50 mM Tris-HCl, pH 7.4, 100 mM NaCl, 2 mM $CaCl_2$, and 1 mM $MgCl_2$.

TABLE 10

Capture Lift Screening of LM609 grafted antibody CDR Libraries.

| Library | Size[1] | Screened[2] | Positives[3] | Enhanced Affinity[4] |
|---------|---------|-------------|--------------|----------------------|
| H1      | 320     | 2500        | 16           | 8                    |
| H2a     | 320     | 5000        | 26           | 7                    |
| H2b     | 320     | 5000        | 2            | 1                    |
| H3      | 320     | 5000        | 185          | 78[5]                |
| L1      | 416     | 2500        | 12           | 1                    |
| L2      | 352     | 3250        | 7            | 1                    |
| L3      | 288     | 5000        | 52           | 41                   |

[1]Number of unique clones based on DNA sequence. Thirty-two codons are used to express all twenty amino acids at each position.
[2]Phage-expressed libraries were plated on XL-1 Blue/agar lawns at 500-100 plaques per 100 mm dish.
[3]Positives are defined as clones that were identified in the initial screen, replated, and verified in a second capture lift assay.
[4]Soluble Fab was titrated against immobilized $\alpha_v\beta_3$ in an ELISA format. Based on comparison of the inflection point of the titration profiles, clones which displayed ~3-fold enhanced affinity were selected for further characterization.
[5]Of the 185 positive clones identified by capture lift, 98 were further characterized for binding to immobilized $\alpha_v\beta_3$.

Figure 8:
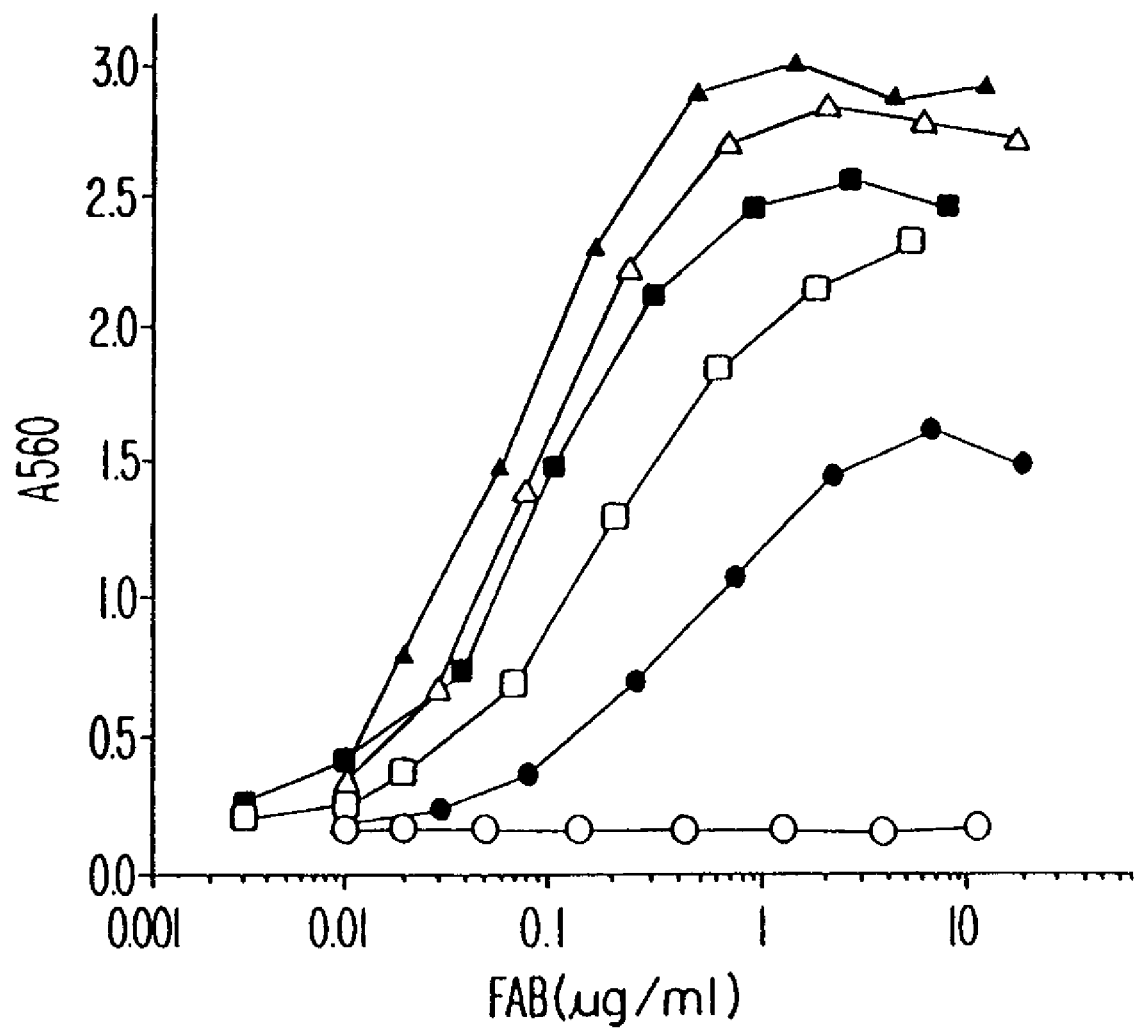
FIG. 8 shows the titration of LM609 grafted antibody variants and LM609 grafted Fab on immobilized $\alpha_v\beta_3$. Bacterial cell lysates containing LM609 grafted antibody (closed circles), LM609 grafted antibody variants with improved affinity isolated from the primary libraries (S102, closed squares; Y100, open squares; and Y101, open triangles) or from combinatorial libraries (closed triangles), or an irrelevant Fab (open circles) were titrated on immobilized $\alpha_v\beta_3$.

FIG. 8 shows titration of antibody variants and LM609 grafted antibody Fab on immobilized a, Bacterial cell lysates containing LM609 grafted antibody (closed circles), variants with improved affinity isolated from the primary libraries (S102, closed squares; Y100, open squares; and Y101, open triangles) or from the combinatorial libraries (closed triangles), or an irrelevant Fab (open circles) were titrated on immobilized $\alpha_v\beta_3$.

Comparison of the inflection points of the binding profiles obtained from titrating variants on immobilized $\alpha_v\beta_3$ demonstrated that multiple clones displayed >3-fold improved affinity, confirming the effectiveness of utilizing the capture lift in a semi-quantitative fashion (FIG. 8, compare squares and open triangles with closed circles). Based on the capture lift screening and subsequent characterization of binding to immobilized $\alpha_v\beta_3$, it was concluded that both heavy and light chain CDRs are directly involved in the interaction of $\alpha_v\beta_3$ with the LM609 grafted antibody variants.

DNA was isolated from clones displaying >3-fold enhanced binding and sequenced to identify the mutations which resulted in higher affinity. DNA sequencing was performed on isolated single-stranded DNA. The heavy and light chain variable region genes were sequenced by the fluorescent dideoxynucleotide termination method (Perkin-Elmer; Foster City, Calif.). Based on sequence analysis of 103 variants, 23 unique mutations clustered at 14 sites were identified (Table 9). The majority of the sites of beneficial mutations were found in the heavy chain CDRs, with four located in H3, and three each in H2 (2a and 2b combined) and H1. Seven distinct and beneficial amino acid substitutions were identified at a single site within H3, tyrosine residue 102. The diverse nature of the substitutions at this site suggests that tyrosine residue 102 may sterically hinder LM609 grafted antibody binding to $\alpha_v\beta_3$. In support of this, variants expressing the other aromatic amino acids (phenylalanine, histidine, and tryptophan) instead of tyrosine at residue 102 were never isolated following screening for enhanced binding.

The affinities of select variants were further characterized by utilizing surface plasmon resonance (BIAcore) to measure the association and dissociation rates of purified Fab with immobilized $\alpha_v\beta_3$. Briefly, surface plasmon resonance (BIAcore; Pharmacia) was used to determine the kinetic constants for the interaction between $\alpha_v\beta_3$ and LM609 grafted antibody variants. Purified $\alpha_1\beta_3$ receptor was immobilized to a (1-ethyl-3-(3-dimethylaminopropyl)-carbodiimide hydrochloride)/N-hydroxysuccinimide-activated sensor chip by injecting 30 μl of 15 μg/ml $\alpha_v\beta_3$ in 10 mM sodium acetate, pH 4. To obtain association rate constants ($k_{on}$), the binding rate at five different Fab concentrations, ranging from 5-40 μg/ml in 50 mM Tris-HCl, pH 7.4, 100 mM NaCl, 2 mM $CaCl_2$, and 1 mM $MgCl_2$, was determined at a flow rate of 10 μl/min. Dissociation rate constants ($k_{off}$) were the average of five measurements obtained by analyzing the dissociation phase at an increased flow rate (40 μl/min). Sensorgrams were analyzed with the BIAevaluation 2.1 program (Pharmacia). Residual Fab was removed after each measurement with 10 mM HCl, 2 mM $CaCl_2$ and 1 mM $MgCl_2$.

Table 9 shows that the variants all displayed a lower Kd than the LM609 grafted antibody parent molecule, consistent with both the capture lift and the ELISA.

Analysis of association and dissociation rates revealed that the majority of improved variants had slower dissociation rates while having similar association rates. For example, LM609 grafted antibody had an association rate $18.0\times10^4$ $M^{-1}s^{-1}$, while the variants ranged from 16.7–$31.8\times10^4$ $M^{-1}s^{-1}$. In contrast, every clone dissociated slower than LM609 grafted antibody ($4.97\times10^{-3}$ $s^{-1}$) with dissociation rates ranging from 1.6-fold ($3.03\times10^{-3}$ $s^{-1}$) to 11.8-fold ($0.42\times10^{-3}$ $s^{-1}$) slower.

These results demonstrate that introducing single amino acid substitutions into LM609 grafted antibody CDRs allows the identification of modified LM609 grafted antibodies having higher affinity for $\alpha_v\beta_3$ than the parent LM609 grafted antibody.

TABLE 9

Identification of Enhanced LM609 Grafted Antibodies from Primary Libraries

| chain | library | sequence | | | | | | | | | $k_{on}$ (×10⁴) ($M^{-1}s^{-1}$) | $k_{off}$ (×10⁻³) ($s^{-1}$) | Kd (nM) |
|---|---|---|---|---|---|---|---|---|---|---|---|---|---|
| | LM609 grafted antibody | | | | | | | | | | 18.0 | 4.97 | 27.6 |
| H | CDR1 | G | F | T | F | S | S | Y | D | M S | | | |
| | T27 | | | T | | | | | | | n.d. | n.d. | n.d. |
| | W29 | | | | | W | | | | | n.d. | n.d. | n.d. |
| | L30 | | | | | | | L | | | n.d. | n.d. | n.d. |
| H | CDR2a | W | V | A | K | V | S | S | G | G G | | | |
| | K52 | | | | K | | | | | | 17.8 | 2.18 | 12.2 |
| H | CDR2b | S | T | Y | Y | L | D | T | V | Q G | | | |
| | P60 | | | | | P | | | | | 31.8 | 1.85 | 5.8 |
| | E64 | | | | | | | | E | | n.d. | n.d. | n.d. |
| H | CDR3 | A | R | H | N | Y | G | S | F | A Y | | | |
| | H97 | | | H | | | | | | | 22.0 | 3.03 | 13.8 |
| | Y100 | | | | | Y | | | | | 17.5 | 2.51 | 14.3 |
| | D101 | | | | | | | D | | | n.d. | n.d. | n.d. |
| | Y101 | | | | | | | Y | | | 21.8 | 0.48 | 2.2 |
| | S102 | | | | | | | | | S | 24.2 | 1.44 | 6.0 |
| | T102 | | | | | | | | | T | 24.6 | 1.43 | 5.8 |
| | D102 | | | | | | | | | D | 27.6 | 0.97 | 3.5 |
| | E102 | | | | | | | | | E | n.d. | n.d. | n.d. |
| | M102 | | | | | | | | | M | n.d. | n.d. | n.d. |
| | G102 | | | | | | | | | G | 16.1 | 2.01 | 12.5 |
| | A102 | | | | | | | | | A | 27.5 | 2.27 | 8.3 |
| L | CDR1 | Q | A | S | Q | S | I | S | N | H L W Y | | | |
| | F32 | | | | | | | F | | | 16.7 | 0.42 | 2.5 |
| L | CDR2 | | | L | L | I | R | Y | R | S Q S I S | | | |
| | S51 | | | | | | | S | | | n.d. | n.d. | n.d. |
| L | CDR3 | | | Q | Q | S | G | S | W | P H T | | | |
| | N92 | | | | | N | | | | | 23.6 | 1.35 | 5.7 |
| | T92 | | | | | T | | | | | n.d. | n.d. | n.d. |
| | L96 | | | | | | | | | L | 24.3 | 2.23 | 9.2 |
| | Q96 | | | | | | | | | Q | n.d. | n.d. | n.d. |

EXAMPLE VII

Generation of High Affinity LM609 Grafted Antibodies

This example shows that single amino acid mutations in CDRs of an LM609 grafted that result in higher affinity binding to $\alpha_v\beta_3$ can be combined to generate high affinity LM609 grafted antibodies.

Random combination of all of the beneficial mutations of LM609 grafted antibody would generate a combinatorial library containing >$10^5$ variants, requiring efficient screening methodologies. Therefore, to determine if clones displaying >10-fold enhanced affinities could be rapidly distinguished from one another, variants displaying 3 to 13-fold enhanced affinity were evaluated by capture lift utilizing lower concentrations of biotinylated $\alpha_v\beta_3$. Despite repeated attempts with a broad range of concentrations of $\alpha_v\beta_3$, consistent differences in the capture lift signals were not observed. Because of this, smaller combinatorial libraries were constructed and subsequently screened by ELISA.

Figure 9:
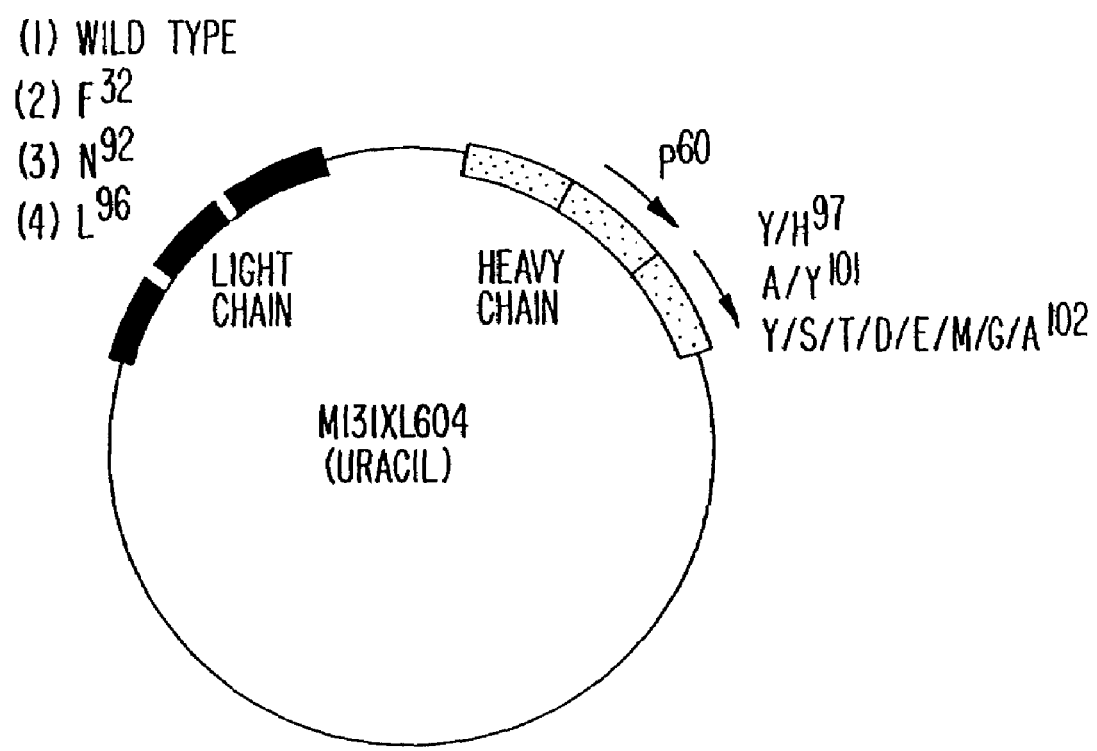
FIG. 9 shows the construction of combinatorial libraries of enhanced LM609 grafted antibody variants containing multiple amino acid substitutions.

Four distinct combinatorial libraries were constructed in order to evaluate the optimal number of combinations that could be accomplished utilizing two site hybridization mutagenesis (FIG. 9). Briefly, combinatorial libraries were constructed by synthesizing degenerate oligonucleotides encoding both the wild-type and beneficial heavy chain mutations (H2, Leu$^{60}$-Pro; H3 Tyr$^{97}$-His; H3, Ala$^{101}$-Tyr; H3, Tyr$^{102}$-Ser, Thr, Asp, Glu, Met, Gly, Ala). Utilizing two site hybridization mutagenesis, as described above, the oligonucleotides were annealed at a 40:1 molar ratio to uridinylated template prepared from LM609 grafted antibody and three light chain mutations (FIG. 9; L1, His$^{32}$-Phe; L3, Gly$^{92}$-Asn; L3, His$^{96}$-Leu). As a result, a total of 256 variants were synthesized in four combinatorial library subsets.

FIG. 9 shows construction of combinatorial libraries of beneficial mutations. Uridinylated template from LM609 grafted antibody and three optimal light chain variants (F32, N92, and L96) was prepared. Two site hybridization was performed with two degenerate oligonucleotides, which were designed to introduce beneficial mutations at four distinct heavy chain residues.

Following preparation of uridinylated templates of LM609 grafted antibody and three light chain variants, (Table 9; F32, N92, and L96), degenerate oligonucleotides encoding the wild type residue and the most beneficial heavy chain mutations (Table 9; P60, H97, Y101, S102, T102, D102, E102, M102, G102, and A102) were hybridized to the light chain templates, resulting in four combinatorial libraries, each containing 64 unique variants. Potentially, the combination of multiple mutations can have detrimental effects on affinity and, thus, can prevent the identification of beneficial combinations resulting from mutations at fewer sites. For this reason, the amino acid expressed by the LM609 grafted antibody parent molecule was included at each position in the combinatorial library. By utilizing this approach, simultaneous combinatorial mutagenesis of three CDRs (L1 or L3 each in combination with H2 and H3) was accomplished. Based on sequence analysis, the two site hybridization mutagenesis was achieved with ~50% efficiency.

In order to screen the combinatorial libraries, soluble Fab was expressed and released from the periplasm of small-scale (<1 ml) bacterial cultures that had been infected with randomly selected clones. Although variable expression levels were observed, uniform quantities of the unpurified variants were captured on a microtiter plate through a peptide tag present on the carboxyl-terminus of the heavy chain. Briefly, combinatorial LM609 grafted antibody libraries were screened by an EL1SA that permits the determination of relative affinities of antibody variants produced in small-scale bacterial cultures (Watkins et al., *Anal. Biochem.* 253:37-45 (1997)). An Immulon II microtiter plate (Dynatech Laboratories; Chantilly, Va.) was coated with 10 µg/ml of the 7F11 monoclonal antibody, which recognizes a peptide tag on the carboxyl-terminus of the LM609 grafted antibody variant heavy chains (Field et al., *Mol. Cell. Biol.* 8:2159-2165 (1988)). Following capture of Fab from *E. coli* lysates, the plate was incubated with 0.5-1 µg/ml biotinylated $\alpha_v\beta_3$ for 1 h at 25° C. The plate was washed seven times, incubated with 0.5 U/ml streptavidin-alkaline phosphatase (1000 U/ml; Boehringer Mannheim; Indianapolis, Ind.) for 15 min at 25° C., washed seven times, and developed as described previously (Watkins et al., supra, 1997). All dilutions and washes were in binding buffer.

As described previously (Watkins et al., supra, 1997), this ELISA screening method enabled a rapid and direct comparison of the relative affinities of the variants following incubation with biotinylated $\alpha_v\beta_3$ and streptavidin-alkaline phosphatase. To ensure that the full Fab diversity was sampled, one thousand randomly selected clones were screened from each combinatorial library. Variants that displayed an enhanced EL1SA signal were further characterized for binding to immobilized $\alpha_v\beta_3$ (FIG. 8, closed triangles) and were sequenced to identify the mutations (Table 10).

Screening of the four combinatorial libraries identified fourteen unique combinations of mutations that improved binding significantly over the individual mutations identified in the screening of the first library. While the best clone from the primary screen had a 12.5-fold increase in affinity, the fourteen unique combinations isolated from screening the combinatorial libraries displayed affinities ranging from 18 to 92-fold greater than the parent LM609 grafted antibody. The majority of these variants consisted of H2 and H3 mutations combined with the L1 or L3 mutations. Beneficial combinations of heavy chain mutations with wild-type light chain were also identified, but did not result in improved affinity to the same extent as other combinatorial variants. The variants predominantly contained 2 to 4 mutations, with one clone, C29, containing five mutations. No direct correlation between the total number of mutations in each variant and the resulting affinity was observed. For example, while the binding of clone C37 was 92-fold enhanced over the parent molecule and was achieved through the combination of three mutations, clone C29 had ~55-fold greater affinity achieved through the combination of five mutations. Multiple variants displaying >50-fold enhanced affinity resulting from the combination of as few as two mutations were identified (2G4, 17, and V357D).

The combinatorial clones with improved affinity all displayed >10-fold slower dissociation rates, possibly reflecting a selection bias introduced by long incubation steps in the screening. In addition, all of the combinatorial variants isolated from the library based on the L96 light chain mutation also displayed 2 to 4-fold greater association rates. Previously, it has been demonstrated that the antibody repertoire shifts towards immunoglobulins displaying higher association rates during affinity maturation in vivo (Foote and Milstein, Nature 352:530-532 (1991)). The L96 subset of variants, therefore, may more closely mimic the in vivo affinity maturation process where B-lymphocyte proliferation is subject to a kinetic selection.

LM609 grafted antibody binds the $\alpha_v\beta_3$ complex specifically and does not recognize either the $\alpha_v$ or the 3 chain separately. To further characterize the variants, clones were screened for reactivity with the related integrins, $\alpha_{11b}\beta_3$ and $\alpha_v\beta_5$. All variants tested were unreactive with both $\alpha_{11b}\beta_3$ and $\alpha_v\beta_5$, consistent with the improved binding not substantially altering the interaction of Fab and receptor.

As a first step toward determining if the increase in affinity of the variants resulted in greater biological activity, variants displaying a range of affinities were assayed for their ability to inhibit the binding of a natural ligand, fibrinogen, to immobilized $\alpha_v\beta_3$ receptor. Briefly, LM609 grafted antibody variants were tested for inhibition of ligand binding as described previously except that the binding of biotinylated human fibrinogen (Calbiochem, La Jolla, Calif.) was detected with 0.5 µg/ml NeutrAvidin-alkaline phosphatase (Smith et al., *J. Biol. Chem.* 265:12267-12271 (1990)).

TABLE 10

Identification of Optimal Combinatorial Mutations

| library* | clone | L1 32 | L3 92 | L3 96 | H2 60 | H3 97 | H3 101 | H3 102 | $k_{on}$ (×10$^4$) (M$^{-1}$s$^{-1}$) | $k_{off}$ (×10$^{-3}$) (s$^{-1}$) | Kd (nM) |
|---|---|---|---|---|---|---|---|---|---|---|---|
| wild type |  | H | G | H | L | Y | A | Y | 18.0 | 4.97 | 27.6 |
| F32 | 17 | F |  |  |  |  |  | S | 25.1 | 0.138 | 0.5 |
|  | 7 | F |  |  | P | H |  | S | 20.4 | 0.236 | 1.2 |
|  | 56 | F |  |  | P |  |  | S | 26.6 | 0.135 | 0.5 |
|  | C59 | F |  |  | P |  |  | D | 26.5 | 0.137 | 0.5 |
|  | C176 | F |  |  | P |  |  | T | 22.5 | 0.192 | 0.9 |
|  | V357D | F |  |  |  |  |  | D | 27.9 | 0.140 | 0.5 |
| N92 | C119 |  | N |  | P |  |  | S | 21.5 | 0.316 | 1.5 |
| L96 | 8F9 |  |  | L | P | H |  | S | 47.5 | 0.280 | 0.6 |
|  | C29 |  |  | L | P | H | Y | S | 67.5 | 0.343 | 0.5 |
|  | 2G4 |  |  | L |  |  |  | S | 60.3 | 0.229 | 0.4 |
|  | 6H6 |  |  | L |  | H |  | S | 50.4 | 0.187 | 0.4 |
|  | C37 |  |  | L |  |  | Y | E | 44.8 | 0.147 | 0.3 |
|  | 6D1 |  |  | L | P |  | Y | S | 41.0 | 0.158 | 0.4 |
|  | 6G1 |  |  | L | P |  |  | S | 38.9 | 0.280 | 0.7 |

Figure 10A:
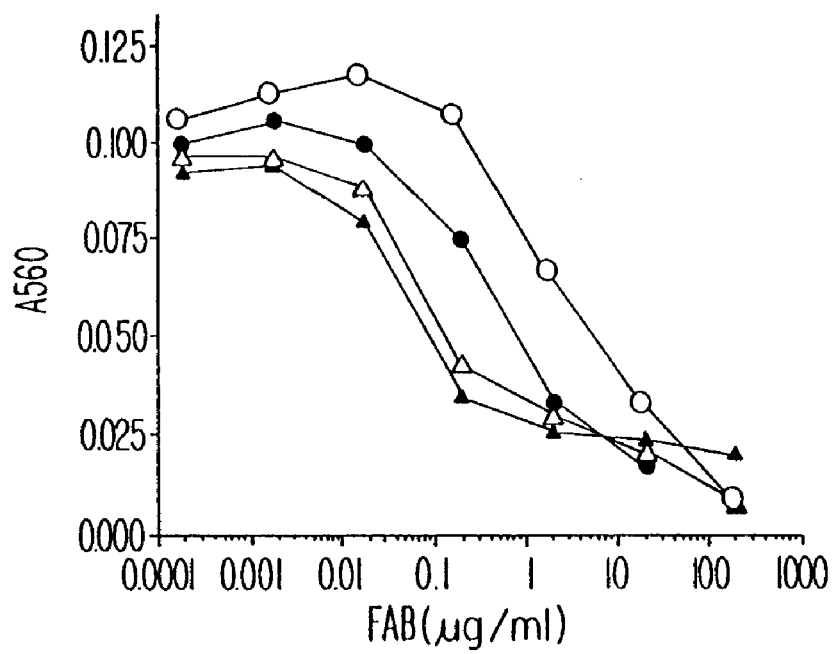
FIG. 10A shows inhibition of fibrinogen binding to immobilized $\alpha_v\beta_3$.
Figure 10B:
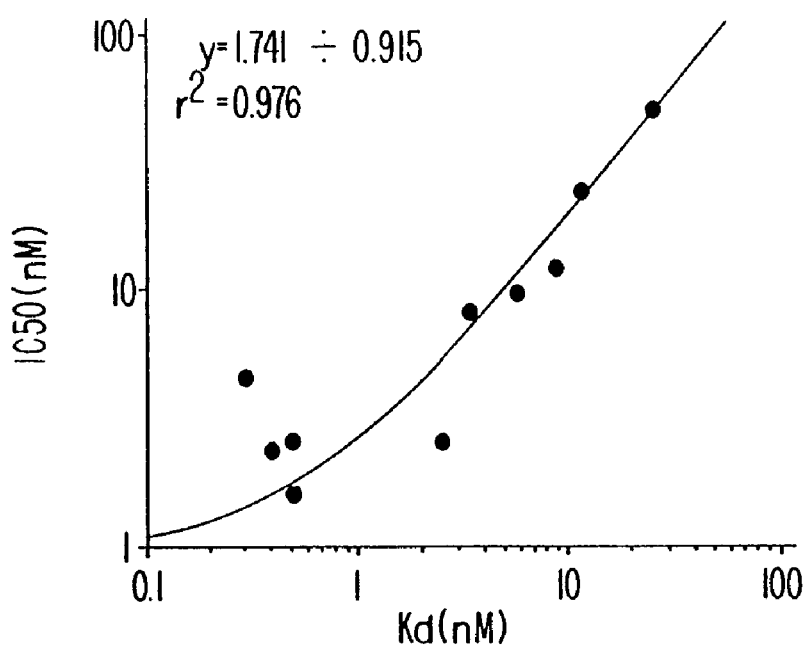
FIG. 10B shows correlation of affinity of antibody variants with inhibition of fibrinogen binding.

The results of these competition assays are shown in FIG. 10. FIG. 10A shows inhibition of fibrinogen binding to immobilized $\alpha_v\beta_3$. Immobilized $\alpha_v\beta_3$ was incubated with 0.1 μg/ml biotinylated fibrinogen and various concentrations of LM609 grafted antibody (open circles), S102 (closed circles), F32 (open triangles), or C59 (closed triangles) for 3 h at 37° C. Unbound ligand and Fab were removed by washing and bound fibrinogen was quantitated following incubation with NeutrAvidin alkaline phosphatase conjugate. FIG. 10B shows correlation of affinity of variants with inhibition of fibrinogen binding. The concentration of variants required to inhibit the binding of fibrinogen to immobilized $\alpha_v\beta_3$ by 50% (IC$_{50}$) was plotted as a function of the affinity (Kd).

As shown in FIG. 10A, higher affinity variants were more effective at blocking the ligand binding site of the receptor (compare LM609 grafted antibody, open circles, with any of the variants). Subsequent analysis of ten variants displaying affinities (Kd) ranging from 0.3 to 27 nm demonstrated a good correlation ($r^2$=0.976) between affinity and ability to inhibit fibrinogen binding (FIG. 10B). In addition, the variants were tested for inhibition of vitronectin binding to the receptor. Similar to fibrinogen, the variants were more effective at inhibiting the interaction than the parent molecule. Thus, consistent with the cross-reactivity studies with related integrin receptors, mutations which increased affinity did not appear to substantially alter the manner in which the antibody interacted with the receptor.

Figure 11:
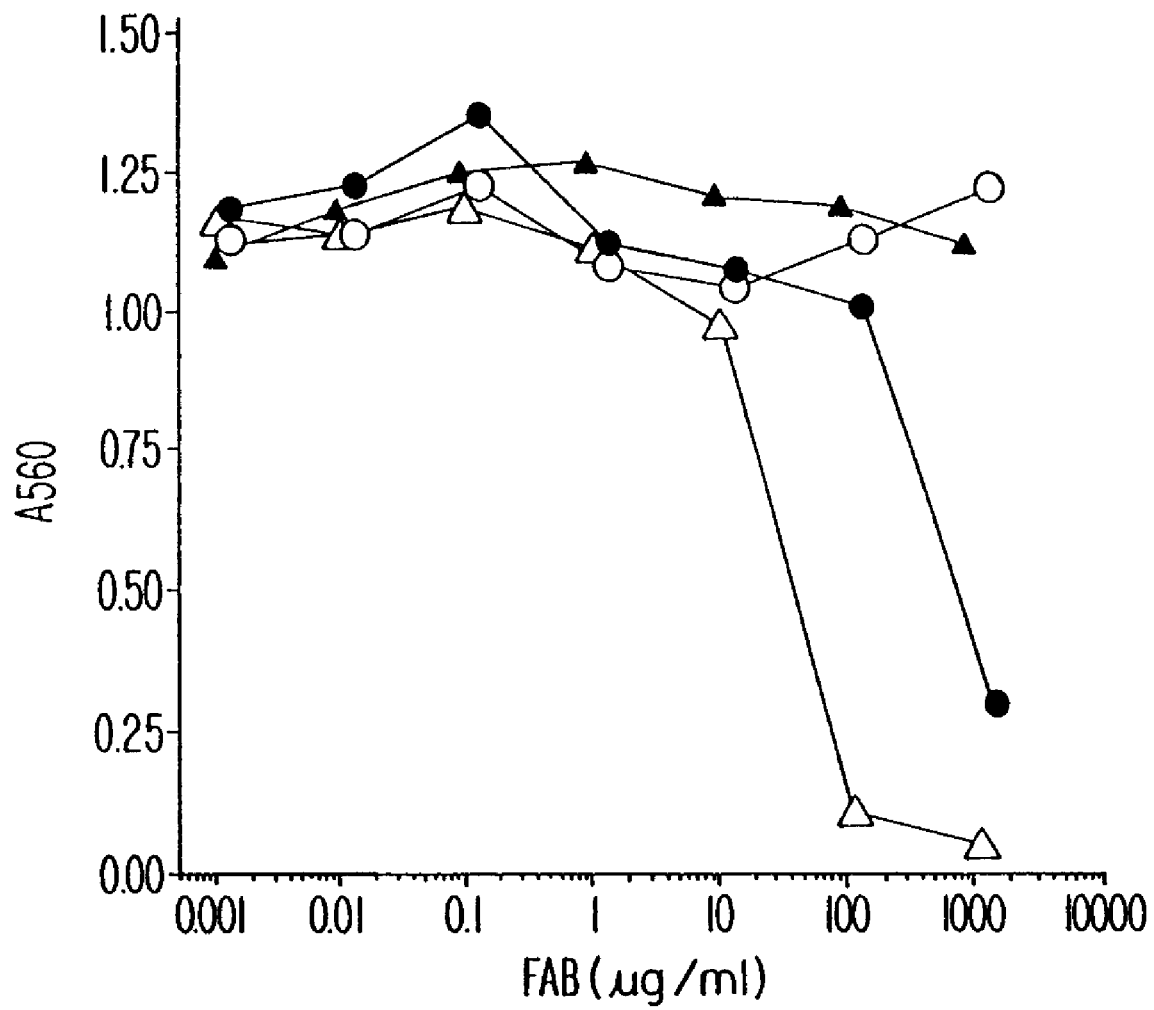
FIG. 11 shows the inhibition of M21 human melanoma cell adhesion to fibrinogen by LM609 grafted antibody variants. Cell binding to 10 µg/ml fibrinogen-coated substrate was assessed in the presence of various concentrations of LM609 grafted Fab (closed triangles) or the enhanced LM609 grafted Fabs S102 (open circles), G102 (closed circles), or C37 (open triangles).

The ability of the variants to inhibit the adhesion of M21 human melanoma cells expressing the $\alpha_v\beta_3$ receptor to fibrinogen was examined. Inhibition of the adhesion of 4×10$^4$ M21 cells to fibrinogen by the LM609 grafted antibody variants was performed as described previously (Leavesley et al., J. Cell Biol. 117:1101-1107 (1992)). Similar to the ligand competition studies with purified fibrinogen and $\alpha_v\beta_3$ receptor, higher affinity variants were generally more effective at preventing cell adhesion than was LM609 grafted antibody (FIG. 11). FIG. 11 shows inhibition of M21 human melanoma cell adhesion to fibrinogen. Cells and various concentrations of LM609 grafted antibody Fab (closed triangles), S102 (open circles), G102 (closed circles), or C37 (open triangles) were added to 96 well cell culture plates which had been coated with 10 μg/ml fibrinogen. After incubating for 35 min at 37° C., unbound cells were removed by washing and adherent cells were quantitated by crystal violet staining.

Although intact LM609 grafted antibody Ig inhibits cell adhesion, the phage expressed Fab did not affect cell adhesion at concentrations as high as 1 mg/ml (FIG. 11, closed triangles). Clone C37, isolated from the combinatorial library and displaying ~90-fold greater affinity than LM609 grafted antibody Fab, inhibited cell adhesion completely (FIG. 11, open triangles). Variant G102 had a moderately higher affinity (2.2-fold enhanced) and also inhibited cell adhesion, though less effectively than C37 (FIG. 11, closed circles). Surprisingly, clone S102 (FIG. 11, open circles), which had a 4.6-fold higher affinity than LM609 grafted antibody, was ineffective at inhibiting cell adhesion, suggesting that clones G102 and S102 interact with the $\alpha_v\beta_3$ receptor differently.

These results show that combining single amino acid mutations that result in LM609 grafted antibodies exhibiting higher binding affinity to $\alpha_v\beta_3$ allows the identification of high affinity LM609 grafted antibody mutants having greater than 90-fold higher binding affinity than the parent LM609 grafted antibody.

EXAMPLE VIII

Generation of High Affinity Enhanced LM609 Grafted Antibodies

This example describes the generation of high affinity enhanced LM609 grafted antibodies having increased stability.

The high affinity clone 6H6 (see Table 10 in Example VII) was further characterized and was found to exhibit some proteolysis. Therefore, to identify variants having increased stability, 32 codon variants were introduced simultaneously at each of positions Asn$^{96}$ and His$^{97}$ (numbering according to Kabat et al., supra) in the heavy chain CDR3 of 6H6 (SEQ ID NO:94), and the variants were screened for $\alpha_v\beta_3$ binding activity. Those variants that retained binding activity were sequenced and then screened for susceptibility to proteolysis. The variant 6H6LH was identified as exhibiting $\alpha_v\beta_3$ binding activity and resistance to proteolysis (see Tables 11 and 15). The 6H6LH variant, which had high affinity $\alpha_v\beta_3$ binding activity, had Leu substituted for Asn$^{96}$ but retained His$^{97}$.

Although the 6H6LH variant exhibited high affinity binding to $\alpha_v\beta_3$, the affinity was somewhat lower than the 6H6 variant (see Table 15). Therefore, CDR mutations that had been found to give high affinity binding were combined with the 6H6LH variant. Specifically, His$^{32}$ in the light chain CDR1 of 6H6 was mutated to Phe, as in clone F32 (see Table 9), to generate clone 2236/6H6LH (see Table 13). In an additional variant, Leu$^{61}$ in the heavy chain CDR2 of 6H6 was also mutated to Pro, as in clone P60 (see Table 9), to generate clone 2236-38/6H6LH (see Table 11).

Shown in Tables 11 and 12 are amino acid and nucleotide sequences, respectively, of heavy chain CDRs of the enhanced high affinity variants of 6H6. Shown in Tables 13 and 14 are amino acid and nucleotide sequences, respectively, of light chain CDRs of the enhanced high affinity variants of 6H6. The CDRs shown are according to Chothia, supra. The amino acids and codons that differ from the 6H6 variant are shown in bold.

TABLE 11

Amino Acid Sequences of Heavy Chain CDRs of High Affinity Enhanced 6H6 Variant Antibodies

```
Heavy Chain CDR1
Clone
6H6LH          G F T F S S Y D M S        SEQ ID NO:34
2236/6H6LH     G F T F S S Y D M S        SEQ ID NO:24
2236-38/6H6LH  G F T F S S Y D M S        SEQ ID NO:34

Heavy Chain CDR2
Clone
6H6LH          K V S S G G G S T Y        SEQ ID NO:102
               Y L D T V Q G
2236/6H6LH     K V S S G G G S T Y        SEQ ID NO:102
               Y L D T V Q G
2236-38/6H6LH  K V S S G G G S T Y        SEQ ID NO:104
               Y P D T V Q G Heavy Chain CDR3
6H6LH          H L H G S F A S            SEQ ID NO:106
2236/6H6LH     H L H C S F A S            SEQ ID NO:106
2236-38/6H6LH  H L H G S F A S            SEQ ID NO:106
```

TABLE 12

Nucleotide Sequences of Heavy Chain CDRs of High Affinity Enhanced 6H6 Variant Antibodies

```
Heavy Chain CDR1
                                          SEQ ID NO:33
6H6LH          GGA TTC ACC TTC AGT AGC TAT GAC
               ATG TCT
                                          SEQ ID NO:33
2236/6H6LH     GGA TTC ACC TTC AGT AGC TAT GAC
               ATG TCT
                                          SEQ ID NO:33
2236-38/6H6    GGA TTC ACC TTC AGT AGC TAT GAC
               ATG TCT Heavy Chain CDR2
                                          SEQ ID NO:101
6H6LH          AAA GTT AGT AGT GGT GGT GGT AGC
               ACC TAC TAT TTA GAC ACT GTG CAG
               GGC
                                          SEQ ID NO:101
2236/6H6LH     AAA GTT AGT AGT GGT GGT GGT AGC
               ACC TAC TAT TTA GAC ACT GTG CAG
               GGC
                                          SEQ ID NO:103
2236-38/6H6LH  AAA GTT AGT AGT GGT GGT GGT AGC
               ACC TAC TAT CCA GAC ACT GTG CAG
               GGC Heavy Chain CDR3
                                          SEQ ID NO:105
6H6LH          CAT CTT CAT GGC AGT TTT GCT TCT
                                          SEQ ID NO:105
2236/6H6LH     CAT CTT CAT GGC AGT TTT GCT TCT
                                          SEQ ID NO:105
2236-38/6H6LH  CAT CTT CAT GGC AGT TTT GCT TCT
```

TABLE 13

Amino Acid Sequences of Light Chain CDRs of High Affinity Enhanced 6H6 Variant Antibodies

```
Light Chain CDR1
6H6LH          Q A S Q S I S N H L H      SEQ ID NO:108
2236/6H6LH     Q A S Q S I S N F L H      SEQ ID NO:110
2236-38/6H6LH  Q A S Q S I S N F L H      SEQ ID NO:110

Light Chain CDR2
6H6LH          Y R S Q S I S              SEQ ID NO:112
2236/6H6LH     Y R S Q S I S              SEQ ID NO:112
2236-38/6H6LH  Y R S Q S I S              SEQ ID NO:112

Light Chain CDR3
6H6LH          Q Q S G S W P L T          SEQ ID NO:90
2236/6H6LH     Q Q S G S W P L T          SEQ ID NO:90
2236-38/6H6LH  Q Q S G S W P L T          SEQ ID NO:90
```

TABLE 14

Nucleotide Sequences of Light Chain CDRs of High Affinity Enhanced 6H6 Variant Antibodies

```
Light Chain CDR1
                                          SEQ ID NO:107
6H6LH          CAG GCC AGC CAA AGT ATT AGC AAC
               CAC CTA CAC
                                          SEQ ID NO:109
2236/6H6LH     CAG GCC AGC CAA AGT ATT AGC AAC
               TTC CTA CAC
                                          SEQ ID NO:109
2236-38/6H6LH  CAG GCC AGC CAA AGT ATT AGC AAC
               TTC CTA CAC Light Chain CDR2
                                          SEQ ID NO:111
6H6LH          TAT CGT TCC CAG TCC ATC TCT
                                          SEQ ID NO:111
2236/6H6LH     TAT CGT TCC CAG TCC ATC TCT
                                          SEQ ID NO:111
2226-38/6H6LH  TAT CGT TCC CAG TCC ATC TCT Light Chain CDR3
                                          SEQ ID NO:89
6H6LH          CAA CAG AGT GGC AGC TGG CCT CTG
               ACG
                                          SEQ ID NO:89
2236/6H6LH     CAA CAG AGT GGC AGC TGG CCT CTG
               ACG
                                          SEQ ID NO:89
2236-38/6H6LH  CAA CAG AGT GGC AGC TGG CCT CTG
               ACG
```

The kinetics of $\alpha_v\beta_3$ binding was determined for each clone using surface plasmon resonance (BIACORE) essentially as described in Example VI. The binding kinetics and affinities of the clones are shown in Table 15.

TABLE 15

Binding Kinetics of Enhanced LM609 Grafted Antibody Clones

| Clone ID# | $k_{on}$ | $k_{off}$ | $K_d$ |
|---|---|---|---|
| 6H6 | 2.59E+05 | 1.60E−04 | 0.62 nM |
| 2236/6H6LH | 2.25E+05 | 1.48E−04 | 0.66 nM |
| 6H6LH | 3.01E+05 | 5.48E−04 | 1.82 nM |
| 2236-38/6H6LH | 2.76E+05 | 2.49E−04 | 0.90 nM |

As shown in Table 15, clones 6H6LH, 2236/6H6LH, and 2236-38/6H6LH had affinities similar to 6H6. The affinity for 6H6 in these experiments was 0.62 nM, compared to 0.4 nM observed in the previous experiment (see Table 10 in Example VII). This difference is due to the observed $k_{on}$, which is within the variability of the experiments. The on rates were very similar between 6H6, 6H6LH, 2236/6H6LH, and 2236-38/6H6LH. The small difference in the observed Kd appeared to be due primarily to differences in $k_{off}$.

These results describe additional enhanced LM609 grafted antibodies exhibiting high affinity for $\alpha_v\beta_3$ and resistance to proteolysis.

Throughout this application various publications have been referenced. The disclosures of these publications in their entireties are hereby incorporated by reference in this application in order to more fully describe the state of the art to which this invention pertains.

Although the invention has been described with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

---

What is claimed is:

1. A grafted antibody exhibiting selective binding affinity to $\alpha_v\beta_3$, or a functional antigen-binding fragment thereof, said functional antigen-binding fragment selected from the group consisting of Fv, Fab, F(ab)$_2$ and scFV, said antibody or functional antigen-binding fragment thereof comprising a $V_H$ CDR1 referenced as SEQ ID NO:34; a $V_H$ CDR2 referenced as SEQ ID NO: 102; a $V_H$ CDR3 referenced as SEQ ID NO: 106; and a $V_L$ CDR1 referenced as SEQ ID NO: 110, a $V_L$ CDR2 referenced as SEQ ID NO: 112; and a $V_L$ CDR3 referenced as SEQ ID NO:90.

2. The functional antigen-binding fragment of claim 1, wherein said fragment is Fv.

3. The functional antigen-binding fragment of claim 1, wherein said fragment is Fab.

4. The functional antigen-binding fragment of claim 1, wherein said fragment is F(ab)$_2$.

5. The functional antigen-binding fragment of claim 1, wherein said fragment is scFV.

* * * * *

SEQUENCE LISTING

```
<160> NUMBER OF SEQ ID NOS: 112

<210> SEQ ID NO 1
<211> LENGTH: 351
<212> TYPE: DNA
<213> ORGANISM: Artificial Sequence
<220> FEATURE:
<221> NAME/KEY: CDS
<222> LOCATION: (1)..(351)
<223> OTHER INFORMATION: Description of Artificial Sequence: grafted
      antibody variable region

<400> SEQUENCE: 1 cag gtg cag ctg gtg gag tct ggg gga ggc gtt gtg cag cct gga agg      48
Gln Val Gln Leu Val Glu Ser Gly Gly Gly Val Val Gln Pro Gly Arg
 1               5                  10                  15 tcc ctg aga ctc tcc tgt gca gcc tct gga ttc acc ttc agt agc tat      96
Ser Leu Arg Leu Ser Cys Ala Ala Ser Gly Phe Thr Phe Ser Ser Tyr
             20                  25                  30 gac atg tct tgg gtt cgc cag gct ccg ggc aag ggt ctg gag tgg gtc     144
Asp Met Ser Trp Val Arg Gln Ala Pro Gly Lys Gly Leu Glu Trp Val
         35                  40                  45 gca aaa gtt agt agt ggt ggt ggt agc acc tac tat tta gac act gtg     192
Ala Lys Val Ser Ser Gly Gly Gly Ser Thr Tyr Tyr Leu Asp Thr Val
     50                  55                  60 cag ggc cga ttc acc atc tcc aga gac aat agt aag aac acc cta tac     240
Gln Gly Arg Phe Thr Ile Ser Arg Asp Asn Ser Lys Asn Thr Leu Tyr
 65                  70                  75                  80 ctg caa atg aac tct ctg aga gcc gag gac aca gcc gtg tat tac tgt     288
Leu Gln Met Asn Ser Leu Arg Ala Glu Asp Thr Ala Val Tyr Tyr Cys
                 85                  90                  95 gca aga cat aac tac ggc agt ttt gct tac tgg ggc caa ggg act aca     336
Ala Arg His Asn Tyr Gly Ser Phe Ala Tyr Trp Gly Gln Gly Thr Thr
            100                 105                 110 gtg act gtt tct agt                                                  351
Val Thr Val Ser Ser
        115

<210> SEQ ID NO 2
<211> LENGTH: 117
<212> TYPE: PRT
<213> ORGANISM: Artificial Sequence
<220> FEATURE:
<223> OTHER INFORMATION: Description of Artificial Sequence: grafted
      antibody variable region

<400> SEQUENCE: 2

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
             20                  25                  30
```

```
Asp Met Ser Trp Val Arg Gln Ala Pro Gly Lys Gly Leu Glu Trp Val
        35                  40                  45

Ala Lys Val Ser Ser Gly Gly Ser Thr Tyr Tyr Leu Asp Thr Val
    50                  55                  60

Gln Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg His Asn Tyr Gly Ser Phe Ala Tyr Trp Gly Gln Gly Thr Thr
            100                 105                 110

Val Thr Val Ser Ser
        115

<210> SEQ ID NO 3
<211> LENGTH: 321
<212> TYPE: DNA
<213> ORGANISM: Artificial Sequence
<220> FEATURE:
<221> NAME/KEY: CDS
<222> LOCATION: (1)..(321)
<223> OTHER INFORMATION: Description of Artificial Sequence: grafted
      antibody variable region

<400> SEQUENCE: 3 gag att gtg cta act cag tct cca gcc acc ctg tct ctc agc cca gga        48
Glu Ile Val Leu Thr Gln Ser Pro Ala Thr Leu Ser Leu Ser Pro Gly
 1               5                  10                  15 gaa agg gcg act ctt tcc tgc cag gcc agc caa agt att agc aac cac        96
Glu Arg Ala Thr Leu Ser Cys Gln Ala Ser Gln Ser Ile Ser Asn His
                20                  25                  30 cta cac tgg tat caa caa agg cct ggt caa gcc cca agg ctt ctc atc       144
Leu His Trp Tyr Gln Gln Arg Pro Gly Gln Ala Pro Arg Leu Leu Ile
            35                  40                  45 aag tat cgt tcc cag tcc atc tct ggg atc ccc gcc agg ttc agt ggc       192
Lys Tyr Arg Ser Gln Ser Ile Ser Gly Ile Pro Ala Arg Phe Ser Gly
    50                  55                  60 agt gga tca ggg aca gat ttc acc ctc act atc tcc agt ctg gag cct       240
Ser Gly Ser Gly Thr Asp Phe Thr Leu Thr Ile Ser Ser Leu Glu Pro
 65                  70                  75                  80 gaa gat ttt gca gtc tat tac tgt caa cag agt ggc agc tgg cct cac       288
Glu Asp Phe Ala Val Tyr Tyr Cys Gln Gln Ser Gly Ser Trp Pro His
                85                  90                  95 acg ttc gga ggg ggg acc aag gtg gaa att aag                           321
Thr Phe Gly Gly Gly Thr Lys Val Glu Ile Lys
            100                 105

<210> SEQ ID NO 4
<211> LENGTH: 107
<212> TYPE: PRT
<213> ORGANISM: Artificial Sequence
<220> FEATURE:
<223> OTHER INFORMATION: Description of Artificial Sequence: grafted
      antibody variable region

<400> SEQUENCE: 4

Glu Ile Val Leu Thr Gln Ser Pro Ala Thr Leu Ser Leu Ser Pro Gly
 1               5                  10                  15

Glu Arg Ala Thr Leu Ser Cys Gln Ala Ser Gln Ser Ile Ser Asn His
                20                  25                  30

Leu His Trp Tyr Gln Gln Arg Pro Gly Gln Ala Pro Arg Leu Leu Ile
            35                  40                  45
```

```
Lys Tyr Arg Ser Gln Ser Ile Ser Gly Ile Pro Ala Arg Phe Ser Gly
        50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Ser Gly Ser Trp Pro His
                 85                  90                  95

Thr Phe Gly Gly Gly Thr Lys Val Glu Ile Lys
            100                 105
```

<210> SEQ ID NO 5
<211> LENGTH: 351
<212> TYPE: DNA
<213> ORGANISM: Mus musculus
<220> FEATURE:
<221> NAME/KEY: CDS
<222> LOCATION: (1)..(351)

<400> SEQUENCE: 5

```
gaa gtg cag ctg gtg gag tct ggg gga ggc tta gtg aag cct gga agg       48
Glu Val Gln Leu Val Glu Ser Gly Gly Gly Leu Val Lys Pro Gly Arg
 1               5                  10                  15 tcc ctg aga ctc tcc tgt gca gcc tct gga ttc gct ttc agt agc tat       96
Ser Leu Arg Leu Ser Cys Ala Ala Ser Gly Phe Ala Phe Ser Ser Tyr
                 20                  25                  30 gac atg tct tgg gtt cgc cag att ccg gag aag agg ctg gag tgg gtc      144
Asp Met Ser Trp Val Arg Gln Ile Pro Glu Lys Arg Leu Glu Trp Val
             35                  40                  45 gca aaa gtt agt agt ggt ggt ggt agc acc tac tat tta gac act gtg      192
Ala Lys Val Ser Ser Gly Gly Gly Ser Thr Tyr Tyr Leu Asp Thr Val
         50                  55                  60 cag ggc cga ttc acc atc tcc aga gac aat gcc aag aac acc cta tac      240
Gln Gly Arg Phe Thr Ile Ser Arg Asp Asn Ala Lys Asn Thr Leu Tyr
 65                  70                  75                  80 ctg caa atg agc agt ctg aac tct gag gac aca gcc atg tat tac tgt      288
Leu Gln Met Ser Ser Leu Asn Ser Glu Asp Thr Ala Met Tyr Tyr Cys
                 85                  90                  95 gca aga cat aac tac ggc agt ttt gct tac tgg ggc caa ggg act ctg      336
Ala Arg His Asn Tyr Gly Ser Phe Ala Tyr Trp Gly Gln Gly Thr Leu
            100                 105                 110 gtc act gtc tct gca                                                  351
Val Thr Val Ser Ala
        115
```

<210> SEQ ID NO 6
<211> LENGTH: 117
<212> TYPE: PRT
<213> ORGANISM: Mus musculus

<400> SEQUENCE: 6

```
Glu Val Gln Leu Val Glu Ser Gly Gly Gly Leu Val Lys Pro Gly Arg
 1               5                  10                  15

Ser Leu Arg Leu Ser Cys Ala Ala Ser Gly Phe Ala Phe Ser Ser Tyr
                 20                  25                  30

Asp Met Ser Trp Val Arg Gln Ile Pro Glu Lys Arg Leu Glu Trp Val
             35                  40                  45

Ala Lys Val Ser Ser Gly Gly Gly Ser Thr Tyr Tyr Leu Asp Thr Val
         50                  55                  60

Gln Gly Arg Phe Thr Ile Ser Arg Asp Asn Ala Lys Asn Thr Leu Tyr
 65                  70                  75                  80
```

-continued

```
Leu Gln Met Ser Ser Leu Asn Ser Glu Asp Thr Ala Met Tyr Tyr Cys
                85                  90                  95

Ala Arg His Asn Tyr Gly Ser Phe Ala Tyr Trp Gly Gln Gly Thr Leu
            100                 105                 110

Val Thr Val Ser Ala
        115

<210> SEQ ID NO 7
<211> LENGTH: 321
<212> TYPE: DNA
<213> ORGANISM: Mus musculus
<220> FEATURE:
<221> NAME/KEY: CDS
<222> LOCATION: (1)..(321)

<400> SEQUENCE: 7 gat att gtg cta act cag tct cca gcc acc ctg tct gtg aca cca gga      48
Asp Ile Val Leu Thr Gln Ser Pro Ala Thr Leu Ser Val Thr Pro Gly
 1               5                  10                  15 gat agc gtc agt ctt tcc tgc cag gcc agc caa agt att agc aac cac      96
Asp Ser Val Ser Leu Ser Cys Gln Ala Ser Gln Ser Ile Ser Asn His
            20                  25                  30 cta cac tgg tat caa caa aaa tca cat gag tct cca agg ctt ctc atc     144
Leu His Trp Tyr Gln Gln Lys Ser His Glu Ser Pro Arg Leu Leu Ile
        35                  40                  45 aag tat cgt tcc cag tcc atc tct ggg atc ccc tcc agg ttc agt ggc     192
Lys Tyr Arg Ser Gln Ser Ile Ser Gly Ile Pro Ser Arg Phe Ser Gly
    50                  55                  60 agt gga tca ggg aca gat ttc gct ctc agt atc aac agt gtg gag act     240
Ser Gly Ser Gly Thr Asp Phe Ala Leu Ser Ile Asn Ser Val Glu Thr
65                  70                  75                  80 gaa gat ttt gga atg tat ttc tgt caa cag agt ggc agc tgg cct cac     288
Glu Asp Phe Gly Met Tyr Phe Cys Gln Gln Ser Gly Ser Trp Pro His
                85                  90                  95 acg ttc gga ggg ggg acc aag ctg gaa att aag                         321
Thr Phe Gly Gly Gly Thr Lys Leu Glu Ile Lys
            100                 105

<210> SEQ ID NO 8
<211> LENGTH: 107
<212> TYPE: PRT
<213> ORGANISM: Mus musculus

<400> SEQUENCE: 8

Asp Ile Val Leu Thr Gln Ser Pro Ala Thr Leu Ser Val Thr Pro Gly
 1               5                  10                  15

Asp Ser Val Ser Leu Ser Cys Gln Ala Ser Gln Ser Ile Ser Asn His
            20                  25                  30

Leu His Trp Tyr Gln Gln Lys Ser His Glu Ser Pro Arg Leu Leu Ile
        35                  40                  45

Lys Tyr Arg Ser Gln Ser Ile Ser Gly Ile Pro Ser Arg Phe Ser Gly
    50                  55                  60

Ser Gly Ser Gly Thr Asp Phe Ala Leu Ser Ile Asn Ser Val Glu Thr
65                  70                  75                  80

Glu Asp Phe Gly Met Tyr Phe Cys Gln Gln Ser Gly Ser Trp Pro His
                85                  90                  95

Thr Phe Gly Gly Gly Thr Lys Leu Glu Ile Lys
            100                 105

<210> SEQ ID NO 9
```

<211> LENGTH: 84
<212> TYPE: DNA
<213> ORGANISM: Artificial Sequence
<220> FEATURE:
<223> OTHER INFORMATION: Description of Artificial Sequence: oligonucleotide

<400> SEQUENCE: 9
caggtgcagc tggtggagtc tgggggaggc gttgtgcagc ctggaaggtc cctgagactc    60
tcctgtgcag cctctggatt cacc    84

<210> SEQ ID NO 10
<211> LENGTH: 84
<212> TYPE: DNA
<213> ORGANISM: Artificial Sequence
<220> FEATURE:
<223> OTHER INFORMATION: Description of Artificial Sequence: oligonucleotide

<400> SEQUENCE: 10 aactttgcg acccactcca gacccttgcc cggagcctgg cgaacccaag acatgtcata    60
gctactgaag gtgaatccag aggc    84

<210> SEQ ID NO 11
<211> LENGTH: 87
<212> TYPE: DNA
<213> ORGANISM: Artificial Sequence
<220> FEATURE:
<223> OTHER INFORMATION: Description of Artificial Sequence: oligonucleotide

<400> SEQUENCE: 11
tgggtcgcaa aagttagtag tggtggtggt agcacctact atttagacac tgtgcagggc    60
cgattcacca tctccagaga caatagt    87

<210> SEQ ID NO 12
<211> LENGTH: 81
<212> TYPE: DNA
<213> ORGANISM: Artificial Sequence
<220> FEATURE:
<223> OTHER INFORMATION: Description of Artificial Sequence: oligonucleotide

<400> SEQUENCE: 12
tgcacagtaa tacacggctg tgtcctcggc tctcagagag ttcatttgca ggtatagggt    60
gttcttacta ttgtctctgg a    81

<210> SEQ ID NO 13
<211> LENGTH: 75
<212> TYPE: DNA
<213> ORGANISM: Artificial Sequence
<220> FEATURE:
<223> OTHER INFORMATION: Description of Artificial Sequence: oligonucleotide

<400> SEQUENCE: 13
gtgtattact gtgcaagaca taactacggc agttttgctt actggggcca agggactaca    60
gtgactgttt ctagt    75

<210> SEQ ID NO 14
<211> LENGTH: 87
<212> TYPE: DNA
<213> ORGANISM: Artificial Sequence
<220> FEATURE:

<223> OTHER INFORMATION: Description of Artificial Sequence:
      oligonucleotide

<400> SEQUENCE: 14
gagattgtgc taactcagtc tccagccacc ctgtctctca gcccaggaga aagggcgact    60
ctttcctgcc aggccagcca aagtatt                                       87

<210> SEQ ID NO 15
<211> LENGTH: 72
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 15
gatgagaagc cttggggctt gaccaggcct tgttgatac cagtgtaggt ggttgctaat     60
actttggctg gc                                                       72

<210> SEQ ID NO 16
<211> LENGTH: 84
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 16
ccaaggcttc tcatcwasta tcgttcccag tccatctctg ggatcccgc caggttcagt     60 ggcagtggat cagggacaga tttc                                          84

<210> SEQ ID NO 17
<211> LENGTH: 81
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 17
gctgccactc tgttgacagw aatagactgc aaaatcttca ggctccagac tggagatagt    60
gagggtgaaa tctgtccctg a                                             81

<210> SEQ ID NO 18
<211> LENGTH: 57
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 18
caacagagtg gcagctggcc tcacacgttc ggaggggga ccaaggtgga aattaag        57

<210> SEQ ID NO 19
<211> LENGTH: 36
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 19
gcccaaccag ccatggccga tattgtgcta actcag                             36

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 20
acagttggtg cagcatcagc                                                  20

<210> SEQ ID NO 21
<211> LENGTH: 36
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 21
acccctgtgg caaaagccga agtgcagctg gtggag                                36

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 22 gatggggtg tcgttttggc                                                   20

<210> SEQ ID NO 23
<211> LENGTH: 87
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 23
gagattgtgc taactcagtc tccagccacc ctgtctctca gcccaggaga aagggcgact      60
ctttcctgcc aggccagcca aagtatt                                          87

<210> SEQ ID NO 24
<211> LENGTH: 75
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 24
ttagatgaga agccttgggg cttgaccagg cctttgttga taccagtgta ggtggttgct      60
aatactttgg ctggc                                                       75

<210> SEQ ID NO 25
<211> LENGTH: 84
<212> TYPE: DNA
<213> ORGANISM: Artificial Sequence
<220> FEATURE:
<223> OTHER INFORMATION: Description of Artificial Sequence:
      oligonucleotide -continued

```
<400> SEQUENCE: 25
ccaaggcttc tcatctaata tcgttcccag tccatctctg ggatcccgc caggttcagt    60 ggcagtggat cagggacaga tttc                                         84

<210> SEQ ID NO 26
<211> LENGTH: 81
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 26
gctgccactc tgttgacagt aatagactgc aaaatcttca ggctccagac tggagatagt    60
gagggtgaaa tctgtccctg a                                              81

<210> SEQ ID NO 27
<211> LENGTH: 57
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 27
caacagagtg gcagctggcc tcacacgttc ggaggggga ccaaggtgga aattaag       57

<210> SEQ ID NO 28
<211> LENGTH: 10
<212> TYPE: PRT
<213> ORGANISM: Artificial Sequence
<220> FEATURE:
<223> OTHER INFORMATION: Description of Artificial Sequence: antigen

<400> SEQUENCE: 28

Tyr Pro Tyr Asp Val Pro Asp Tyr Ala Ser
 1               5                  10

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 29
gctactgaag gcgaatccag ag                                            22

<210> SEQ ID NO 30
<211> LENGTH: 23
<212> TYPE: DNA
<213> ORGANISM: Artificial Sequence
<220> FEATURE:
<221> NAME/KEY: misc_feature
<222> LOCATION: (11)..(13)
<223> OTHER INFORMATION: NNN = codon specifying any amino acid other
      than Lys.
<220> FEATURE:
<223> OTHER INFORMATION: Description of Artificial Sequence:
      oligonucleotide

<400> SEQUENCE: 30
gggaacgata nnngatgaga agc                                           23
```

```
<210> SEQ ID NO 31
<211> LENGTH: 321
<212> TYPE: DNA
<213> ORGANISM: Artificial Sequence
<220> FEATURE:
<223> OTHER INFORMATION: Description of Artificial Sequence: grafted
      antibody variable region
<220> FEATURE:
<221> NAME/KEY: variation
<222> LOCATION: (145)..(147)
<223> OTHER INFORMATION: NNN=CGT OR ATG;

<400> SEQUENCE: 31
gagattgtgc taactcagtc tccagccacc ctgtctctca gcccaggaga aagggcgact      60
ctttcctgcc aggccagcca agtattagc aaccacctac actggtatca acaaaggcct     120
ggtcaagccc caaggcttct catcnnntat cgttcccagt ccatctctgg atccccgcc     180 aggttcagtg gcagtggatc agggacagat ttcaccctca ctatctccag tctggagcct   240
gaagattttg cagtctatta ctgtcaacag agtggcagct ggcctcacac gttcggaggg   300
gggaccaagg tggaaattaa g                                              321

<210> SEQ ID NO 32
<211> LENGTH: 107
<212> TYPE: PRT
<213> ORGANISM: Artificial Sequence
<220> FEATURE:
<221> NAME/KEY: VARIANT
<222> LOCATION: (49)
<223> OTHER INFORMATION: Xaa = Arg or Met
<220> FEATURE:
<223> OTHER INFORMATION: Description of Artificial Sequence: grafted
      antibody variable region

<400> SEQUENCE: 32

Glu Ile Val Leu Thr Gln Ser Pro Ala Thr Leu Ser Leu Ser Pro Gly
 1               5                  10                  15

Glu Arg Ala Thr Leu Ser Cys Gln Ala Ser Gln Ser Ile Ser Asn His
                20                  25                  30

Leu His Trp Tyr Gln Gln Arg Pro Gly Gln Ala Pro Arg Leu Leu Ile
            35                  40                  45

Xaa Tyr Arg Ser Gln Ser Ile Ser Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Ser Gly Ser Trp Pro His
                85                  90                  95

Thr Phe Gly Gly Gly Thr Lys Val Glu Ile Lys
            100                 105

<210> SEQ ID NO 33
<211> LENGTH: 30
<212> TYPE: DNA
<213> ORGANISM: Mus musculus
<220> FEATURE:
<221> NAME/KEY: CDS
<222> LOCATION: (1)..(30)

<400> SEQUENCE: 33 gga ttc acc ttc agt agc tat gac atg tct                              30
Gly Phe Thr Phe Ser Ser Tyr Asp Met Ser
 1               5                  10

<210> SEQ ID NO 34
```

```
<211> LENGTH: 10
<212> TYPE: PRT
<213> ORGANISM: Mus musculus

<400> SEQUENCE: 34

Gly Phe Thr Phe Ser Ser Tyr Asp Met Ser
 1               5                  10

<210> SEQ ID NO 35
<211> LENGTH: 30
<212> TYPE: DNA
<213> ORGANISM: Mus musculus
<220> FEATURE:
<221> NAME/KEY: CDS
<222> LOCATION: (1)..(30)

<400> SEQUENCE: 35 tgg gtc gca aaa gtt agt agt ggt ggt ggt                              30
Trp Val Ala Lys Val Ser Ser Gly Gly Gly
 1               5                  10

<210> SEQ ID NO 36
<211> LENGTH: 10
<212> TYPE: PRT
<213> ORGANISM: Mus musculus

<400> SEQUENCE: 36

Trp Val Ala Lys Val Ser Ser Gly Gly Gly
 1               5                  10

<210> SEQ ID NO 37
<211> LENGTH: 30
<212> TYPE: DNA
<213> ORGANISM: Mus musculus
<220> FEATURE:
<221> NAME/KEY: CDS
<222> LOCATION: (1)..(30)

<400> SEQUENCE: 37 agc acc tac tat tta gac act gtg cag ggc                              30
Ser Thr Tyr Tyr Leu Asp Thr Val Gln Gly
 1               5                  10

<210> SEQ ID NO 38
<211> LENGTH: 10
<212> TYPE: PRT
<213> ORGANISM: Mus musculus

<400> SEQUENCE: 38

Ser Thr Tyr Tyr Leu Asp Thr Val Gln Gly
 1               5                  10

<210> SEQ ID NO 39
<211> LENGTH: 30
<212> TYPE: DNA
<213> ORGANISM: Mus musculus
<220> FEATURE:
<221> NAME/KEY: CDS
<222> LOCATION: (1)..(30)

<400> SEQUENCE: 39 gca aga cat aac tac ggc agt ttt gct tac                              30
Ala Arg His Asn Tyr Gly Ser Phe Ala Tyr
 1               5                  10

<210> SEQ ID NO 40
<211> LENGTH: 10
```

```
<212> TYPE: PRT
<213> ORGANISM: Mus musculus

<400> SEQUENCE: 40

Ala Arg His Asn Tyr Gly Ser Phe Ala Tyr
 1               5                  10

<210> SEQ ID NO 41
<211> LENGTH: 39
<212> TYPE: DNA
<213> ORGANISM: Mus musculus
<220> FEATURE:
<221> NAME/KEY: CDS
<222> LOCATION: (1)..(39)

<400> SEQUENCE: 41 cag gcc agc caa agt att agc aac cac cta cac tgg tat                      39
Gln Ala Ser Gln Ser Ile Ser Asn His Leu His Trp Tyr
 1               5                  10

<210> SEQ ID NO 42
<211> LENGTH: 13
<212> TYPE: PRT
<213> ORGANISM: Mus musculus

<400> SEQUENCE: 42

Gln Ala Ser Gln Ser Ile Ser Asn His Leu His Trp Tyr
 1               5                  10

<210> SEQ ID NO 43
<211> LENGTH: 33
<212> TYPE: DNA
<213> ORGANISM: Mus musculus
<220> FEATURE:
<221> NAME/KEY: CDS
<222> LOCATION: (1)..(33)

<400> SEQUENCE: 43 ctt ctc atc cgt tat cgt tcc cag tcc atc tct                              33
Leu Leu Ile Arg Tyr Arg Ser Gln Ser Ile Ser
 1               5                  10

<210> SEQ ID NO 44
<211> LENGTH: 11
<212> TYPE: PRT
<213> ORGANISM: Mus musculus

<400> SEQUENCE: 44

Leu Leu Ile Arg Tyr Arg Ser Gln Ser Ile Ser
 1               5                  10

<210> SEQ ID NO 45
<211> LENGTH: 27
<212> TYPE: DNA
<213> ORGANISM: Mus musculus
<220> FEATURE:
<221> NAME/KEY: CDS
<222> LOCATION: (1)..(27)

<400> SEQUENCE: 45 caa cag agt ggc agc tgg cct cac acg                                      27
Gln Gln Ser Gly Ser Trp Pro His Thr
 1               5

<210> SEQ ID NO 46
<211> LENGTH: 9
<212> TYPE: PRT
```

<213> ORGANISM: Mus musculus

<400> SEQUENCE: 46

Gln Gln Ser Gly Ser Trp Pro His Thr
 1               5

<210> SEQ ID NO 47
<211> LENGTH: 30
<212> TYPE: DNA
<213> ORGANISM: Artificial Sequence
<220> FEATURE:
<221> NAME/KEY: CDS
<222> LOCATION: (1)..(30)
<223> OTHER INFORMATION: Description of Artificial Sequence: Mutated
      complementarity determining region (CDR)

<400> SEQUENCE: 47 gga act acc ttc agt agc tat gac atg tct                        30
Gly Thr Thr Phe Ser Ser Tyr Asp Met Ser
 1               5                  10

<210> SEQ ID NO 48
<211> LENGTH: 10
<212> TYPE: PRT
<213> ORGANISM: Artificial Sequence
<220> FEATURE:
<223> OTHER INFORMATION: Description of Artificial Sequence: Mutated
      complementarity determining region (CDR)

<400> SEQUENCE: 48

Gly Thr Thr Phe Ser Ser Tyr Asp Met Ser
 1               5                  10

<210> SEQ ID NO 49
<211> LENGTH: 30
<212> TYPE: DNA
<213> ORGANISM: Artificial Sequence
<220> FEATURE:
<221> NAME/KEY: CDS
<222> LOCATION: (1)..(30)
<223> OTHER INFORMATION: Description of Artificial Sequence: Mutated
      complementarity determining region (CDR)

<400> SEQUENCE: 49 gga ttc acc tgg agt agc tat gac atg tct                        30
Gly Phe Thr Trp Ser Ser Tyr Asp Met Ser
 1               5                  10

<210> SEQ ID NO 50
<211> LENGTH: 10
<212> TYPE: PRT
<213> ORGANISM: Artificial Sequence
<220> FEATURE:
<223> OTHER INFORMATION: Description of Artificial Sequence: Mutated
      complementarity determining region (CDR)

<400> SEQUENCE: 50

Gly Phe Thr Trp Ser Ser Tyr Asp Met Ser
 1               5                  10

<210> SEQ ID NO 51
<211> LENGTH: 30
<212> TYPE: DNA
<213> ORGANISM: Artificial Sequence
<220> FEATURE:
<221> NAME/KEY: CDS
<222> LOCATION: (1)..(30)
<223> OTHER INFORMATION: Description of Artificial Sequence: Mutated
      complementarity determining region (CDR)

```
<400> SEQUENCE: 51 gga ttc acc ttc ctg agc tat gac atg tct                          30
Gly Phe Thr Phe Leu Ser Tyr Asp Met Ser
 1               5                  10

<210> SEQ ID NO 52
<211> LENGTH: 10
<212> TYPE: PRT
<213> ORGANISM: Artificial Sequence
<220> FEATURE:
<223> OTHER INFORMATION: Description of Artificial Sequence: Mutated
      complementarity determining region (CDR)

<400> SEQUENCE: 52

Gly Phe Thr Phe Leu Ser Tyr Asp Met Ser
 1               5                  10

<210> SEQ ID NO 53
<211> LENGTH: 30
<212> TYPE: DNA
<213> ORGANISM: Artificial Sequence
<220> FEATURE:
<221> NAME/KEY: CDS
<222> LOCATION: (1)..(30)
<223> OTHER INFORMATION: Description of Artificial Sequence: Mutated
      complementarity determining region (CDR)

<400> SEQUENCE: 53 tgg gtc gca aaa gtt aaa agt ggt ggt ggt                          30
Trp Val Ala Lys Val Lys Ser Gly Gly Gly
 1               5                  10

<210> SEQ ID NO 54
<211> LENGTH: 10
<212> TYPE: PRT
<213> ORGANISM: Artificial Sequence
<220> FEATURE:
<223> OTHER INFORMATION: Description of Artificial Sequence: Mutated
      complementarity determining region (CDR)

<400> SEQUENCE: 54

Trp Val Ala Lys Val Lys Ser Gly Gly Gly
 1               5                  10

<210> SEQ ID NO 55
<211> LENGTH: 30
<212> TYPE: DNA
<213> ORGANISM: Artificial Sequence
<220> FEATURE:
<221> NAME/KEY: CDS
<222> LOCATION: (1)..(30)
<223> OTHER INFORMATION: Description of Artificial Sequence: Mutated
      complementarity determining region (CDR)

<400> SEQUENCE: 55 agc acc tac tat cct gac act gtg cag ggc                          30
Ser Thr Tyr Tyr Pro Asp Thr Val Gln Gly
 1               5                  10

<210> SEQ ID NO 56
<211> LENGTH: 10
<212> TYPE: PRT
<213> ORGANISM: Artificial Sequence
<220> FEATURE:
<223> OTHER INFORMATION: Description of Artificial Sequence: Mutated
      complementarity determining region (CDR)

<400> SEQUENCE: 56
```

Ser Thr Tyr Tyr Pro Asp Thr Val Gln Gly
1               5                   10

<210> SEQ ID NO 57
<211> LENGTH: 30
<212> TYPE: DNA
<213> ORGANISM: Artificial Sequence
<220> FEATURE:
<221> NAME/KEY: CDS
<222> LOCATION: (1)..(30)
<223> OTHER INFORMATION: Description of Artificial Sequence: Mutated
      complementarity determining region (CDR)

<400> SEQUENCE: 57 agc acc tac tat tta gac act gtg gag ggc                           30
Ser Thr Tyr Tyr Leu Asp Thr Val Glu Gly
1               5                   10

<210> SEQ ID NO 58
<211> LENGTH: 10
<212> TYPE: PRT
<213> ORGANISM: Artificial Sequence
<220> FEATURE:
<223> OTHER INFORMATION: Description of Artificial Sequence: Mutated
      complementarity determining region (CDR)

<400> SEQUENCE: 58

Ser Thr Tyr Tyr Leu Asp Thr Val Glu Gly
1               5                   10

<210> SEQ ID NO 59
<211> LENGTH: 30
<212> TYPE: DNA
<213> ORGANISM: Artificial Sequence
<220> FEATURE:
<221> NAME/KEY: CDS
<222> LOCATION: (1)..(30)
<223> OTHER INFORMATION: Description of Artificial Sequence: Mutated
      complementarity determining region (CDR)

<400> SEQUENCE: 59 gca aga cat aac cat ggc agt ttt gct tac                           30
Ala Arg His Asn His Gly Ser Phe Ala Tyr
1               5                   10

<210> SEQ ID NO 60
<211> LENGTH: 10
<212> TYPE: PRT
<213> ORGANISM: Artificial Sequence
<220> FEATURE:
<223> OTHER INFORMATION: Description of Artificial Sequence: Mutated
      complementarity determining region (CDR)

<400> SEQUENCE: 60

Ala Arg His Asn His Gly Ser Phe Ala Tyr
1               5                   10

<210> SEQ ID NO 61
<211> LENGTH: 30
<212> TYPE: DNA
<213> ORGANISM: Artificial Sequence
<220> FEATURE:
<221> NAME/KEY: CDS
<222> LOCATION: (1)..(30)
<223> OTHER INFORMATION: Description of Artificial Sequence: Mutated
      complementarity determining region (CDR)

<400> SEQUENCE: 61

```
gca aga cat aac tac ggc agt tat gct tac                          30
Ala Arg His Asn Tyr Gly Ser Tyr Ala Tyr
 1               5                  10

<210> SEQ ID NO 62
<211> LENGTH: 10
<212> TYPE: PRT
<213> ORGANISM: Artificial Sequence
<220> FEATURE:
<223> OTHER INFORMATION: Description of Artificial Sequence: Mutated
      complementarity determining region (CDR)

<400> SEQUENCE: 62

Ala Arg His Asn Tyr Gly Ser Tyr Ala Tyr
 1               5                  10

<210> SEQ ID NO 63
<211> LENGTH: 30
<212> TYPE: DNA
<213> ORGANISM: Artificial Sequence
<220> FEATURE:
<221> NAME/KEY: CDS
<222> LOCATION: (1)..(30)
<223> OTHER INFORMATION: Description of Artificial Sequence: Mutated
      complementarity determining region (CDR)

<400> SEQUENCE: 63 gca aga cat aac tac ggc agt ttt gat tac                          30
Ala Arg His Asn Tyr Gly Ser Phe Asp Tyr
 1               5                  10

<210> SEQ ID NO 64
<211> LENGTH: 10
<212> TYPE: PRT
<213> ORGANISM: Artificial Sequence
<220> FEATURE:
<223> OTHER INFORMATION: Description of Artificial Sequence: Mutated
      complementarity determining region (CDR)

<400> SEQUENCE: 64

Ala Arg His Asn Tyr Gly Ser Phe Asp Tyr
 1               5                  10

<210> SEQ ID NO 65
<211> LENGTH: 30
<212> TYPE: DNA
<213> ORGANISM: Artificial Sequence
<220> FEATURE:
<221> NAME/KEY: CDS
<222> LOCATION: (1)..(30)
<223> OTHER INFORMATION: Description of Artificial Sequence: Mutated
      complementarity determining region (CDR)

<400> SEQUENCE: 65 gca aga cat aac tac ggc agt ttt tat tac                          30
Ala Arg His Asn Tyr Gly Ser Phe Tyr Tyr
 1               5                  10

<210> SEQ ID NO 66
<211> LENGTH: 10
<212> TYPE: PRT
<213> ORGANISM: Artificial Sequence
<220> FEATURE:
<223> OTHER INFORMATION: Description of Artificial Sequence: Mutated
      complementarity determining region (CDR)

<400> SEQUENCE: 66

Ala Arg His Asn Tyr Gly Ser Phe Tyr Tyr
 1               5                  10
```

<210> SEQ ID NO 67
<211> LENGTH: 30
<212> TYPE: DNA
<213> ORGANISM: Artificial Sequence
<220> FEATURE:
<221> NAME/KEY: CDS
<222> LOCATION: (1)..(30)
<223> OTHER INFORMATION: Description of Artificial Sequence: Mutated
      complementarity determining region (CDR)

<400> SEQUENCE: 67 gca aga cat aac tac ggc agt ttt gct tct                         30
Ala Arg His Asn Tyr Gly Ser Phe Ala Ser
 1               5                  10

<210> SEQ ID NO 68
<211> LENGTH: 10
<212> TYPE: PRT
<213> ORGANISM: Artificial Sequence
<220> FEATURE:
<223> OTHER INFORMATION: Description of Artificial Sequence: Mutated
      complementarity determining region (CDR)

<400> SEQUENCE: 68

Ala Arg His Asn Tyr Gly Ser Phe Ala Ser
 1               5                  10

<210> SEQ ID NO 69
<211> LENGTH: 30
<212> TYPE: DNA
<213> ORGANISM: Artificial Sequence
<220> FEATURE:
<221> NAME/KEY: CDS
<222> LOCATION: (1)..(30)
<223> OTHER INFORMATION: Description of Artificial Sequence: Mutated
      complementarity determining region (CDR)

<400> SEQUENCE: 69 gca aga cat aac tac ggc agt ttt gct act                         30
Ala Arg His Asn Tyr Gly Ser Phe Ala Thr
 1               5                  10

<210> SEQ ID NO 70
<211> LENGTH: 10
<212> TYPE: PRT
<213> ORGANISM: Artificial Sequence
<220> FEATURE:
<223> OTHER INFORMATION: Description of Artificial Sequence: Mutated
      complementarity determining region (CDR)

<400> SEQUENCE: 70

Ala Arg His Asn Tyr Gly Ser Phe Ala Thr
 1               5                  10

<210> SEQ ID NO 71
<211> LENGTH: 30
<212> TYPE: DNA
<213> ORGANISM: Artificial Sequence
<220> FEATURE:
<221> NAME/KEY: CDS
<222> LOCATION: (1)..(30)
<223> OTHER INFORMATION: Description of Artificial Sequence: Mutated
      complementarity determining region (CDR)

<400> SEQUENCE: 71 gca aga cat aac tac ggc agt ttt gct gat                         30
Ala Arg His Asn Tyr Gly Ser Phe Ala Asp
 1               5                  10

```
<210> SEQ ID NO 72
<211> LENGTH: 10
<212> TYPE: PRT
<213> ORGANISM: Artificial Sequence
<220> FEATURE:
<223> OTHER INFORMATION: Description of Artificial Sequence: Mutated
      complementarity determining region (CDR)

<400> SEQUENCE: 72

Ala Arg His Asn Tyr Gly Ser Phe Ala Asp
  1               5                  10

<210> SEQ ID NO 73
<211> LENGTH: 30
<212> TYPE: DNA
<213> ORGANISM: Artificial Sequence
<220> FEATURE:
<221> NAME/KEY: CDS
<222> LOCATION: (1)..(30)
<223> OTHER INFORMATION: Description of Artificial Sequence: Mutated
      complementarity determining region (CDR)

<400> SEQUENCE: 73 gca aga cat aac tac ggc agt ttt gct gag                              30
Ala Arg His Asn Tyr Gly Ser Phe Ala Glu
  1               5                  10

<210> SEQ ID NO 74
<211> LENGTH: 10
<212> TYPE: PRT
<213> ORGANISM: Artificial Sequence
<220> FEATURE:
<223> OTHER INFORMATION: Description of Artificial Sequence: Mutated
      complementarity determining region (CDR)

<400> SEQUENCE: 74

Ala Arg His Asn Tyr Gly Ser Phe Ala Glu
  1               5                  10

<210> SEQ ID NO 75
<211> LENGTH: 30
<212> TYPE: DNA
<213> ORGANISM: Artificial Sequence
<220> FEATURE:
<221> NAME/KEY: CDS
<222> LOCATION: (1)..(30)
<223> OTHER INFORMATION: Description of Artificial Sequence: Mutated
      complementarity determining region (CDR)

<400> SEQUENCE: 75 gca aga cat aac tac ggc agt ttt gct atg                              30
Ala Arg His Asn Tyr Gly Ser Phe Ala Met
  1               5                  10

<210> SEQ ID NO 76
<211> LENGTH: 10
<212> TYPE: PRT
<213> ORGANISM: Artificial Sequence
<220> FEATURE:
<223> OTHER INFORMATION: Description of Artificial Sequence: Mutated
      complementarity determining region (CDR)

<400> SEQUENCE: 76

Ala Arg His Asn Tyr Gly Ser Phe Ala Met
  1               5                  10

<210> SEQ ID NO 77
```

```
<211> LENGTH: 30
<212> TYPE: DNA
<213> ORGANISM: Artificial Sequence
<220> FEATURE:
<221> NAME/KEY: CDS
<222> LOCATION: (1)..(30)
<223> OTHER INFORMATION: Description of Artificial Sequence: Mutated
      complementarity determining region (CDR)

<400> SEQUENCE: 77 gca aga cat aac tac ggc agt ttt gct ggg                           30
Ala Arg His Asn Tyr Gly Ser Phe Ala Gly
 1               5                  10

<210> SEQ ID NO 78
<211> LENGTH: 10
<212> TYPE: PRT
<213> ORGANISM: Artificial Sequence
<220> FEATURE:
<223> OTHER INFORMATION: Description of Artificial Sequence: Mutated
      complementarity determining region (CDR)

<400> SEQUENCE: 78

Ala Arg His Asn Tyr Gly Ser Phe Ala Gly
 1               5                  10

<210> SEQ ID NO 79
<211> LENGTH: 30
<212> TYPE: DNA
<213> ORGANISM: Artificial Sequence
<220> FEATURE:
<221> NAME/KEY: CDS
<222> LOCATION: (1)..(30)
<223> OTHER INFORMATION: Description of Artificial Sequence: Mutated
      complementarity determining region (CDR)

<400> SEQUENCE: 79 gca aga cat aac tac ggc agt ttt gct gct                           30
Ala Arg His Asn Tyr Gly Ser Phe Ala Ala
 1               5                  10

<210> SEQ ID NO 80
<211> LENGTH: 10
<212> TYPE: PRT
<213> ORGANISM: Artificial Sequence
<220> FEATURE:
<223> OTHER INFORMATION: Description of Artificial Sequence: Mutated
      complementarity determining region (CDR)

<400> SEQUENCE: 80

Ala Arg His Asn Tyr Gly Ser Phe Ala Ala
 1               5                  10

<210> SEQ ID NO 81
<211> LENGTH: 39
<212> TYPE: DNA
<213> ORGANISM: Artificial Sequence
<220> FEATURE:
<221> NAME/KEY: CDS
<222> LOCATION: (1)..(39)
<223> OTHER INFORMATION: Description of Artificial Sequence: Mutated
      complementarity determining region (CDR)

<400> SEQUENCE: 81 cag gcc agc caa agt att agc aac ttt cta cac tgg tat               39
Gln Ala Ser Gln Ser Ile Ser Asn Phe Leu His Trp Tyr
 1               5                  10

<210> SEQ ID NO 82
```

```
<211> LENGTH: 13
<212> TYPE: PRT
<213> ORGANISM: Artificial Sequence
<220> FEATURE:
<223> OTHER INFORMATION: Description of Artificial Sequence: Mutated
      complementarity determining region (CDR)

<400> SEQUENCE: 82

Gln Ala Ser Gln Ser Ile Ser Asn Phe Leu His Trp Tyr
  1               5                  10

<210> SEQ ID NO 83
<211> LENGTH: 33
<212> TYPE: DNA
<213> ORGANISM: Artificial Sequence
<220> FEATURE:
<221> NAME/KEY: CDS
<222> LOCATION: (1)..(33)
<223> OTHER INFORMATION: Description of Artificial Sequence: Mutated
      complementarity determining region (CDR)

<400> SEQUENCE: 83 ctt ctc atc cgt tat tct tcc cag tcc atc tct                         33
Leu Leu Ile Arg Tyr Ser Ser Gln Ser Ile Ser
  1               5                  10

<210> SEQ ID NO 84
<211> LENGTH: 11
<212> TYPE: PRT
<213> ORGANISM: Artificial Sequence
<220> FEATURE:
<223> OTHER INFORMATION: Description of Artificial Sequence: Mutated
      complementarity determining region (CDR)

<400> SEQUENCE: 84

Leu Leu Ile Arg Tyr Ser Ser Gln Ser Ile Ser
  1               5                  10

<210> SEQ ID NO 85
<211> LENGTH: 27
<212> TYPE: DNA
<213> ORGANISM: Artificial Sequence
<220> FEATURE:
<221> NAME/KEY: CDS
<222> LOCATION: (1)..(27)
<223> OTHER INFORMATION: Description of Artificial Sequence: Mutated
      complementarity determining region (CDR)

<400> SEQUENCE: 85 caa cag agt aat agc tgg cct cac acg                                 27
Gln Gln Ser Asn Ser Trp Pro His Thr
  1               5

<210> SEQ ID NO 86
<211> LENGTH: 9
<212> TYPE: PRT
<213> ORGANISM: Artificial Sequence
<220> FEATURE:
<223> OTHER INFORMATION: Description of Artificial Sequence: Mutated
      complementarity determining region (CDR)

<400> SEQUENCE: 86

Gln Gln Ser Asn Ser Trp Pro His Thr
  1               5

<210> SEQ ID NO 87
<211> LENGTH: 27
<212> TYPE: DNA
<213> ORGANISM: Artificial Sequence
```

```
<220> FEATURE:
<221> NAME/KEY: CDS
<222> LOCATION: (1)..(27)
<223> OTHER INFORMATION: Description of Artificial Sequence:  Mutated
      complementarity determining region (CDR)

<400> SEQUENCE: 87 caa cag agt act agc tgg cct cac act                                  27
Gln Gln Ser Thr Ser Trp Pro His Thr
  1               5

<210> SEQ ID NO 88
<211> LENGTH: 9
<212> TYPE: PRT
<213> ORGANISM: Artificial Sequence
<220> FEATURE:
<223> OTHER INFORMATION: Description of Artificial Sequence:  Mutated
      complementarity determining region (CDR)

<400> SEQUENCE: 88

Gln Gln Ser Thr Ser Trp Pro His Thr
  1               5

<210> SEQ ID NO 89
<211> LENGTH: 27
<212> TYPE: DNA
<213> ORGANISM: Artificial Sequence
<220> FEATURE:
<221> NAME/KEY: CDS
<222> LOCATION: (1)..(27)
<223> OTHER INFORMATION: Description of Artificial Sequence:  Mutated
      complementarity determining region (CDR)

<400> SEQUENCE: 89 caa cag agt ggc agc tgg cct ctg acg                                  27
Gln Gln Ser Gly Ser Trp Pro Leu Thr
  1               5

<210> SEQ ID NO 90
<211> LENGTH: 9
<212> TYPE: PRT
<213> ORGANISM: Artificial Sequence
<220> FEATURE:
<223> OTHER INFORMATION: Description of Artificial Sequence:  Mutated
      complementarity determining region (CDR)

<400> SEQUENCE: 90

Gln Gln Ser Gly Ser Trp Pro Leu Thr
  1               5

<210> SEQ ID NO 91
<211> LENGTH: 27
<212> TYPE: DNA
<213> ORGANISM: Artificial Sequence
<220> FEATURE:
<221> NAME/KEY: CDS
<222> LOCATION: (1)..(27)
<223> OTHER INFORMATION: Description of Artificial Sequence:  Mutated
      complementarity determining region (CDR)

<400> SEQUENCE: 91 caa cag agt ggc agc tgg cct cag acg                                  27
Gln Gln Ser Gly Ser Trp Pro Gln Thr
  1               5

<210> SEQ ID NO 92
<211> LENGTH: 9
<212> TYPE: PRT
<213> ORGANISM: Artificial Sequence
```

```
<220> FEATURE:
<223> OTHER INFORMATION: Description of Artificial Sequence: Mutated
      complementarity determining region (CDR)

<400> SEQUENCE: 92

Gln Gln Ser Gly Ser Trp Pro Gln Thr
 1               5

<210> SEQ ID NO 93
<211> LENGTH: 30
<212> TYPE: DNA
<213> ORGANISM: Artificial Sequence
<220> FEATURE:
<221> NAME/KEY: CDS
<222> LOCATION: (1)..(30)
<223> OTHER INFORMATION: Description of Artificial Sequence: Mutated
      complementarity determining region (CDR)

<400> SEQUENCE: 93 gca aga cat aac cat ggc agt ttt tat tct                             30
Ala Arg His Asn His Gly Ser Phe Tyr Ser
 1               5                  10

<210> SEQ ID NO 94
<211> LENGTH: 10
<212> TYPE: PRT
<213> ORGANISM: Artificial Sequence
<220> FEATURE:
<223> OTHER INFORMATION: Description of Artificial Sequence: Mutated
      complementarity determining region (CDR)

<400> SEQUENCE: 94

Ala Arg His Asn His Gly Ser Phe Tyr Ser
 1               5                  10

<210> SEQ ID NO 95
<211> LENGTH: 30
<212> TYPE: DNA
<213> ORGANISM: Artificial Sequence
<220> FEATURE:
<221> NAME/KEY: CDS
<222> LOCATION: (1)..(30)
<223> OTHER INFORMATION: Description of Artificial Sequence: Mutated
      complementarity determining region (CDR)

<400> SEQUENCE: 95 gca aga cat aac cat ggc agt ttt gct tct                             30
Ala Arg His Asn His Gly Ser Phe Ala Ser
 1               5                  10

<210> SEQ ID NO 96
<211> LENGTH: 10
<212> TYPE: PRT
<213> ORGANISM: Artificial Sequence
<220> FEATURE:
<223> OTHER INFORMATION: Description of Artificial Sequence: Mutated
      complementarity determining region (CDR)

<400> SEQUENCE: 96

Ala Arg His Asn His Gly Ser Phe Ala Ser
 1               5                  10

<210> SEQ ID NO 97
<211> LENGTH: 30
<212> TYPE: DNA
<213> ORGANISM: Artificial Sequence
<220> FEATURE:
<221> NAME/KEY: CDS
<222> LOCATION: (1)..(30)
```

-continued

```
<223> OTHER INFORMATION: Description of Artificial Sequence: Mutated
      complementarity determining region (CDR)

<400> SEQUENCE: 97 gca aga cat aac tac ggc agt ttt tat gag                          30
Ala Arg His Asn Tyr Gly Ser Phe Tyr Glu
 1               5                  10

<210> SEQ ID NO 98
<211> LENGTH: 10
<212> TYPE: PRT
<213> ORGANISM: Artificial Sequence
<220> FEATURE:
<223> OTHER INFORMATION: Description of Artificial Sequence: Mutated
      complementarity determining region (CDR)

<400> SEQUENCE: 98

Ala Arg His Asn Tyr Gly Ser Phe Tyr Glu
 1               5                  10

<210> SEQ ID NO 99
<211> LENGTH: 30
<212> TYPE: DNA
<213> ORGANISM: Artificial Sequence
<220> FEATURE:
<221> NAME/KEY: CDS
<222> LOCATION: (1)..(30)
<223> OTHER INFORMATION: Description of Artificial Sequence: Mutated
      complementarity determining region (CDR)

<400> SEQUENCE: 99 gca aga cat aac tac ggc agt ttt tat tct                          30
Ala Arg His Asn Tyr Gly Ser Phe Tyr Ser
 1               5                  10

<210> SEQ ID NO 100
<211> LENGTH: 10
<212> TYPE: PRT
<213> ORGANISM: Artificial Sequence
<220> FEATURE:
<223> OTHER INFORMATION: Description of Artificial Sequence: Mutated
      complementarity determining region (CDR)

<400> SEQUENCE: 100

Ala Arg His Asn Tyr Gly Ser Phe Tyr Ser
 1               5                  10

<210> SEQ ID NO 101
<211> LENGTH: 51
<212> TYPE: DNA
<213> ORGANISM: Artificial Sequence
<220> FEATURE:
<221> NAME/KEY: CDS
<222> LOCATION: (1)..(51)
<223> OTHER INFORMATION: Description of Artificial Sequence: Mutated
      complementarity determining region (CDR)

<400> SEQUENCE: 101 aaa gtt agt agt ggt ggt ggt agc acc tac tat tta gac act gtg cag    48
Lys Val Ser Ser Gly Gly Gly Ser Thr Tyr Tyr Leu Asp Thr Val Gln
 1               5                  10                  15 ggc                                                                51
Gly

<210> SEQ ID NO 102
<211> LENGTH: 17
<212> TYPE: PRT
<213> ORGANISM: Artificial Sequence
```

```
<220> FEATURE:
<223> OTHER INFORMATION: Description of Artificial Sequence:  Mutated
      complementarity determining region (CDR)

<400> SEQUENCE: 102

Lys Val Ser Ser Gly Gly Gly Ser Thr Tyr Tyr Leu Asp Thr Val Gln
 1               5                  10                  15

Gly

<210> SEQ ID NO 103
<211> LENGTH: 51
<212> TYPE: DNA
<213> ORGANISM: Artificial Sequence
<220> FEATURE:
<221> NAME/KEY: CDS
<222> LOCATION: (1)..(51)
<223> OTHER INFORMATION: Description of Artificial Sequence:  Mutated
      complementarity determining region (CDR)

<400> SEQUENCE: 103 aaa gtt agt agt ggt ggt ggt agc acc tac tat cca gac act gtg cag      48
Lys Val Ser Ser Gly Gly Gly Ser Thr Tyr Tyr Pro Asp Thr Val Gln
 1               5                  10                  15 ggc                                                                  51
Gly

<210> SEQ ID NO 104
<211> LENGTH: 17
<212> TYPE: PRT
<213> ORGANISM: Artificial Sequence
<220> FEATURE:
<223> OTHER INFORMATION: Description of Artificial Sequence:  Mutated
      complementarity determining region (CDR)

<400> SEQUENCE: 104

Lys Val Ser Ser Gly Gly Gly Ser Thr Tyr Tyr Pro Asp Thr Val Gln
 1               5                  10                  15

Gly

<210> SEQ ID NO 105
<211> LENGTH: 24
<212> TYPE: DNA
<213> ORGANISM: Artificial Sequence
<220> FEATURE:
<221> NAME/KEY: CDS
<222> LOCATION: (1)..(24)
<223> OTHER INFORMATION: Description of Artificial Sequence:  Mutated
      complementarity determining region (CDR)

<400> SEQUENCE: 105 cat ctt cat ggc agt ttt gct tct                                      24
His Leu His Gly Ser Phe Ala Ser
 1               5

<210> SEQ ID NO 106
<211> LENGTH: 8
<212> TYPE: PRT
<213> ORGANISM: Artificial Sequence
<220> FEATURE:
<223> OTHER INFORMATION: Description of Artificial Sequence:  Mutated
      complementarity determining region (CDR)

<400> SEQUENCE: 106

His Leu His Gly Ser Phe Ala Ser
 1               5
```

<210> SEQ ID NO 107
<211> LENGTH: 33
<212> TYPE: DNA
<213> ORGANISM: Artificial Sequence
<220> FEATURE:
<221> NAME/KEY: CDS
<222> LOCATION: (1)..(33)
<223> OTHER INFORMATION: Description of Artificial Sequence: Mutated
      complementarity determining region (CDR)

<400> SEQUENCE: 107 cag gcc agc caa agt att agc aac cac cta cac                          33
Gln Ala Ser Gln Ser Ile Ser Asn His Leu His
  1               5                  10

<210> SEQ ID NO 108
<211> LENGTH: 11
<212> TYPE: PRT
<213> ORGANISM: Artificial Sequence
<220> FEATURE:
<223> OTHER INFORMATION: Description of Artificial Sequence: Mutated
      complementarity determining region (CDR)

<400> SEQUENCE: 108

Gln Ala Ser Gln Ser Ile Ser Asn His Leu His
  1               5                  10

<210> SEQ ID NO 109
<211> LENGTH: 33
<212> TYPE: DNA
<213> ORGANISM: Artificial Sequence
<220> FEATURE:
<221> NAME/KEY: CDS
<222> LOCATION: (1)..(33)
<223> OTHER INFORMATION: Description of Artificial Sequence: Mutated
      complementarity determining region (CDR)

<400> SEQUENCE: 109 cag gcc agc caa agt att agc aac ttc cta cac                          33
Gln Ala Ser Gln Ser Ile Ser Asn Phe Leu His
  1               5                  10

<210> SEQ ID NO 110
<211> LENGTH: 11
<212> TYPE: PRT
<213> ORGANISM: Artificial Sequence
<220> FEATURE:
<223> OTHER INFORMATION: Description of Artificial Sequence: Mutated
      complementarity determining region (CDR)

<400> SEQUENCE: 110

Gln Ala Ser Gln Ser Ile Ser Asn Phe Leu His
  1               5                  10

<210> SEQ ID NO 111
<211> LENGTH: 21
<212> TYPE: DNA
<213> ORGANISM: Artificial Sequence
<220> FEATURE:
<221> NAME/KEY: CDS
<222> LOCATION: (1)..(21)
<223> OTHER INFORMATION: Description of Artificial Sequence: Mutated
      complementarity determining region (CDR)

<400> SEQUENCE: 111 tat cgt tcc cag tcc atc tct                                          21
Tyr Arg Ser Gln Ser Ile Ser
  1               5

```
-continued

<210> SEQ ID NO 112
<211> LENGTH: 7
<212> TYPE: PRT
<213> ORGANISM: Artificial Sequence
<220> FEATURE:
<223> OTHER INFORMATION: Description of Artificial Sequence: Mutated
      complementarity determining region (CDR)

<400> SEQUENCE: 112

Tyr Arg Ser Gln Ser Ile Ser
 1               5
```